US010145848B2

(12) United States Patent
Crews et al.

(10) Patent No.: US 10,145,848 B2
(45) Date of Patent: Dec. 4, 2018

(54) SMALL-MOLECULE HYDROPHOBIC TAGGING OF FUSION PROTEINS AND INDUCED DEGRADATION OF SAME

(71) Applicant: YALE UNIVERSITY, New Haven, CT (US)

(72) Inventors: Craig M. Crews, New Haven, CT (US); Hyun Seop Tae, New Haven, CT (US); Ashley R. Schneekloth, New Market, MD (US); Taavi Neklesa, Orange, CT (US); Thomas Sundberg, New Haven, CT (US)

(73) Assignee: Yale University, New Haven, CT (US)

( * ) Notice: Subject to any disclaimer, the term of this patent is extended or adjusted under 35 U.S.C. 154(b) by 0 days.

(21) Appl. No.: 15/480,627

(22) Filed: Apr. 6, 2017

(65) Prior Publication Data
US 2017/0307614 A1 Oct. 26, 2017

Related U.S. Application Data

(62) Division of application No. 15/343,640, filed on Nov. 4, 2016, now Pat. No. 9,632,089, which is a division of application No. 13/992,076, filed as application No. PCT/US2011/063401 on Dec. 6, 2011, now Pat. No. 9,500,653.

(60) Provisional application No. 61/420,584, filed on Dec. 7, 2010, provisional application No. 61/530,014, filed on Sep. 1, 2011.

(51) Int. Cl.
G01N 33/573 (2006.01)
G01N 33/50 (2006.01)
C07K 1/13 (2006.01)
C12N 9/14 (2006.01)
A61K 47/48 (2006.01)

(52) U.S. Cl.
CPC ..... *G01N 33/573* (2013.01); *A61K 47/48015* (2013.01); *C07K 1/13* (2013.01); *C12N 9/14* (2013.01); *G01N 33/5008* (2013.01); *C07K 2319/20* (2013.01); *C07K 2319/95* (2013.01); *G01N 2500/10* (2013.01)

(58) Field of Classification Search
None
See application file for complete search history.

(56) References Cited

U.S. PATENT DOCUMENTS

| 6,303,618 | B1 | 10/2001 | Griffin et al. |
| 2004/0163138 | A1 | 8/2004 | Reed et al. |
| 2004/0214258 | A1 | 10/2004 | Wood et al. |
| 2006/0149073 | A1 | 7/2006 | Tanaka et al. |

OTHER PUBLICATIONS

European Search Report for European Patent Application No. 11 846 166.4 dated May 25, 2016.
GenBank: AAV70825. 1, "HT2 [Expression vector pHT2]". Dec. 1, 2004. http://www.ncbi.nlm.nih.gov/protein/AAV70825.1—1 page.
GenBank: ADN27525.1, "HaloTag protein [HaloTag control vector]". Sep. 21, 2010. http://www.ncbi.nlm.nih.gov/protein/ADN27525.1—1 page.
PCT International Search Report and Written Opinion for PCT International Application No. PCT/US2011/063401 dated Sep. 24, 2012.
Anonymous, "Fluorescein sodium—518-47-8—Catalog of Chemical Suppliers", XP055272421, Retrieved from the Internet on May 12, 2016: URL: https://www.chemexper.com/chemicals/supplier/cas/518-47-8+Fluorescein+sodium.html.
Banaszynski, et al., "A rapid, reversible, and tunable method to regulate protein function in living cells using synthetic small molecules", Cell. 126(5), 2006, 995-1004.
Banaszynski, et al., "Chemical control of protein stability and function in living mice", Nat Med. 14(10), 2008, 1123-1127.
Beck, et al., "Fluorophore-assisted light inactivation: a high-throughput tool for direct target validation of proteins", Proteomics. 2(3), 2002, 247-255.
Clackson, et al., "Redesigning an FKBP-ligand interface to generate chemical dimerizers with novel specificity", Proc Natl Acad Sci U S A. 95(18), 1998, 10437-10442.
Dvorin, et al., "A plant-like kinase in Plasmodium falciparum regulates parasite egress from erythrocytes", Science. 328(5980), 2010, 910-912.
Goode, et al., "Identification of promiscuous small molecule activators in high-throughput enzyme activation screens", J Med Chem. 51(8), 2008, 2346-2349.
Herm-Götz, et al., "Rapid control of protein level in the apicomplexan Toxoplasma gondii", Nat Methods. 4(12), 2007, 1003-1005.
Iwamoto, et al., "A general chemical method to regulate protein stability in the mammalian central nervous system", Chem Biol. 17(9), 2010, 981-988.
Kubota, "Quality control against misfolded proteins in the cytosol: a network for cell survival", J Biochem. 146(5), 2009, 609-616.
Los, et al., "HaloTag: a novel protein labeling technology for cell imaging and protein analysis", ACS Chem Biol. 3(6), 2008, 373-382.
Marco Engeler, "Anthracene", XP055272008, Retrieved from the Internet on May 12, 2016: URL: http://www.chemexpercom/searchResult.shtml?format=ccd2013%2Cccd&target=structure&options=brandqtyoffercrm&searchValue=120127&searchTemplate=rn.value%3D%22%3F%22&Search=Search.

(Continued)

Primary Examiner — Suzanne M Noakes
Assistant Examiner — Jae W Lee
(74) Attorney, Agent, or Firm — Saul Ewing Arnstein & Lehr LLP; Kathryn Doyle; Domingos J. Silva

(57) ABSTRACT

The present invention includes compounds that are useful in perturbing or disrupting the function of a transmembrane or intracellular protein, whereby binding of the compounds to the transmembrane or intracellular protein induces proteasomal degradation of the transmembrane or intracellular protein. The present invention further includes a method of inducing proteasomal degradation of a transmembrane or intracellular protein. The present invention further includes a method of identifying or validating a protein of interest as a therapeutic target for treatment of a disease state or condition.

6 Claims, 29 Drawing Sheets
Specification includes a Sequence Listing.

(56) References Cited

OTHER PUBLICATIONS

Neklesa, et al., "Small-molecule hydrophobic tagging-induced degradation of HaloTag fusion proteins", Nat Chem Biol. 7(8), 2011, 538-543.

Nishimura, et al., "An auxin-based degron system for the rapid depletion of proteins in nonplant cells", Nat Methods. 6(12), 2009, 917-922.

Pruett-Miller, et al., "Attenuation of zinc finger nuclease toxicity by small-molecule regulation of protein levels", PLoS Genet. 5(2):e1000376, 2009, 1-11.

Robinson, et al., "Rapid inactivation of proteins by rapamycin-induced rerouting to mitochondria", Dev Cell. 18(2), 2010, 324-331.

Sakamoto, et al., "Protacs: chimeric molecules that target proteins to the Skp1-Cullin-F box complex for ubiquitination and degradation", Proc Natl Acad Sci U S A. 98(15), 2001, 8554-8559.

Schneekloth, et al., "Chemical genetic control of protein levels: selective in vivo targeted degradation", J Am Chem Soc. 126(12), 2004, 3748-3754.

Schrader, et al., "Making it easier to regulate protein stability", Chem Biol. 17(9), 2010, 917-918.

So, et al., "HaloTag Protein-mediated Specific Labeling of Living Cells with Quantum Dots", Biochemical and Biophysical Research Communications, 374(3), 2008, 419-423.

Tae, et al., "Identification of Hydrophobic Tags for the Degradation of Stabilized Proteins", Chembiochem. 13(4), 2012, 538-541.

Tsuzuki, et al., "Adamantane as a brain-directed drug carrier for poorly absorbed drug. 2. AZT derivatives conjugated with the 1-adamantane moiety", J Pharm Sci. 83(4), 1994, 481-484.

Neklesa, et al., Supplementary Information:Small Molecule hydrophobic tagging-induced degradation of HaloTag fusion proteins, Nature Chemical Biology, 2011, 1-49.

FIGURE 5

Table1. Chemical Structures of Representative (Including Tested) HyT compounds

| Code No. | Chemical Structure |
|---|---|
| HyT1 | 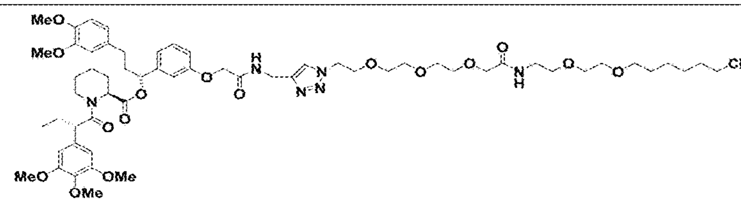 |
| HyT2 | 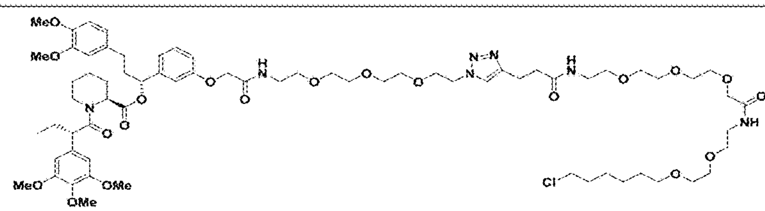 |
| HyT3 | 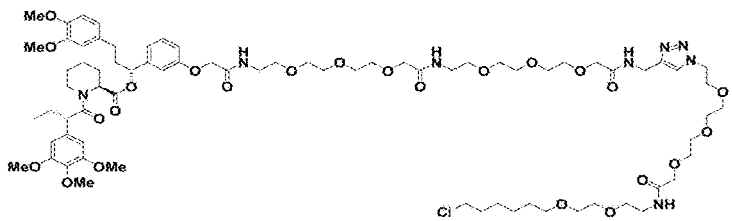 |
| HyT4 | 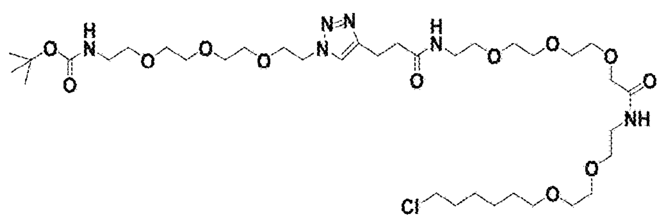 |
| HyT5 (1) | 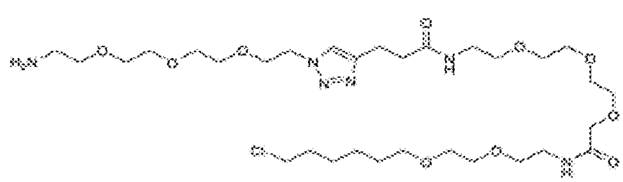 |
| HyT6 (20) | 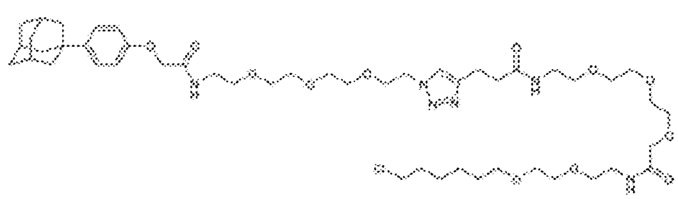 |

| Code No. | Chemical Structure |
|---|---|
| HyT6 | 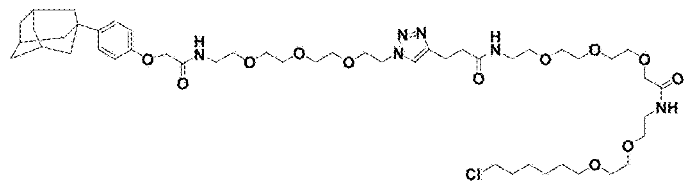 |
| HyT7 | 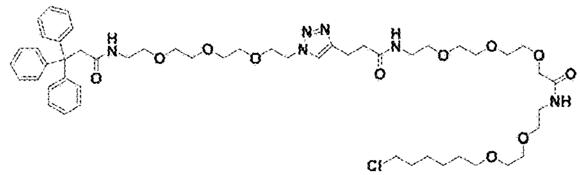 |
| HyT8 (22) | 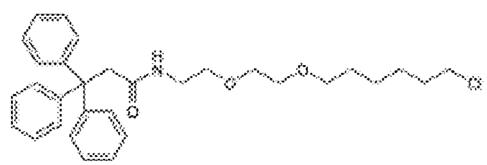 |
| HyT9 (24) | 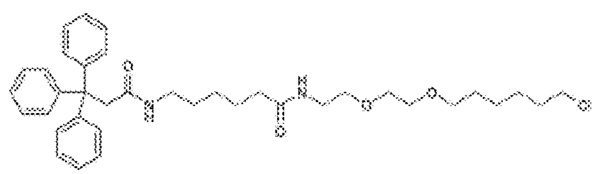 |
| HyT10 (25) | 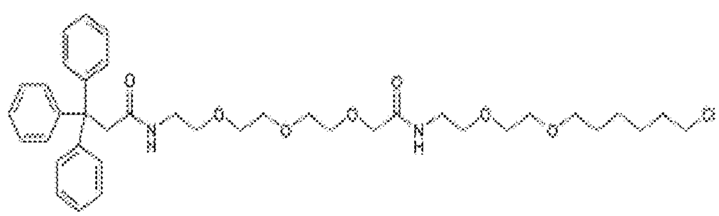 |
| HyT11 (26) | 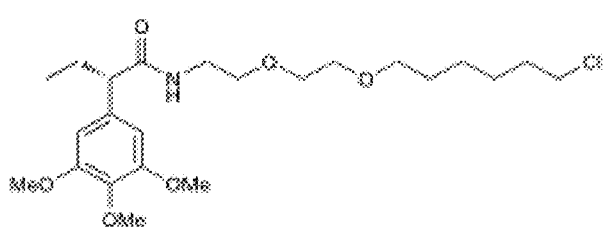 |

| Code No. | Chemical Structure |
|---|---|
| HyT12 (2) | 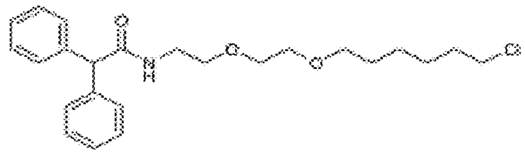 |
| HyT13 (3) | 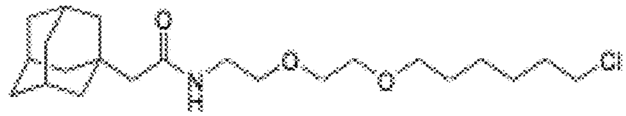 |
| HyT14 (27) | 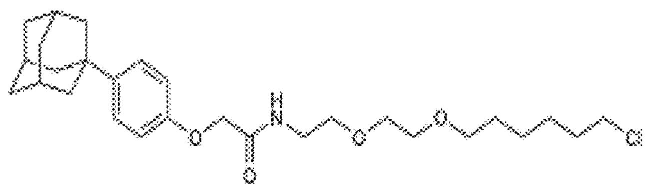 |
| HyT15 (28) | 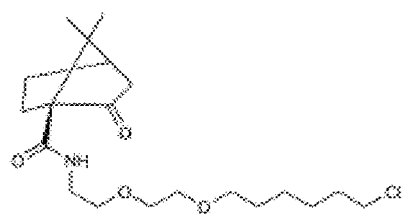 |
| HyT16 (4) | 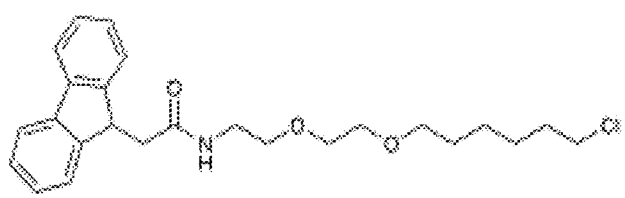 |
| HyT17 (29) | 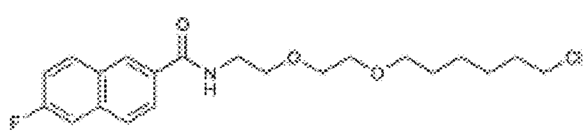 |
| HyT18 (30) | 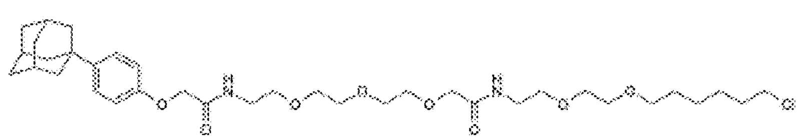 |

| Code No. | Chemical Structure |
|---|---|
| HyT21 (5) | 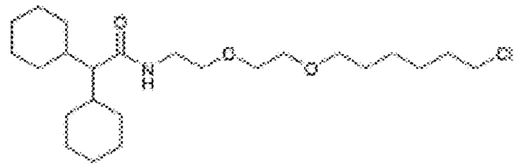 |
| HyT22 (6) | 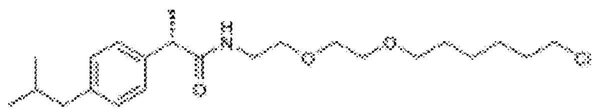 |
| HyT23 (31) | 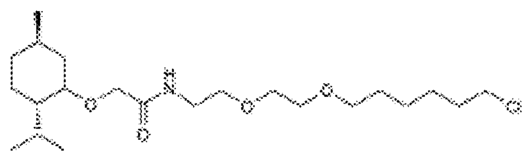 |
| HyT24 (32) | 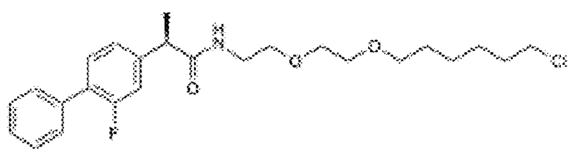 |
| HyT25 (33) | 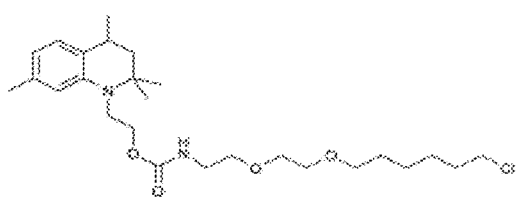 |
| HyT26 (34) | 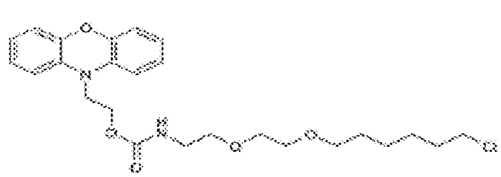 |
| HyT27 (35) | 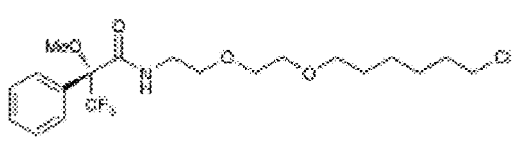 |

| Code No. | Chemical Structure |
|---|---|
| HyT29 (36) | 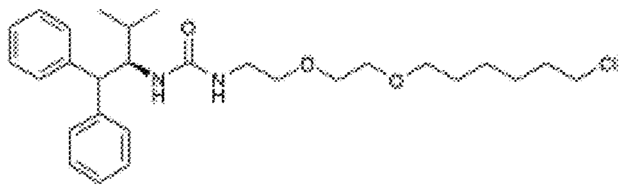 |
| HyT30 (37) | 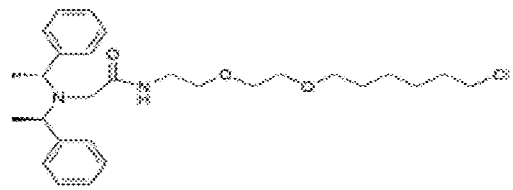 |
| HyT31 (42) | 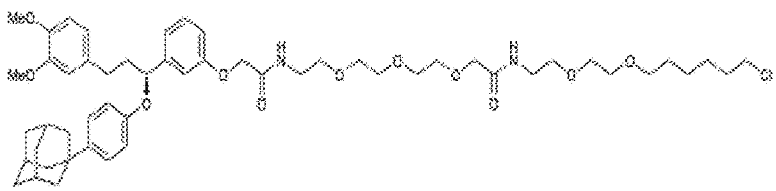 |
| HyT33 (43) | 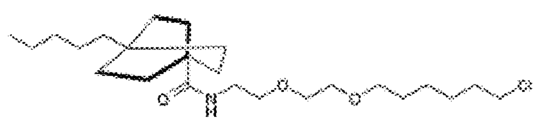 |
| HyT34 (44) | 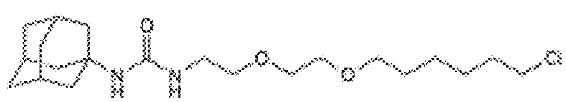 |
| HyT35 (45) | 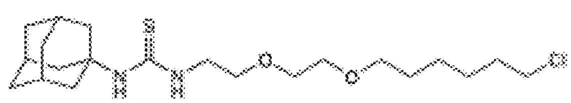 |
| HyT36 (49) | 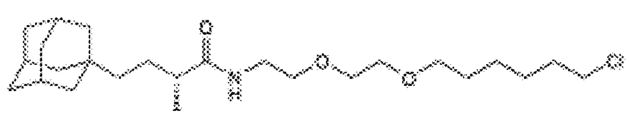 |

| Code No. | Chemical Structure |
|---|---|
| HyT39 | 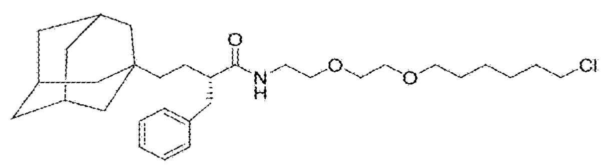 |
| HyT40 (54) | 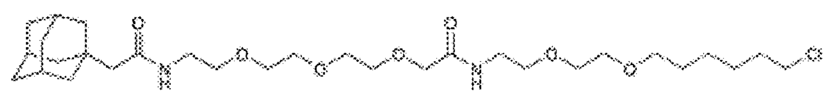 |
| Hyt55 | 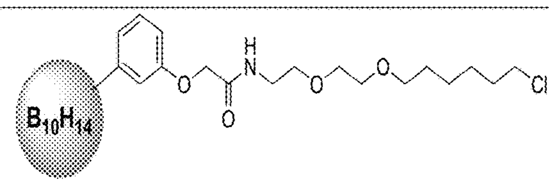 |

12a

12b

HA blot:

actin blot:

Ror2-HA-Halotag

HA blot:      actin blot:

CD3E-HA-HaloTag

HA Blot:      actin blot:

← 115 kDa dimer

← 57.5 kDa monomer

\* - non specific band

CD9-HA-HaloTag

HA blot:      actin blot:

GPR40-HA-HaloTag

HA blot:

← 132 kDa dimer
← 66 kDa monomer actin blot:

Frizzled-4

Short exposure

← HA-HaloTag-FZ4
← actin

Long exposure

← HA-HaloTag-FZ4
← actin

HA-HaloTag-Smad5

Expected MW of HA-HaloTag-Smad5 is 85 kDa. Two smaller bands were consistently observed, presumably due to proteolysis of the full length protein.

HA-HaloTag-HRas(G12V)  HA-HaloTag(D106A)-HRas(G12V)

FIGURE 16

HALOTAG halotag2

SEQ ID. NO:1

MGSEIGTGFPFDPHYVEVLGERMHYVDVGPRDGTPVLFLHGNPTSSYLWRNIIPHVA
PSHRCIAPDLIGMGKSDKPDLDYFFDDHVRYLDAFIEALGLEEVVLVIHDWGSALGF
HWAKRNPERVKGIACMEFIRPIPTWDEWPEFARETFQAFRTADVGRELIIDQNAFIEG
ALPMGVVRPLTEVEMDHYREPFLKPVDREPLWRFPNELPIAGEPANIVALVEAYMN
WLHQSPVPKLLFWGTPGVLIPPAEAARLAESLPNCKTVDIGPGLFLLQEDNPDLIGSEI
ARWLPGLAG

Halotag7

SEQ ID NO:2

MAEIGTGFPFDPHYVEVLGERMHYVDVGPRDGTPVLFLHGNPTSSYVWRNIIPHVAP
THRCIAPDLIGMGKSDKPDLGYFFDDHVRFMDAFIEALGLEEVVLVIHDWGSALGFH
WAKRNPERVKGIAFMEFIRPIPTWDEWPEFARETFQAFRTTDVGRKLIIDQNVFIEGT
LPMGVVRPLTEVEMDHYREPFLNPVDREPLWRFPNELPIAGEPANIVALVEEYMDW
LHQSPVPKLLFWGTPGVLIPPAEAARLAKSLPNCKAVDIGPGLNLLQEDNPDLIGSEIA
RWLSTLEISG

SNAPTAG psnap-tag(m)

SEQ ID NO: 3

MDKDCEMKRTTLDSPLGKLELSGCEQGLHEIKLLGKGTSAADAVEVPAPAAVLGGP
EPLMQATAWLNAYFHQPEAIEEFPVPALHHPVFQQESFTRQVLWKLLKVVKFGEVIS
YQQLAALAGNPAATAAVKTALSGNPVPILIPCHRVVSSSGAVGGYEGGLAVKEWLL
AHEGHRLGKPGLG

FIGURE 16 (Cont'd)

psnap-tag(m)2

SEQ ID NO: 4

MDKDCEMKRTTLDSPLGKLELSGCEQGLHEIKLLGKGTSAADAVEVPAPAAVLGGP
EPLMQATAWLNAYFHQPEAIEEFPVPALHHPVFQQESFTRQVLWKLLKVVKFGEVIS
YQQLAALAGNPAATAAVKTALSGNPVPILIPCHRVVSSSGAVGGYEGGLAVKEWLL
AHEGHRLGKPGLGPAGGSAFKLEVN psnap-tag(T7)

SEQ ID NO: 5

MDKDCEMKRTTLDSPLGKLELSGCEQGLHEIKLLGKGTSAADAVEVPAPAAVLGGP
EPLMQATAWLNAYFHQPEAIEEFPVPALHHPVFQQESFTRQVLWKLLKVVKFGEVIS
YQQLAALAGNPAATAAVKTALSGNPVPILIPCHRVVSSSGAVGGYEGGLAVKEWLL
AHEGHRLGKPGLGPAGIGAPGS psnap-tag(T7)2

SEQ ID NO: 6

MDKDCEMKRTTLDSPLGKLELSGCEQGLHEIKLLGKGTSAADAVEVPAPAAVLGGP
EPLMQATAWLNAYFHQPEAIEEFPVPALHHPVFQQESFTRQVLWKLLKVVKFGEVIS
YQQLAALAGNPAATAAVKTALSGNPVPILIPCHRVVSSSGAVGGYEGGLAVKEWLL
AHEGHRLGKPGLGPAGGSPGLEVN

FIGURE 16 (Cont'd)

CLIPTAG pclip-tag(m)

SEQ ID NO: 7

MDKDCEMKRTTLDSPLGKLELSGCEQGLHEIIFLGKGTSAADAVEVPAPAAVLGGPE
PLIQATAWLNAYFHQPEAIEEFPVPALHHPVFQQESFTRQVLWKLLKVVKFGEVISES
HLAALVGNPAATAAVNTALDGNPVPILIPCHRVVQGDSDVGPYLGGLAVKEWLLAH
EGHRLGKPGLGPAGIGAPGSLE

ACPTAG pACP-tag(m)

SEQ ID NO: 8

MSTIEERVKKIIGEQLGVKQEEVTNNASFVEDLGADSLDTVELVMALEEEFDTEIPDE
EAEKITTVQAAIDYINGHQAPAGIGAPGS pACP-tag(m)-2

SEQ ID NO: 9

MSTIEERVKKIIGEQLGVKQEEVTNNASFVEDLGADSLDTVELVMALEEEFDTEIPDE
EAEKITTVQAAIDYINGHQA

MCPTAG pMCP-tag(m)

SEQ ID NO: 10

MSTIEERVKKIIGEQLGVKQEEVTNNASFVEDLGATSLGTVELVMALEEEFDTEIPDE
EAEKITTVQAAIDYINGHQAPAGIGAPGS

SEQUENCE LISTING

<160> NUMBER OF SEQ ID NOS: 10

<210> SEQ ID NO 1
<211> LENGTH: 296
<212> TYPE: PRT
<213> ORGANISM: Artificial Sequence
<220> FEATURE:
<223> OTHER INFORMATION: HALOTAG halotag2

<400> SEQUENCE: 1

Met Gly Ser Glu Ile Gly Thr Gly Phe Pro Phe Asp Pro His Tyr Val
1               5                   10                  15

Glu Val Leu Gly Glu Arg Met His Tyr Val Asp Val Gly Pro Arg Asp
            20                  25                  30

Gly Thr Pro Val Leu Phe Leu His Gly Asn Pro Thr Ser Ser Tyr Leu
        35                  40                  45

Trp Arg Asn Ile Ile Pro His Val Ala Pro Ser His Arg Cys Ile Ala

```
            50                  55                  60
Pro Asp Leu Ile Gly Met Gly Lys Ser Asp Lys Pro Asp Leu Asp Tyr
 65                  70                  75                  80

Phe Phe Asp Asp His Val Arg Tyr Leu Asp Ala Phe Ile Glu Ala Leu
                 85                  90                  95

Gly Leu Glu Glu Val Val Leu Val Ile His Asp Trp Gly Ser Ala Leu
                100                 105                 110

Gly Phe His Trp Ala Lys Arg Asn Pro Glu Arg Val Lys Gly Ile Ala
                115                 120                 125

Cys Met Glu Phe Ile Arg Pro Ile Pro Thr Trp Asp Glu Trp Pro Glu
            130                 135                 140

Phe Ala Arg Glu Thr Phe Gln Ala Phe Arg Thr Ala Asp Val Gly Arg
145                 150                 155                 160

Glu Leu Ile Ile Asp Gln Asn Ala Phe Ile Glu Gly Ala Leu Pro Met
                165                 170                 175

Gly Val Val Arg Pro Leu Thr Glu Val Glu Met Asp His Tyr Arg Glu
                180                 185                 190

Pro Phe Leu Lys Pro Val Asp Arg Glu Pro Leu Trp Arg Phe Pro Asn
            195                 200                 205

Glu Leu Pro Ile Ala Gly Glu Pro Ala Asn Ile Val Ala Leu Val Glu
210                 215                 220

Ala Tyr Met Asn Trp Leu His Gln Ser Pro Val Pro Lys Leu Leu Phe
225                 230                 235                 240

Trp Gly Thr Pro Gly Val Leu Ile Pro Pro Ala Glu Ala Ala Arg Leu
                245                 250                 255

Ala Glu Ser Leu Pro Asn Cys Lys Thr Val Asp Ile Gly Pro Gly Leu
                260                 265                 270

Phe Leu Leu Gln Glu Asp Asn Pro Asp Leu Ile Gly Ser Glu Ile Ala
            275                 280                 285

Arg Trp Leu Pro Gly Leu Ala Gly
            290                 295

<210> SEQ ID NO 2
<211> LENGTH: 297
<212> TYPE: PRT
<213> ORGANISM: Artificial Sequence
<220> FEATURE:
<223> OTHER INFORMATION: HALOTAG halotag7

<400> SEQUENCE: 2

Met Ala Glu Ile Gly Thr Gly Phe Pro Phe Asp Pro His Tyr Val Glu
 1               5                  10                  15

Val Leu Gly Glu Arg Met His Tyr Val Asp Val Gly Pro Arg Asp Gly
                20                  25                  30

Thr Pro Val Leu Phe Leu His Gly Asn Pro Thr Ser Ser Tyr Val Trp
            35                  40                  45

Arg Asn Ile Ile Pro His Val Ala Pro Thr His Arg Cys Ile Ala Pro
 50                  55                  60

Asp Leu Ile Gly Met Gly Lys Ser Asp Lys Pro Asp Leu Gly Tyr Phe
 65                  70                  75                  80

Phe Asp Asp His Val Arg Phe Met Asp Ala Phe Ile Glu Ala Leu Gly
                 85                  90                  95

Leu Glu Glu Val Val Leu Val Ile His Asp Trp Gly Ser Ala Leu Gly
                100                 105                 110

Phe His Trp Ala Lys Arg Asn Pro Glu Arg Val Lys Gly Ile Ala Phe
```

|  | 115 |  |  | 120 |  |  | 125 |  |  |  |
|---|---|---|---|---|---|---|---|---|---|---|

Met Glu Phe Ile Arg Pro Ile Pro Thr Trp Asp Glu Trp Pro Glu Phe
130                 135                 140

Ala Arg Glu Thr Phe Gln Ala Phe Arg Thr Thr Asp Val Gly Arg Lys
145                 150                 155                 160

Leu Ile Ile Asp Gln Asn Val Phe Ile Glu Gly Thr Leu Pro Met Gly
                165                 170                 175

Val Val Arg Pro Leu Thr Glu Val Glu Met Asp His Tyr Arg Glu Pro
            180                 185                 190

Phe Leu Asn Pro Val Asp Arg Glu Pro Leu Trp Arg Phe Pro Asn Glu
        195                 200                 205

Leu Pro Ile Ala Gly Glu Pro Ala Asn Ile Val Ala Leu Val Glu Glu
    210                 215                 220

Tyr Met Asp Trp Leu His Gln Ser Pro Val Pro Lys Leu Leu Phe Trp
225                 230                 235                 240

Gly Thr Pro Gly Val Leu Ile Pro Pro Ala Glu Ala Ala Arg Leu Ala
                245                 250                 255

Lys Ser Leu Pro Asn Cys Lys Ala Val Asp Ile Gly Pro Gly Leu Asn
            260                 265                 270

Leu Leu Gln Glu Asp Asn Pro Asp Leu Ile Gly Ser Glu Ile Ala Arg
        275                 280                 285

Trp Leu Ser Thr Leu Glu Ile Ser Gly
    290                 295

<210> SEQ ID NO 3
<211> LENGTH: 182
<212> TYPE: PRT
<213> ORGANISM: Artificial Sequence
<220> FEATURE:
<223> OTHER INFORMATION: SNAPTAG psnap-tag(m)

<400> SEQUENCE: 3

Met Asp Lys Asp Cys Glu Met Lys Arg Thr Thr Leu Asp Ser Pro Leu
1               5                   10                  15

Gly Lys Leu Glu Leu Ser Gly Cys Glu Gln Gly Leu His Glu Ile Lys
            20                  25                  30

Leu Leu Gly Lys Gly Thr Ser Ala Ala Asp Ala Val Glu Val Pro Ala
        35                  40                  45

Pro Ala Ala Val Leu Gly Gly Pro Glu Pro Leu Met Gln Ala Thr Ala
    50                  55                  60

Trp Leu Asn Ala Tyr Phe His Gln Pro Glu Ala Ile Glu Glu Phe Pro
65                  70                  75                  80

Val Pro Ala Leu His His Pro Val Phe Gln Gln Glu Ser Phe Thr Arg
                85                  90                  95

Gln Val Leu Trp Lys Leu Leu Lys Val Val Lys Phe Gly Glu Val Ile
            100                 105                 110

Ser Tyr Gln Gln Leu Ala Ala Leu Ala Gly Asn Pro Ala Ala Thr Ala
        115                 120                 125

Ala Val Lys Thr Ala Leu Ser Gly Asn Pro Val Pro Ile Leu Ile Pro
    130                 135                 140

Cys His Arg Val Val Ser Ser Gly Ala Val Gly Gly Tyr Glu Gly
145                 150                 155                 160

Gly Leu Ala Val Lys Glu Trp Leu Leu Ala His Glu Gly His Arg Leu
                165                 170                 175

Gly Lys Pro Gly Leu Gly

<210> SEQ ID NO 4
<211> LENGTH: 194
<212> TYPE: PRT
<213> ORGANISM: Artificial Sequence
<220> FEATURE:
<223> OTHER INFORMATION: SNAPTAG psnap-tag(m)2

<400> SEQUENCE: 4

```
Met Asp Lys Asp Cys Glu Met Lys Arg Thr Thr Leu Asp Ser Pro Leu
1               5                   10                  15
Gly Lys Leu Glu Leu Ser Gly Cys Glu Gln Gly Leu His Glu Ile Lys
            20                  25                  30
Leu Leu Gly Lys Gly Thr Ser Ala Ala Asp Ala Val Glu Val Pro Ala
        35                  40                  45
Pro Ala Ala Val Leu Gly Gly Pro Glu Pro Leu Met Gln Ala Thr Ala
    50                  55                  60
Trp Leu Asn Ala Tyr Phe His Gln Pro Glu Ala Ile Glu Glu Phe Pro
65                  70                  75                  80
Val Pro Ala Leu His His Pro Val Phe Gln Gln Glu Ser Phe Thr Arg
                85                  90                  95
Gln Val Leu Trp Lys Leu Leu Lys Val Val Lys Phe Gly Glu Val Ile
            100                 105                 110
Ser Tyr Gln Gln Leu Ala Ala Leu Ala Gly Asn Pro Ala Ala Thr Ala
        115                 120                 125
Ala Val Lys Thr Ala Leu Ser Gly Asn Pro Val Pro Ile Leu Ile Pro
    130                 135                 140
Cys His Arg Val Val Ser Ser Gly Ala Val Gly Gly Tyr Glu Gly
145                 150                 155                 160
Gly Leu Ala Val Lys Glu Trp Leu Leu Ala His Glu Gly His Arg Leu
                165                 170                 175
Gly Lys Pro Gly Leu Gly Pro Ala Gly Gly Ser Ala Phe Lys Leu Glu
            180                 185                 190
Val Asn
```

<210> SEQ ID NO 5
<211> LENGTH: 191
<212> TYPE: PRT
<213> ORGANISM: Artificial Sequence
<220> FEATURE:
<223> OTHER INFORMATION: SNAPTAG psnap-tag(T7)

<400> SEQUENCE: 5

```
Met Asp Lys Asp Cys Glu Met Lys Arg Thr Thr Leu Asp Ser Pro Leu
1               5                   10                  15
Gly Lys Leu Glu Leu Ser Gly Cys Glu Gln Gly Leu His Glu Ile Lys
            20                  25                  30
Leu Leu Gly Lys Gly Thr Ser Ala Ala Asp Ala Val Glu Val Pro Ala
        35                  40                  45
Pro Ala Ala Val Leu Gly Gly Pro Glu Pro Leu Met Gln Ala Thr Ala
    50                  55                  60
Trp Leu Asn Ala Tyr Phe His Gln Pro Glu Ala Ile Glu Glu Phe Pro
65                  70                  75                  80
Val Pro Ala Leu His His Pro Val Phe Gln Gln Glu Ser Phe Thr Arg
                85                  90                  95
Gln Val Leu Trp Lys Leu Leu Lys Val Val Lys Phe Gly Glu Val Ile
```

```
                100             105              110
Ser Tyr Gln Gln Leu Ala Ala Leu Ala Gly Asn Pro Ala Ala Thr Ala
            115                 120                 125

Ala Val Lys Thr Ala Leu Ser Gly Asn Pro Val Pro Ile Leu Ile Pro
        130                 135                 140

Cys His Arg Val Val Ser Ser Gly Ala Val Gly Gly Tyr Glu Gly
145                 150                 155                 160

Gly Leu Ala Val Lys Glu Trp Leu Leu Ala His Glu Gly His Arg Leu
                165                 170                 175

Gly Lys Pro Gly Leu Gly Pro Ala Gly Ile Gly Ala Pro Gly Ser
            180                 185                 190
```

<210> SEQ ID NO 6
<211> LENGTH: 193
<212> TYPE: PRT
<213> ORGANISM: Artificial Sequence
<220> FEATURE:
<223> OTHER INFORMATION: SNAPTAG psnap-tag(T7)2

<400> SEQUENCE: 6

```
Met Asp Lys Asp Cys Glu Met Lys Arg Thr Thr Leu Asp Ser Pro Leu
1               5                   10                  15

Gly Lys Leu Glu Leu Ser Gly Cys Glu Gln Gly Leu His Glu Ile Lys
            20                  25                  30

Leu Leu Gly Lys Gly Thr Ser Ala Ala Asp Ala Val Glu Val Pro Ala
        35                  40                  45

Pro Ala Ala Val Leu Gly Gly Pro Glu Pro Leu Met Gln Ala Thr Ala
    50                  55                  60

Trp Leu Asn Ala Tyr Phe His Gln Pro Glu Ala Ile Glu Glu Phe Pro
65                  70                  75                  80

Val Pro Ala Leu His His Pro Val Phe Gln Gln Glu Ser Phe Thr Arg
                85                  90                  95

Gln Val Leu Trp Lys Leu Leu Lys Val Val Lys Phe Gly Glu Val Ile
            100                 105                 110

Ser Tyr Gln Gln Leu Ala Ala Leu Ala Gly Asn Pro Ala Ala Thr Ala
        115                 120                 125

Ala Val Lys Thr Ala Leu Ser Gly Asn Pro Val Pro Ile Leu Ile Pro
    130                 135                 140

Cys His Arg Val Val Ser Ser Gly Ala Val Gly Gly Tyr Glu Gly
145                 150                 155                 160

Gly Leu Ala Val Lys Glu Trp Leu Leu Ala His Glu Gly His Arg Leu
                165                 170                 175

Gly Lys Pro Gly Leu Gly Pro Ala Gly Gly Ser Pro Gly Leu Glu Val
            180                 185                 190

Asn
```

<210> SEQ ID NO 7
<211> LENGTH: 193
<212> TYPE: PRT
<213> ORGANISM: Artificial Sequence
<220> FEATURE:
<223> OTHER INFORMATION: CLIPTAG pclip-tag(m)

<400> SEQUENCE: 7

```
Met Asp Lys Asp Cys Glu Met Lys Arg Thr Thr Leu Asp Ser Pro Leu
1               5                   10                  15

Gly Lys Leu Glu Leu Ser Gly Cys Glu Gln Gly Leu His Glu Ile Ile
```

```
                    20                  25                  30

Phe Leu Gly Lys Gly Thr Ser Ala Ala Asp Ala Val Glu Val Pro Ala
            35                  40                  45

Pro Ala Val Leu Gly Gly Pro Glu Pro Leu Ile Gln Ala Thr Ala
 50                  55                  60

Trp Leu Asn Ala Tyr Phe His Gln Pro Glu Ala Ile Glu Glu Phe Pro
 65                  70                  75                  80

Val Pro Ala Leu His His Pro Val Phe Gln Gln Glu Ser Phe Thr Arg
                85                  90                  95

Gln Val Leu Trp Lys Leu Leu Lys Val Val Lys Phe Gly Glu Val Ile
            100                 105                 110

Ser Glu Ser His Leu Ala Ala Leu Val Gly Asn Pro Ala Ala Thr Ala
            115                 120                 125

Ala Val Asn Thr Ala Leu Asp Gly Asn Pro Val Pro Ile Leu Ile Pro
        130                 135                 140

Cys His Arg Val Val Gln Gly Asp Ser Asp Val Gly Pro Tyr Leu Gly
145                 150                 155                 160

Gly Leu Ala Val Lys Glu Trp Leu Leu Ala His Glu Gly His Arg Leu
                165                 170                 175

Gly Lys Pro Gly Leu Gly Pro Ala Gly Ile Gly Ala Pro Gly Ser Leu
            180                 185                 190

Glu

<210> SEQ ID NO 8
<211> LENGTH: 88
<212> TYPE: PRT
<213> ORGANISM: Artificial Sequence
<220> FEATURE:
<223> OTHER INFORMATION: ACPTAG pACP-tag(m)

<400> SEQUENCE: 8

Met Ser Thr Ile Glu Glu Arg Val Lys Lys Ile Ile Gly Glu Gln Leu
1               5                   10                  15

Gly Val Lys Gln Glu Glu Val Thr Asn Asn Ala Ser Phe Val Glu Asp
            20                  25                  30

Leu Gly Ala Asp Ser Leu Asp Thr Val Glu Leu Val Met Ala Leu Glu
        35                  40                  45

Glu Glu Phe Asp Thr Glu Ile Pro Asp Glu Glu Ala Glu Lys Ile Thr
    50                  55                  60

Thr Val Gln Ala Ala Ile Asp Tyr Ile Asn Gly Ile Ile Gln Ala Pro
65                  70                  75                  80

Ala Gly Ile Gly Ala Pro Gly Ser
                85

<210> SEQ ID NO 9
<211> LENGTH: 78
<212> TYPE: PRT
<213> ORGANISM: Artificial Sequence
<220> FEATURE:
<223> OTHER INFORMATION: ACPTAG pACP-tag(m)-2

<400> SEQUENCE: 9

Met Ser Thr Ile Glu Glu Arg Val Lys Lys Ile Ile Gly Glu Gln Leu
1               5                   10                  15

Gly Val Lys Gln Glu Glu Val Thr Asn Asn Ala Ser Phe Val Glu Asp
            20                  25                  30

Leu Gly Ala Asp Ser Leu Asp Thr Val Glu Leu Val Met Ala Leu Glu
```

```
                    35                  40                  45
Glu Glu Phe Asp Thr Glu Ile Pro Asp Glu Glu Ala Glu Lys Ile Thr
    50                  55                  60

Thr Val Gln Ala Ala Ile Asp Tyr Ile Asn Gly His Gln Ala
65                  70                  75

<210> SEQ ID NO 10
<211> LENGTH: 87
<212> TYPE: PRT
<213> ORGANISM: Artificial Sequence
<220> FEATURE:
<223> OTHER INFORMATION: MCPTAG pMCP-tag(m)

<400> SEQUENCE: 10

Met Ser Thr Ile Glu Glu Arg Val Lys Lys Ile Ile Gly Glu Gln Leu
1               5                   10                  15

Gly Val Lys Gln Glu Glu Val Thr Asn Asn Ala Ser Phe Val Glu Asp
                20                  25                  30

Leu Gly Ala Thr Ser Leu Gly Thr Val Glu Leu Val Met Ala Leu Glu
            35                  40                  45

Glu Glu Phe Asp Thr Glu Ile Pro Asp Glu Glu Ala Glu Lys Ile Thr
    50                  55                  60

Thr Val Gln Ala Ala Ile Asp Tyr Ile Asn Gly His Gln Ala Pro Ala
65                  70                  75                  80

Gly Ile Gly Ala Pro Gly Ser
                85
```

SMALL-MOLECULE HYDROPHOBIC TAGGING OF FUSION PROTEINS AND INDUCED DEGRADATION OF SAME

CROSS-REFERENCE TO RELATED APPLICATIONS

The present application is a divisional of, and claims priority to, U.S. patent application Ser. No. 15/343,640, filed Nov. 4, 2016, issued as U.S. Pat. No. 9,632,089, which is a divisional of, and claims priority to, U.S. patent application Ser. No. 13/992,076, filed Jun. 27, 2014, issued as U.S. Pat. No. 9,500,653, which is a 35 U.S.C. § 371 national phase application of, and claims priority to, International Application No. PCT/US2011/063401, filed Dec. 6, 2011, which claims priority under 35 U.S.C. § 119(e) to U.S. Provisional Applications No. 61/420,584, filed Dec. 7, 2010, and No. 61/530,014, filed Sep. 1, 2011, all of which applications are hereby incorporated by reference in their entireties herein.

STATEMENT REGARDING FEDERALLY SPONSORED RESEARCH OR DEVELOPMENT

This invention was made with government support under grant no. R01AI084140 awarded by National Institutes of Health (NIH). The government has certain rights in the invention.

FIELD OF THE INVENTION

The present invention relates to compounds and compositions which may be used to perturb and/or disrupt the function of a transmembrane or intracellular protein in order to identify or validate that protein as a protein of interest. In addition to compounds and methods, the present invention is also directed to a method of identifying or validating a protein as a protein of interest for use as a bioactive agent (drug) target for therapy of a disease state or condition.

BACKGROUND OF THE INVENTION

One of the central challenges of chemical biology remains the ability to perturb the function of any intracellular protein using a small molecule. While significant strides have been made towards developing individual ligands to specific proteins, only approximately 300 molecular targets for approved drugs have been characterized[1]. Furthermore, the fraction of the proteome classified as "undruggable" by current methods is estimated to be about 80%[2]. It is likely that many appealing drug candidates have yet to be found and that future advances in drug development will be able to overcome the boundaries of what is thought to be an "undruggable" target[3,4]. Therefore, the challenge for biologists remains to identify those disease-causing drug targets. To this end, advances in deep sequencing, microarray technology and genome-wide RNAi screens have been employed successfully to identify promising new drug targets. For instance, genome-wide RNAi screens have been employed to identify synthetic lethal interactions with mutated oncogenes and to identify genes necessary for various pathogenic infections[5-7].

While target identification is an obvious important first step in drug development, the in vivo validation of these potential targets remains a challenge. This is due in part to the unpredictable pharmacokinetics/pharmacodynamics of any inhibitory compound identified based on in vitro inhibition of protein function. In other words, is the failure of a small molecule inhibitor to give the desired in vivo result an unforeseen consequence of its in vivo metabolism or is its target protein simply a poor drug target? To address this question, general methods are needed to functionally validate whether modulation of a putative disease-relevant protein leads to the desired in vivo result. RNAi offered initial promise for organismal validation of putative drug targets, however, the delivery and stability of duplex RNA remain major hurdles in knocking down mRNA expression in a whole animal setting[8]. In the absence of a direct ligand for the target protein, there are currently three categories of small molecule-based methods to control the function of a protein of interest (POI)[9]. First, the plant hormone auxin can be employed to dimerize a plant E3 ubiquitin ligase (TIR1) with a domain from the AUX/IAA transcriptional repressor (Aid1), which when fused to a POI can be ubiquitinated by proximity to TIR1[10]. This method requires fusing the POI to Aid1, along with an introduction of the plant E3 ligase TIR1 into cells. A second general method used to deregulate protein function involves dimerization of FKBP12 and the FKBP12-rapamycin binding (FRB) domain from mTOR. It has been shown that a POI can be recruited to the proteasome or to the mitochondrial outer membrane by this method[11-13]. Again, at least two fusion proteins must be introduced into the cell for this system to function[9]. Lastly, two destabilizing domains (DDs), one based on the FKBP12 protein and the other on E. coli DHFR protein[14,15], have been developed to destabilize a DD-POI fusion protein. The degradation conferring DD can be stabilized by inclusion of derivatives of FK506[16] (in the case of mutagenized FKBP12) or the E. coli DHFR inhibitor trimethoprim (in the case of DHFR), ultimately leading to increased levels of the fusion protein. While the DD method has been successfully used in several studies[17-20], it requires the continued presence of the ligand for stable expression of the fusion protein. This requirement can be a concern when studying developing embryos, which might not receive sufficient stabilizing ligand, or when studying the long term effects of a POI, in which case the ligand would have to be injected into an animal for the duration of the study. Also, in the case of the long-term expression of the POI, one must bear in mind the possible fluctuations of the POI levels that are due to the intermittent injections of the stabilizing ligand.

BRIEF DESCRIPTION OF THE INVENTION

The present invention is directed to a hydrophobic compound comprising a hydrophobic moiety linked to a reactive linker, preferably a haloalkane reactive linker (i.e., a linker which contains a haloalkane moiety which is reactive with a halogenase/hydrolase self-labeling tag, such as halotag) which forms a covalent bond with the fusion protein linking the hydrophobic compound to the fusion protein. Compounds according to the present invention are useful for binding a fusion protein wherein the fusion protein comprises a protein of interest (e.g., a potential drug or other physiological target) and a self-labeling tag (such as a halotag, snaptag, cliptag, ACPtag, MCPtag, among others) which is useful for binding the hydrophobic compound to the fusion protein. In preferred aspects of the invention the hydrophobic compound comprises a haloalkane reactive linker to which the hydrophobic moiety may be linked to the fusion protein through action of a halogenase self-labeling tag (e.g. HaloTag) on the haloalkane reactive linker. Once reacted, the hydrophobic moiety is covalently bonded to the fusion protein. It has been unexpectedly discovered that the hydrophobic moiety covalently linked to the fusion protein produces degradation of the fusion protein (through interaction/degradation with the protein of interest) resulting in a denaturation of the protein and proteasomal degradation of the fusion protein. The action of the hydrophobic moiety linked to the fusion protein in degrading the fusion protein may be used in assays to determine the importance of the protein of interest to a biological process, for example, the modulation of a disease state or condition such as the growth or inhibition of a cancer cell or tissue. Determining the importance of the protein of interest may be used to establish the protein of interest as a potential target of bioactive agents, including small molecule pharmaceutical agents for the treatment of a disease state or condition which is modulated by the protein of interest.

In a method according to the present invention to determine if a protein of interest is a potential bioactive agent (e.g. drug) target, a hydrophobically labeled fusion protein comprising a protein of interest is exposed to cells and the impact of the degradation of the hydrophobically labeled fusion protein in or on the surface of the cells is measured to determine if the protein of interest is a potential drug target (i.e., modulates a disease or condition for which drug or other therapy may prove useful). In preferred embodiments, this method comprises covalently attaching a fusion protein comprising a protein of interest and a self-labeling polypeptide to a hydrophobic moiety This can be achieved by expressing the two polypeptides as a fusion protein.

In a first method aspect, the present invention comprises the steps of:
1. Providing a hydrophobically labeled fusion protein wherein said fusion protein comprises a protein of interest and a hydrophobic moiety covalently linked to said fusion protein wherein said hydrophobic moiety is capable of degrading said fusion protein intracellularly or on the surface of cells;
2. Exposing cells which utilize said protein of interest to said hydrophobically labeled fusion protein (e.g. by intracellular expression of the fusion protein or by exposure of the cells to the fusion protein), wherein the fusion protein may be optionally and preferably labeled with the hydrophobic moiety within or on the surface of said cells by a small molecule that labels self-labeling polypeptide of the fusion protein with a hydrophobic moiety;
3. Measuring the degradation of the fusion protein in or the surface of the cells; and
4. Determining if the degradation of the fusion protein modulates the biological activity of the cells through a change in a phenotypic response of the cells (e.g., a change in the growth and/or activity of the cells which is identified) consistent with the protein being a potential target for a bioactive agent (e.g. drug) for a disease and/or condition modulated through said protein of interest.

In preferred aspects, the method according to the present invention utilizes a fusion protein comprising a protein of interest and a self-labeling polypeptide to hydrophobically label the fusion protein to determine if the protein of interest is a potential bioactive agent (e.g. drug) target. This method comprises the steps of:
1. Providing a fusion protein comprising a protein of interest and a polypeptide self-labeling tag in vitro or in vivo, including intracellularly or on the surface of cells;
2. Covalently linking said fusion protein to a compound comprising a hydrophobic group (preferably, other than a fluorescent moiety having a Clog P of at least about 1.5) and a reactive linker, wherein the reactive linker is a substrate for the self-labeling tag which wherein said hydrophobic group is covalently linked to said fusion protein, thus producing a hydrophobically labeled fusion protein;
3. Optionally, isolating said hydrophobically labeled fusion protein;
4. Exposing cells which utilize said protein of interest to said hydrophobically labeled fusion protein;
5. Measuring the degradation of said fusion protein in or on the surface of said cells; and optionally
6. Determining if said degradation of said fusion protein modulates biological activity of said cells (through a change in a phenotypic response of the cells, e.g., a change in the growth and/or activity of the cells which is identified) consistent with the protein being a potential target for a bioactive agent (e.g. drug) for a disease and/or condition modulated through said protein of interest.

In alternative aspects of the invention, the present invention is directed to a method of inducing degradation of a fusion protein in a cell, the method comprising the steps of
1. expressing a fusion protein in a cell wherein said fusion protein comprises a protein of interest and a self-labeling polypeptide tag;
2. reacting intracellularly or on the surface of said cell said expressed fusion protein with a compound comprising a hydrophobic group and a group reactive with said self-labeling polypeptide tag, wherein said compound upon reaction with said self-labeling polypeptide tag forms a covalent bond with said fusion protein to form a hydrophobically labeled fusion protein; and
3. allowing said fusion protein to degrade in or on the surface of said cell.

In preferred aspects of the invention, the fusion protein is produced and hydrophobic labeling of the fusion protein occurs in or on the surface of the same cells in which the protein of interest is utilized so that determination of the relevance of the protein of interest occurs in the same cells in which fusion protein is produced and the produced fusion protein is hydrophobically labeled. Thus, in certain preferred aspects of the invention the fusion protein is covalently linked to the hydrophobic moiety through the reactive linker in vivo/intracellularly or on the surface of cells by expressing the fusion protein intracellularly (including in test animals, such as a mouse, rat or other mammal) and exposing the fusion protein to a compound comprising the hydrophobic moiety and reactive linker (e.g., the compound may be administered in vivo to the test animal or exposed to the cells growing in medium), wherein the hydrophobic moiety linked to the fusion protein will cause the fusion protein to degrade intracellularly or on the surface of cells with a possible resulting and measurable phenyotypic response consistent with the the protein of interest being a potentially important drug target. It is noted that fusion proteins may be produced intracellularly and anchored on the surface of a cell through the use of signal and/or anchor peptide sequences which are native to a cell or expressed with the fusion protein. Such an approach is well known in the art and allows a fusion protein to be expressed and anchored on a cellular surface for attachment of a hydrophobic moiety. It is contemplated that the present invention is applicable to proteins which function on the surface of cells, as well as proteins which function internally in cells.

In the present invention, the fusion protein comprises a protein of interest and a polypeptide self-labeling tag (e.g. a Halotag, a Snaptag, a Cliptag, a ACP tag or a MCP tag) to which the hydrophobic moiety can be bound through a reactive linker. In the case of the Halotag fusion protein, the reactive linker contains a haloalkane group which reacts with the halogenase of the Halotag to produce a covalent bond with the fusion protein. In the case of a Snaptag fusion protein, the reactive linker contains a benzyl guanine substrate which reacts with the the DNA repair protein $O^6$-alkylguanine-DNA alkyltransferase to afford a covalently linked hydrophobic moiety on the fusion protein. In the case of a Cliptag fusion protein, the reactive linker contains a O2-benzylcytosine moiety in order to afford the covalently linked hydrophobic moiety on the fusion protein. In the case of a ACP tag, the reactive linker contains a coenzyme A derivative (CoA derivative) which is covalently bonded through a post-translational modification catalyzed by the acyl carrier protein (ACP) phosphopantetheinyl transferase AcpS (ACP synthase). In the case of a MCP tag (mutant), the reactive linker contains a coenzyme A derivative which is covalently bonded through a post-translational modification catalyzed by a phosphopantetheinyl transferase Sfp (SFP synthase), but not AcpS. It is noted that the ACP and MCP tags are useful for providing hydrophobically labeled fusion proteins which are unable to penetrate cells-they are limited in their use to proteins of interest which are surface proteins.

In the above-described in the measuring step, degraded protein may be quantified by measuring non-degraded or degraded fusion protein in or on the surface of said cells using standard methods for identifying and quantifying proteins. These methods include, inter alia, using protein specific antibodies linked to a reporter, such as a fluorescent or other reporter, such methods including immunoassay (e.g. ELISA, among others) and immunoblot, absorbance assays, mass spectrometric methods and proteomics methods, among numerous others. Methods for quantifying specific proteins in samples are well known in the art and are readily adapted to methods according to the present invention. Assaying for degraded protein and the impact of such degradation on the function of a cell, for example, the growth and/or proliferation of the cell (e.g., cell death) or other characteristic (e.g. biological, physiological) of a cell evidences the importance of the protein of interest to cellular growth and function and establishes whether the protein of interest is a modulator of a disease state or condition and thus a potential target (bioactive agent, including drugs) for the treatment of said disease state or condition. Identifying a protein of interest as a pharmaceutical target will allow the development of assays to identify compounds and other bioactive agents exhibiting activity as potential inhibitors and/or agonists of the protein of interest.

In one aspect, compounds according to the present invention may be represented by the general formula:

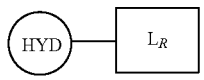

Where

is a hydrophobic group other than a reporter group (e.g. a fluorescent group) having a ClogP of at least about 1.5 or as specifically as otherwise described herein; and

is a linker group having a reactive moiety which reacts with a self-labeling polypeptide tag of a fusion protein comprising said self-labeling tag and a protein of interest to form a covalent link between said

group and said fusion protein, wherein said hydrophobic group promotes the degradation of said protein of interest in said fusion protein covalently linked to said

group.

In alternative embodiments according to the present invention, a compound according to the present invention comprises a compound according to the chemical structure:

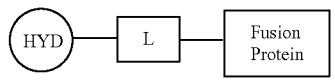

Where

is a hydrophobic group other than a fluorescent moiety having a ClogP of at least about 1.5 or as otherwise specifically described herein;

is a fusion protein comprising a protein of interest and a self-labeling polypeptide tag linked to said protein of interest in said fusion protein, said enzyme tag covalently linking said

group to said fusion protein; and
L is a chemical linker which covalently binds said

group to said fusion protein, wherein said hydrophobic group promotes the degradation of said protein of interest comprising a protein of interest covalently linked to said

group.

In preferred aspects of the invention,

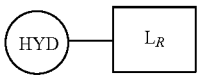

compounds which may be used to covalently bind a hydrophobic moiety to a fusion protein, which preferably contains a self-labeling tag protein, have the chemical structure:

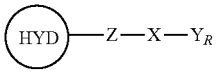

Where

is a hydrophobic group as otherwise described herein;
Z is a group which links

to X;
X is a group linking Z to group $Y_R$; and
$Y_R$ is a group which is reactive with the fusion protein, preferably a self-labeling tag on said fusion protein, which forms a covalent bond connecting the hydrophobic group and the fusion protein.

In preferred aspects, Z is absent (a bond), $-(CH_2)_i-O-$, $-(CH_2)_i-S-$, $-(CH_2)_i-N-R$, a $(CH_2)_i-X_1Y_1$ group wherein $X_1Y_1$ forms an amide group, or a urethane group, ester or thioester group, or a

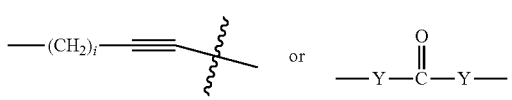

group
Each R is H, or a $C_1$-$C_3$ alkyl or alkanol group;
Each Y is independently a bond, O, S or N—R;
and each i is independently 0 to 100, 1 to 75, 1 to 60, 1 to 55, 1 to 50, 1 to 45, 1 to 40, 2 to 35, 3 to 30, 1 to 15, 1 to 10, 1 to 8, 1 to 6, 1, 2, 3, 4 or 5;

In preferred aspects X is a

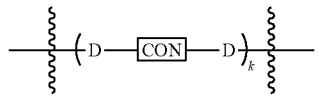

group
Where each D is independently a bond (absent),

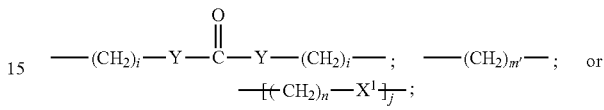

j is 1 to 100, 1 to 75, 1 to 60, 1 to 55, 1 to 50, 1 to 45, 1 to 40, 2 to 35, 3 to 30, 1 to 15, 1 to 10, 1 to 8, 1 to 6, 1, 2, 3, 4 or 5;
k is 1 to 100, 1 to 75, 1 to 60, 1 to 55, 1 to 50, 1 to 45, 1 to 40, 2 to 35, 3 to 30, 1 to 15, 1 to 10, 1 to 8, 1 to 6, 1, 2, 3, 4 or 5; preferably k is 1, 2, 3, 4, or 5;
m' is 1 to 100, 1 to 75, 1 to 60, 1 to 55, 1 to 50, 1 to 45, 1 to 40, 2 to 35, 3 to 30, 1 to 15, 1 to 10, 1 to 8, 1 to 6, 1, 2, 3, 4 or 5;
n is 1 to 100, 1 to 75, 1 to 60, 1 to 55, 1 to 50, 1 to 45, 1 to 40, 2 to 35, 3 to 30, 1 to 15, 1 to 10, 1 to 8, 1 to 6, 1, 2, 3, 4 or 5;
$X^1$ is O, S or N—R, preferably O;
Y is the same as above; and

is a bond (absent) or a

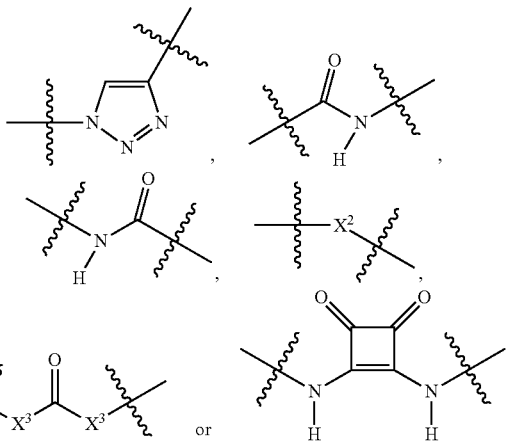

group,
Where $X^2$ is O, S, $NR^4$, S(O), $S(O)_2$, $-S(O)_2O-$, $-OS(O)_2$, or $OS(O)_2O$;
$X^3$ is O, S, $NR^4$; and
$R^4$ is H or a $C_1$-$C_3$ alkyl group, or
a pharmaceutically acceptable salt, enantiomer or stereoisomer thereof.

Preferably,

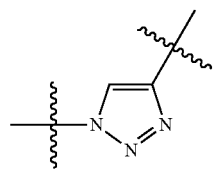 [SMILES: *c1cn(*)nn1]

is a group or an amide group.

In preferred aspects, $Y_R$ is a group which is reactive with a self-labeling tag of the fusion protein, wherein the self-labeling tag is preferably a Halotag, a Snaptag, a Cliptag, a ACPtag or a MCPtag. Preferably, the self-labeling tag is a Halotag, and the reactive substrate for the Halotag is a haloalkane group which is optionally substituted with one or two ether groups, preferably a $C_2$-$C_{12}$ chloralkyl group which is optionally substituted with one (monoether) or two (diether) ether groups, even more preferably, a haloalkyl diether group. In preferred aspects the haloalkyl diether group is according to the chemical structure:

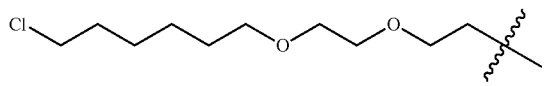 [SMILES: *CCOCCOCCCCCCCl]

and forms a chemical structure with hydrophobic group and remaining portion of the linker according to the chemical structure:

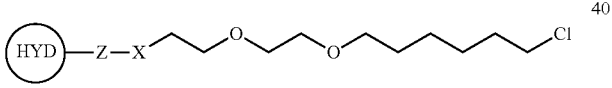

Where (HYD),

Z and X are as otherwise described above.

In alternative embodiments, where the fusion protein comprises a self-labeling tag as a Snaptag, $Y_R$ is a benzyl-guanine group

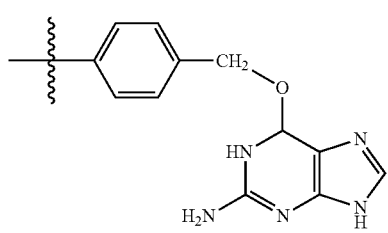 [SMILES: *c1ccc(COC2NC(N)=Nc3[nH]cnc32)cc1]

which provides a compound according to the chemical structure:

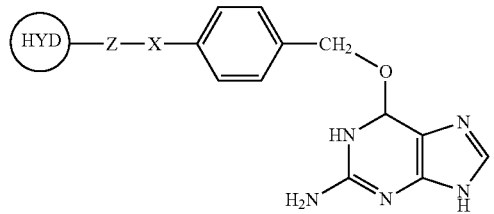

Where (HYD),

Z and X are as otherwise described above.

In alternative embodiments where the fusion protein comprises a self-labeling tag as a Cliptag, $Y_R$ is a benzyl-cytosine group

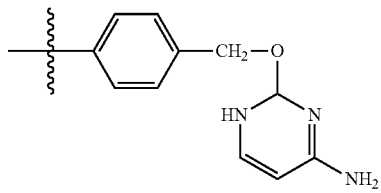 [SMILES: *c1ccc(COC2N=C(N)C=CN2)cc1]

which forms a compound according to the chemical structure:

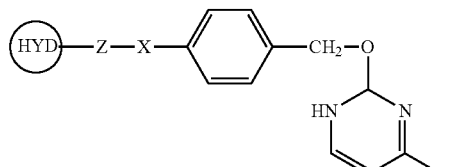

Where (HYD),

Z and X are as otherwise described above.

In further alternative embodiments, where the fusion protein comprises a self-labeling tag as a ACPtag or a MCPtag, $Y_R$ is a coenzyme A derivative

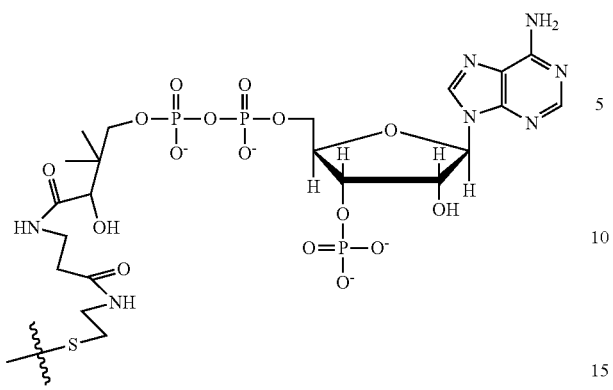

which forms a compound according to the chemical structure:

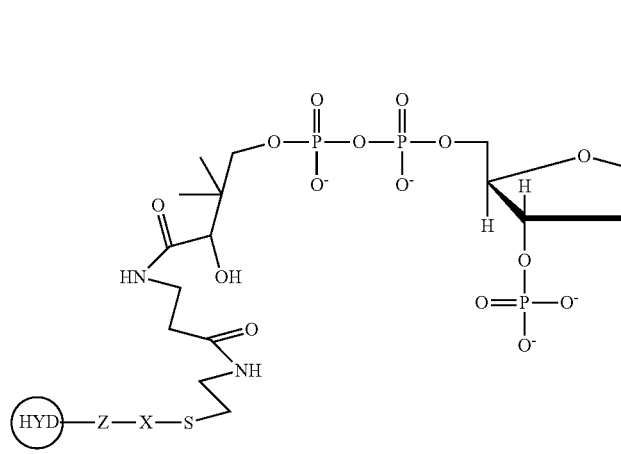

Where (HYD),

Z and X are as otherwise described above.

Each of the above compounds will produce compounds covalently linked to fusion proteins by action of the self-labeling tag of the fusion protein on the reactive moiety of the compounds described above.

Representative compounds which are produced by action of a self-labeling tag are represented by the following structure:

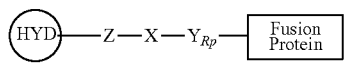

Where (HYD),

Z, X and

Fusion Protein are as otherwise described above, and $Y_{Rp}$ is a chemical moiety which is formed by the action of the fusion protein, preferably the self-labeling tag protein of the fusion protein, on group $Y_R$.

In the case of a fusion protein which comprises a halotag self-labeling tag protein, the reaction product is a compound according to the chemical structure:

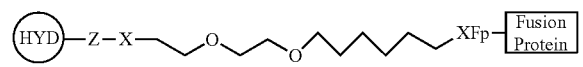

Where (HYD),

Z, X and

Fusion Protein are as otherwise described above. It is noted that the $Y_{Rp}$ group (represented as the alkyl diether group) forms a covalent bond (through a nitrogen, oxygen or sulfur group represented as a $X_{Fp}$ group) with the fusion protein.

In the case of a fusion protein which comprises a snaptap or a cliptag self-labeling tag protein, the reaction product is a compound according to the chemical structure:

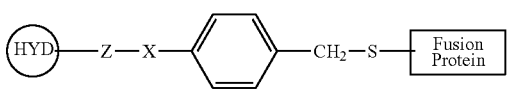

Where

Z, X and

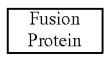

are as otherwise described above. It is noted that the $Y_{Rp}$ group (represented as a benzyl group) forms a covalent bond (through a sulfur group as represented) with the fusion protein.

In the case of a fusion protein which comprises a ACP or MCP self-labeling tag protein, the reaction product is a compound according to the chemical structure:

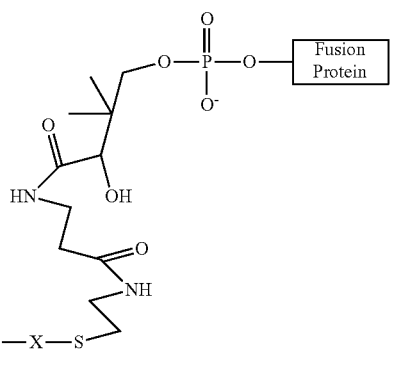

Where

Z, X and

are as otherwise described above. It is noted that the $Y_{Rp}$ group forms a covalent bond (through an oxygen group with the phosphate as represented) with the fusion protein.

BRIEF DESCRIPTION OF THE FIGURES

FIG. 16 shows ten representative polypeptide (amino acid) sequences for halotag, snaptag, cliptag, ACPtag and MCPtag self-labeling polypeptide tags used in the present invention.

DETAILED DESCRIPTION OF THE INVENTION

Figure 1:
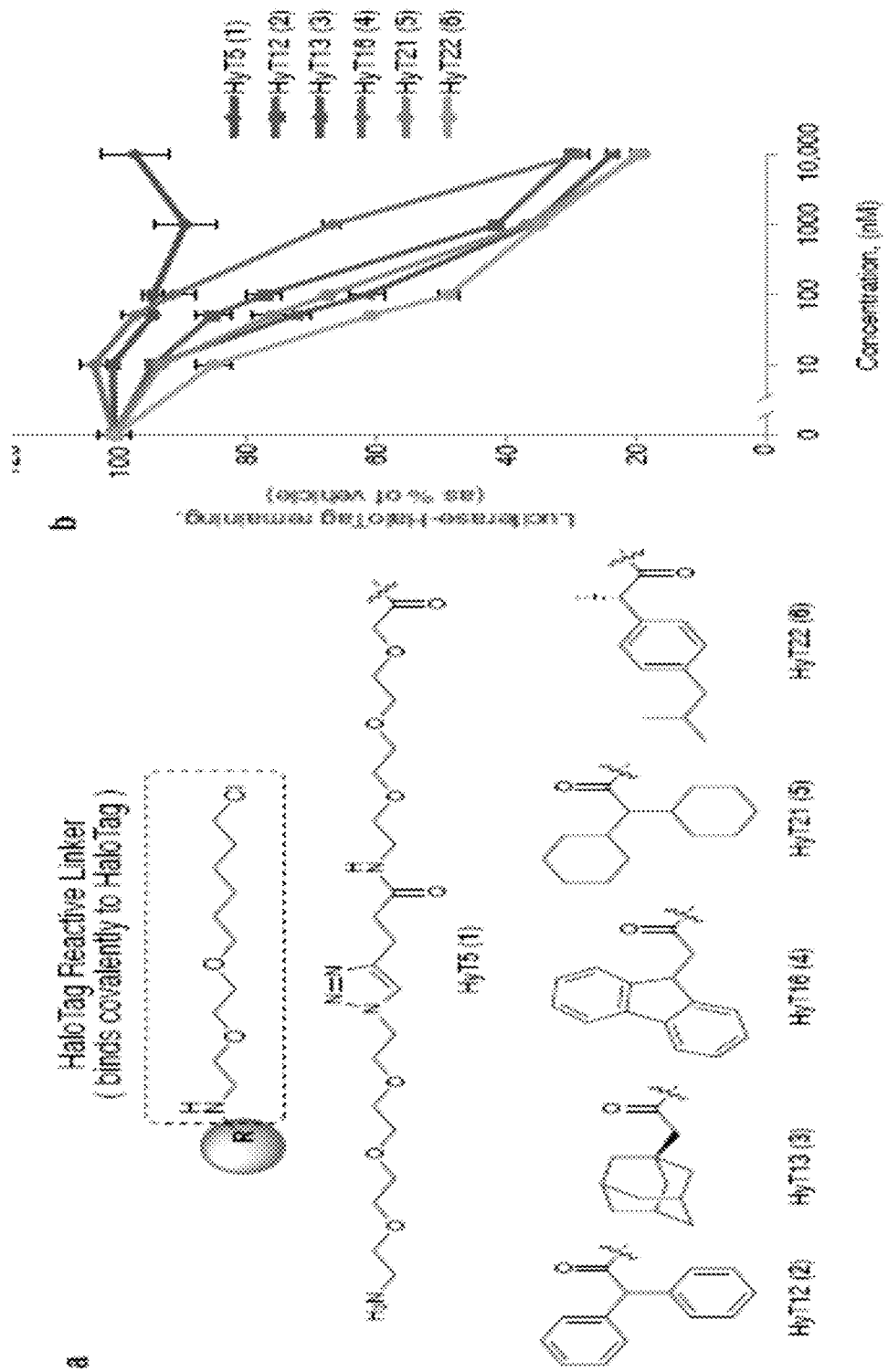
FIG. 1 shows a hydrophobic tagging strategy using the HaloTag fusion protein system. (a) Chemical structures of the representative HaloTag Ligands: HyT5, HyT12, HyT13, HyT16, HyT21 and HyT22. (b) HEK 293T cells expressing HA-HaloTag-luciferase were treated with indicated compounds at 1 µM for 24 hours, at which point luciferase assays were performed.
Figure 2:
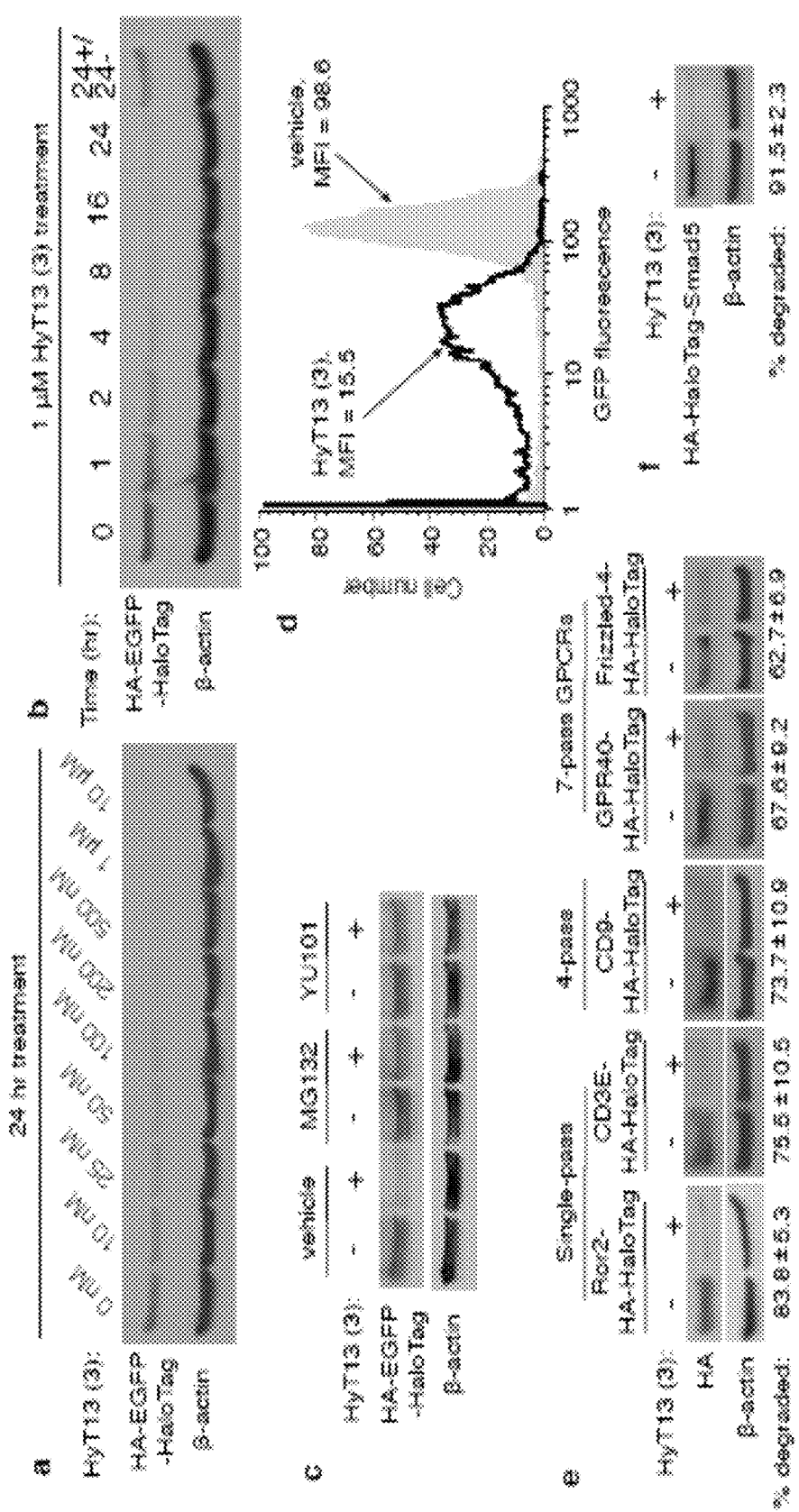
FIG. 2 shows that HyT13 leads to degradation of HaloTag fusion proteins. (a) Flp-In 293 cells expressing HA-EGFP-HaloTag were treated with indicated concentrations of HyT13 for 24 hours. The lysates were probed with anti-HA and anti-β-actin antibodies. (b) The same cell line as in (a) was treated for the indicated times with 1 µM HyT13. The rightmost sample was treated with HyT13 for 24 hours, after which HyT13-free media was provided for 24 hours. (c) The same cell line as in (a) was pretreated with proteasome inhibitors MG132 (10 µM) and YU101 (10 µM) for 1 hour prior to addition of 1 µM HyT13. The lysates were prepared from cells 6 hours after HyT13 addition. (d) HeLa cells stably expressing EGFP-HaloTag were treated with vehicle or 1 µM HyT13 for 24 hours, whereupon the intracellular GFP fluorescence was quantified by flow cytometry. MFI=mean fluorescence intensity. (e) HEK 293T cells stably expressing indicated transmembrane HA-HaloTag fusion proteins were treated with 1 µM HyT13 for 24 hours. Shown are representative images from at least three experiments; bands were quantified and mean degradation ±SEM is shown. (f) One-cell stage zebrafish embryos were injected with 100 ng of HA-HaloTag-Smad5 cRNA, grown to 256-cell stage and then treated with 10 µM HyT13 for 24 hours. Shown are representative images from at least three experiments; bands were quantified and mean degradation ±SEM is shown.
Figure 3:
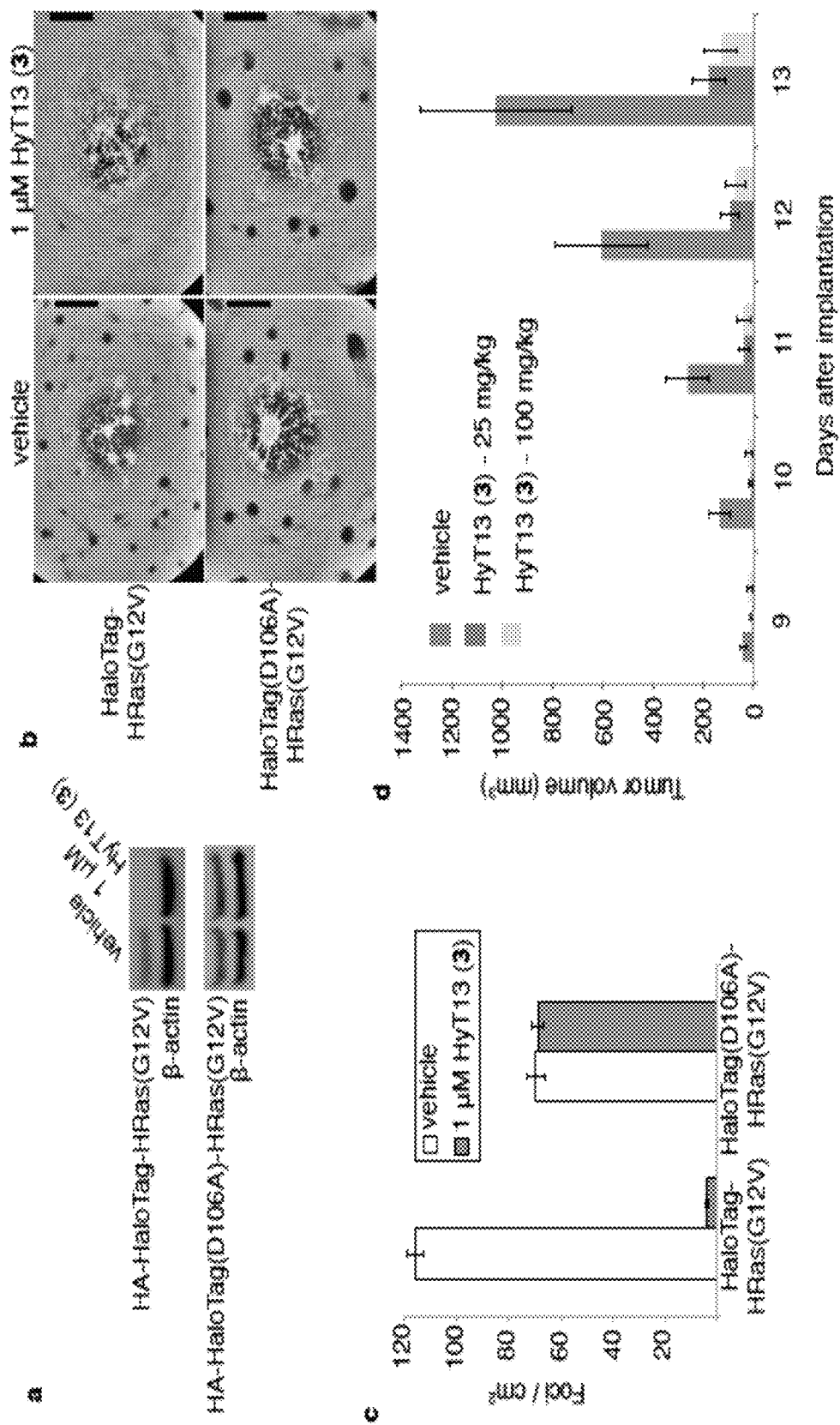
FIG. 3 shows the functional validation of HaloTag degradation by HyT13. (a) NIH-3T3 cells were retrovirally infected with a construct expressing either HA-HaloTag-HRas(G12V) or HA-HaloTag(D106A)-HRas(G12V). The cells were then treated with vehicle or 1 µM HyT13 for 24 hours. The lysates were prepared for immunoblotting and the blots were probed with anti-HA and anti-β-actin antibodies. (b) One hundred thousand NIH-3T3 cells infected with HA-HaloTag-HRas(G12V) or HA-HaloTag(D106A)-HRas(G12V) were plated in 10% FBS containing medium onto 10-cm plates. The next day, the medium was replaced with 1% FBS containing medium, along with vehicle or 1 µM HyT13. The media was refreshed every 2 days, and the plates were pictured on day 6. Bar, 5 mm. (c) Quantification of foci as described in (b). The number of foci/cm² was counted from three separate plates, with error bars representing SEM. (d) One hundred thousand HA-HaloTag-HRasG12V-expressing NIH-3T3 cells were injected into the flank of nude mice on day 0. The mice were administered IP injections of vehicle or HyT13 daily from day 0. Tumor size was measured daily, and the tumor volume was calculated. Each treatment group employed 7 mice. Error bars represent SEM.
Figure 4:
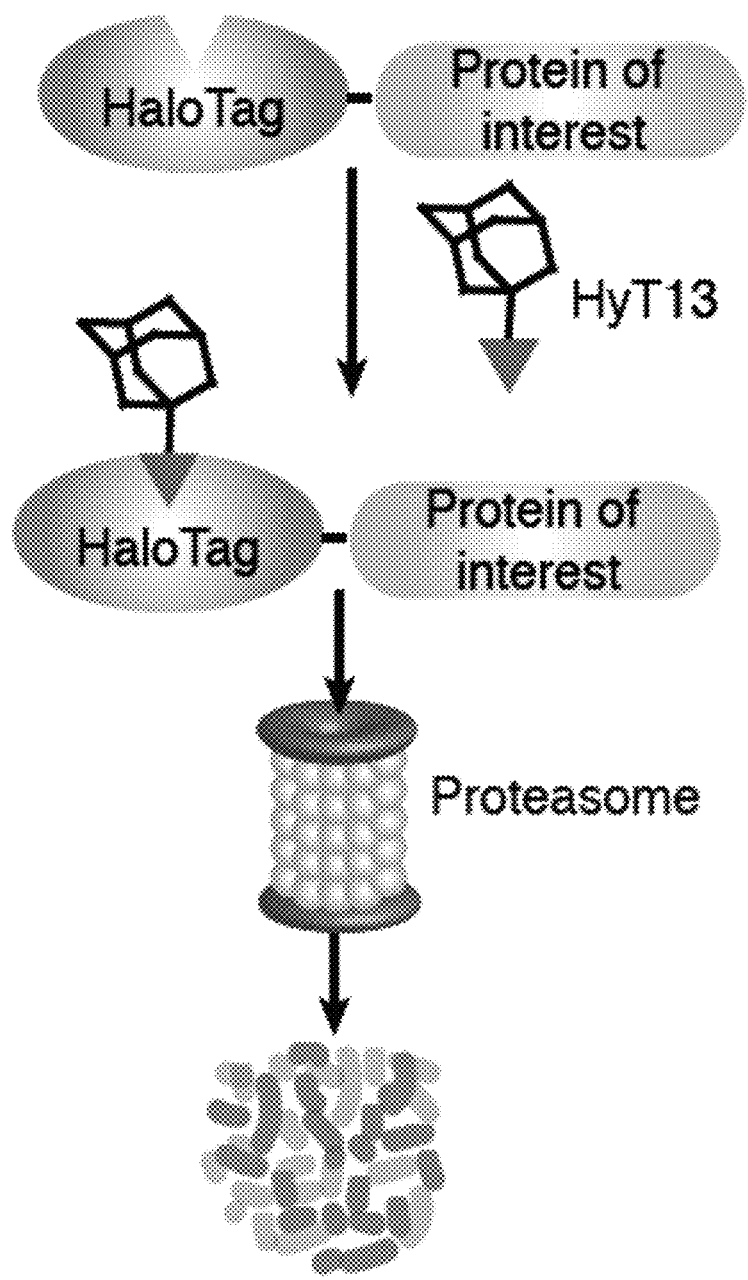
FIG. 4 shows the schematic of HyT13 mediated degradation of HaloTag fusion proteins. A fusion protein composed of a protein of interest and the HaloTag protein is degraded upon HyT13 treatment by the proteasome.

In accordance with the present invention there may be employed conventional chemical synthetic methods, as well as molecular biology, microbiology, and recombinant DNA techniques within the skill of the art. Such techniques are well-known and are otherwise explained fully in the literature. See, e.g., Sambrook et al, 2001, "Molecular Cloning: A Laboratory Manual"; Ausubel, ed., 1994, "Current Protocols in Molecular Biology" Volumes I-III; Celis, ed., 1994, "Cell Biology: A Laboratory Handbook" Volumes I-III; Coligan, ed., 1994, "Current Protocols in Immunology" Volumes I-III; Gait ed., 1984, "Oligonucleotide Synthesis"; Hames & Higgins eds., 1985, "Nucleic Acid Hybridization"; Hames & Higgins, eds., 1984, "Transcription And Translation"; Freshney, ed., 1986, "Animal Cell Culture"; IRL Press, 1986, "Immobilized Cells And Enzymes"; Perbal, 1984, "A Practical Guide To Molecular Cloning."

Where a range of values is provided, it is understood that each intervening value, to the tenth of the unit of the lower limit unless the context clearly dictates otherwise (such as in the case of a group containing a number of carbon atoms), between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

It is to be noted that as used herein and in the appended claims, the singular forms "a," "and" and "the" include plural references unless the context clearly dictates otherwise.

Furthermore, the following terms shall have the definitions set out below. It is understood that in the event a specific term is not defined hereinbelow, that term shall have a meaning within its typical use within context by those of ordinary skill in the art.

The term "compound", as used herein, unless otherwise indicated, refers to any specific chemical compound disclosed herein. Within its use in context, the term generally refers to a single compound comprising a hydrophobic moiety and a linker which is capable of reacting and forming a covalent bond with a fusion protein as otherwise described herein. In certain instances the term may also refer to stereoisomers and/or optical isomers (including racemic mixtures) or enantiomerically enriched mixtures of disclosed compounds. In the present invention in certain instances, especially in preferred aspects of the invention, the compound contains both a hydrophobic moiety and a linker moiety and is chemically linked through a covalent bond to a fusion protein such that the hydrophobic moiety can facilitate and/or produce degradation of the protein of interest which is part of the fusion protein. Compounds which are disclosed are those which are stable and where a choice of substituents and claim elements is available, the substituent or claim element is chosen such that stable compounds are formed from the disclosed elements and substituents.

The term "patient" or "subject" is used throughout the specification within context to describe an animal, generally a mammal and preferably a human, to whom a treatment or procedure, including a prophylactic treatment or procedure is performed. For treatment of those infections, conditions or disease states which are specific for a specific animal such as a human patient, the term patient refers to that specific animal. In most instances, the patient or subject of the present invention is a human patient of either or both genders.

The term "effective" is used herein, unless otherwise indicated, to describe an amount of a compound or composition which, in context, is used to produce or effect an intended result, whether that result relates to the binding of a hydrophobic moiety-linker compound onto a fusion protein or the use of a chemically modified fusion protein (to which is covalently bonded the hydrophobic group). The term effective subsumes all other effective amount or effective concentration terms which are otherwise described or used in the present application.

The term "protein of interest" is used to described inter alia, intracellular and extracellular proteins which exhibit function in or at the surface of a cell and may be considered drug targets for a disease state or condition. Proteins of interest include structural proteins, receptors, enzymes, cell surface proteins, proteins pertinent to the integrated function of a cell, including proteins involved in catalytic activity, aromatase activity, motor activity, helicase activity, metabolic processes (anabolism and catrabolism), antioxidant activity, proteolysis, biosynthesis, proteins with kinase activity, oxidoreductase activity, transferase activity, hydrolase activity, lyase activity, isomerase activity, ligase activity, enzyme regulator activity, signal transducer activity, structural molecule activity, binding activity (protein, lipid carbohydrate), receptor activity, cell motility, membrane fusion, cell communication, regulation of biological processes, development, cell differentiation, response to stimulus, behavioral proteins, cell adhesion proteins, proteins involved in cell death, proteins involved in transport (including protein transporter activity, nuclear transport, ion transporter activity, channel transporter activity, carrier activity, permease activity, secretion activity, electron transporter activity, pathogenesis, chaperone regulator activity, nucleic acid binding activity, transcription regulator activity, extracellular organization and biogenesis activity, translation regulator activity. Proteins of interest can include proteins from eukaryotes and prokaryotes including humans as targets for drug therapy, other animals, including domesticated animals, microbials for the determination of targets for antibiotics and other antimicrobials and plants, and even viruses, among numerous others. The protein of interest is one of the two proteins which comprise the fusion protein of the present invention which protein may be found at the amino terminus or the carboxylic acid terminus of the fusion protein; the other protein being a reporter protein (e.g., a green fluorescent protein, a red fluorescent protein, among others), more preferably a self-labeling tag (e.g., Halotag, Snaptag, Cliptag, ACPtag or MCPtag) as otherwise described herein.

The term "fusion protein" or "chimeric protein" as used herein, describes a protein created through the joining of two or more genes which originally coded for separate, distinct proteins. Translation of the fusion gene results in a single polypeptide (having two polypeptide segments) with functional properties derived from each of the original proteins. Fusion proteins according to the present invention are principally recombinant fusion proteins and are created artificially by recombinant DNA technology. In the present invention, the fusion proteins comprise a protein of interest and a second protein, which may be a reporter protein such as a green or red fluorescent protein or a luciferase protein or preferably, the second protein of the fusion protein is a self-labeling polypeptide tag protein such as a Halotag, Snaptag, Cliptag, ACPtag or MCPtag, as otherwise described herein. It is noted that the protein of interest may be positioned at the amino end or the carboxyl end of the fusion protein and the second protein to which a hydrophobic moiety is linked (e.g. reporter or tag polypeptide) may be positioned accordingly.

Fusion proteins according to the present invention are recombinant fusion proteins, created through engineering of a fusion gene. This typically involves removing the stop codon from a cDNA sequence coding for the first protein, then appending the cDNA sequence of the second protein in frame through ligation or overlap extension PCR, among other techniques. The introduced DNA sequence will then be expressed along with the other DNA sequence by a cell as a single protein. The protein can be engineered to include the full sequence of both original proteins, or only a portion of either. If the two entities are proteins, spacer peptides may be added which make it more likely that the proteins fold independently and behave as expected. In the case where the linkers enable protein purification, spacer peptides in protein or peptide fusions are sometimes engineered with cleavage sites for proteases or chemical agents which enable the liberation of the two separate proteins. Fusion proteins according to the present invention comprise a protein of interest and a second protein to which a hydrophobic tag may be linked. As described, fusion proteins according to the present invention comprise a protein of interest and a second polypeptide which functions to covalently bind a hydrophobic moiety as otherwise described herein. The second protein may be, for example, a reporter polypeptide such as a fluorescent protein or a luciferasse protein, but in preferred aspects of the invention, the second protein is a self-labeling polypeptide tag.

Fusion proteins according to the present invention may be created by utilizing commercially available expression vectors which can be used to prepare fusion genes which are created by inserting an appropriate DNA sequence into the expression vector which is introduced into an expression cell, such as yeast or a bacterial cell in order express the fusion protein. The present invention preferably utilizes fusion proteins which express a self-labeling polypeptide tag as otherwise described herein in addition to the protein of interest in order to link the hydrophobic moiety to the fusion protein.

The term "self-labeling polypeptide tag" or "self-labeling tag" is used to describe a polypeptide tag which is used in preferred fusion proteins according to the present invention as a means to covalently link a hydrophobic moiety to a protein of interest through a linker which is reactive with the self-labeling tag. The self-labeling tag comprises an enzyme (often mutated) which can be inserted into a fusion protein and is reactive with a specific moiety in order to covalently bind a linker (which contains the specific moiety on one end and a hydrophobic moiety on the other end) to the self-labeling tag and consequently, a hydrophobic moiety to the fusion protein. Preferred self-labeling tags include, for example, halotag, snaptag, cliptag, ACPtag and MCPtag self-labeling tags. All of these tags are readily available in commercially available expression vectors from Promega Corporation of Madison, Wis. (halotag) and New England BioLabs, Inc. of Ipswich, Massachussets, which vectors can accommodate the splicing of a gene for a protein of interest into the expression vector in order to produce the fusion protein comprising a protein of interest and a self-labeling polypeptide tag.

Figure 15:
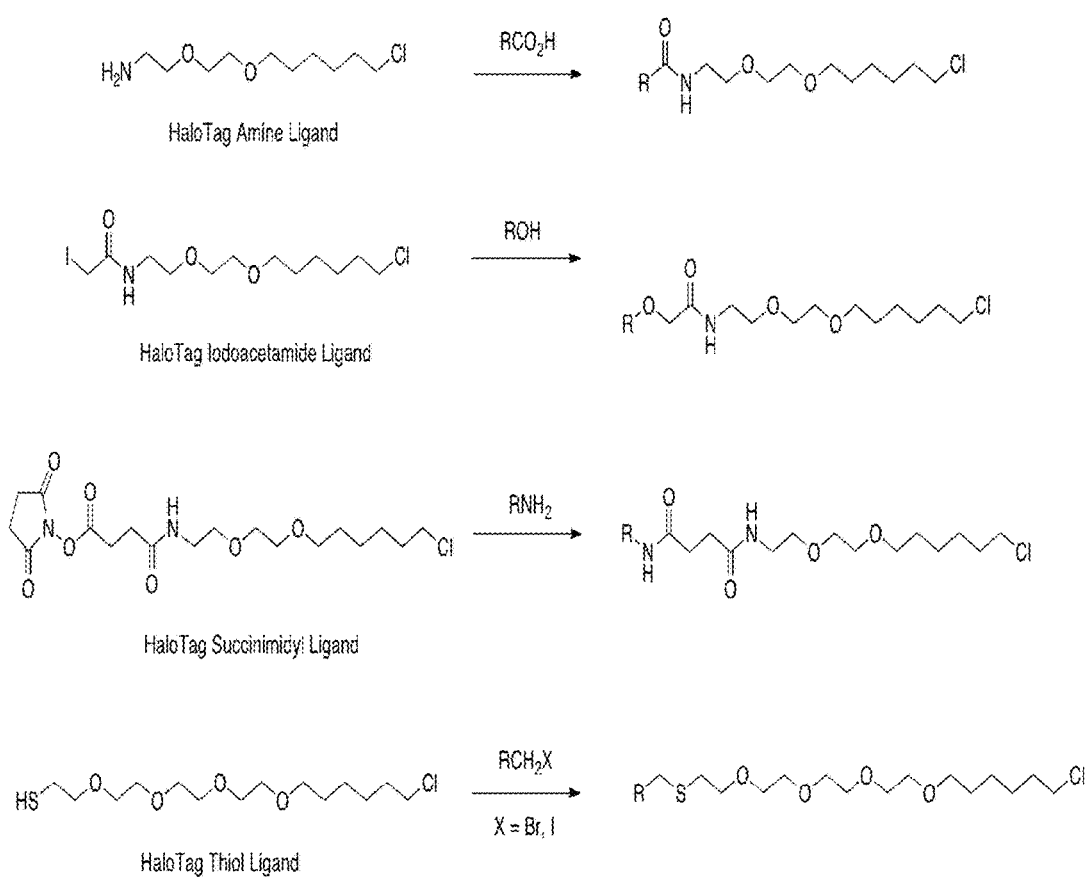
FIG. 15 shows certain prototypical approaches to create hydrophobic tags (ClogP>1.5) according to the present invention having a haloalkane reactive linker so as to be able covalenly link with a bacterial halogenase (halotag) polypeptide. Hydrophobic tags (HyTs) can be prepared via the coupling of the commercial Promega reactive ligands and $RCO_2H$, $RNH_2$, ROH, $RCH_2X$ by standard synthetic chemical techniques.

The halotag self-labeling polypeptide tag is based upon the halotag protein, a 34 kDa mutated bacterial hydrolase (haloalkane dehalogenase) which has been incorporated into expression vectors by Promega corporation, which are available commercially. For example, the halotag2 self-labeling tag (haloalkane dehalogenase) sequence SEQ ID NO: 1 (see FIG. 15) may be found at GenBank® Acc. #. AAV70825 and the expression vector at AY773970. The halotag7 polypeptide is SEQ ID NO:2 (FIG. 16). Halotag is reactive with haloalkanes and when expressed in fusion protein form, creates a covalent bond between the fusion protein and a reactive linker group onto which has been further linked a reporter moiety or, in the present application, a hydrophobic moiety (other than a fluorophore). Although a number of haloalkane groups may be used as the reactive linker in the halotag system in order to create a covalent bond, the preferred reactive linker is a

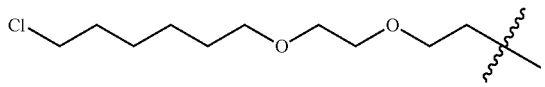 [SMILES: *CCOCCOCCCCCCCl]

group. The halogtag is readily available in commercially available expression vectors from Promega Corporation of Madison, Wis. (halotag). These vectors can accommodate the splicing of a gene for a protein of interest into the expression vector in order to produce the fusion protein comprising a protein of interest and a self-labeling polypeptide tag, expressed in E. coli as well as other expression vectors.

The snaptag self-labeling polypeptide tag is based upon a 20 kDa mutant of the DNA repair protein $O^6$-alkylguanine-DNA alkyltransferase that reacts specifically and rapidly with benzylguanine (BG) derivatives as otherwise described herein, leading to irreversible covalent labeling of the snaptag with a synthetic hydrophobic moiety containing probe though a sulfur group residing on the snaptag and the benzyl group of the benzylguanine synthetic probe. The rate of the reaction of snaptag with BG derivatives is to a large extent independent of the nature of the synthetic probe attached to BG and permits the labeling of snap fusion proteins with a wide variety of synthetic probes. Expression vectors for incorporating snaptag into numerous fusion proteins (e.g. psnap-tag(m), psnap-tag(m)2, psnap-tag(T7) and psnap-tag (T7)-2 Vector) are available from New England Biolabs, Inc., USA. The polypeptide sequences for each of the snaptag polypeptides (snaptagm, snaptagm2, snaptagT7 and snaptagT7-2) are found in FIG. 16 as psnap-tag(m) (SEQ ID NO:3), psnap-tag(m)2 (SEQ ID NO:4), psnap-tag(T7) (SEQ ID NO:5) and psnap-tag (T7)-2 (SEQ ID NO:6).

The cliptag self-labeling polypeptide tag is based upon a mutation of the snaptag DNA alkyltransferase enzyme, resulting in differential substrate specificity. In the case of cliptag protein, this protein react specifically with O2-benzylcytosine (BC) derivatives forming a covalent bond between a synthetic probe which is attached to O2-benzylcytosine and the cliptag through a sulfur group on the cliptag and the benzyl group on the benzylcytosine derivatives. The SNAP- and CLIP-tag fusion proteins can be labeled simultaneously and specifically with different synthetic probes in living cells. Expression vectors for incorporating sliptag into numerous fusion proteins (e.g. clip-tag(m) vector is available from New England Biolabs, Inc., USA). The polypeptide sequence for the cliptag polypeptide (cliptagm) is found in FIG. 16 as pclip-tag(m) (SEQ ID NO:7).

The use of ACP and MCP tags are somewhat different from the labeling of snap and clip fusion proteins, as the ACP and MCP tags are based on an enzyme-catalyzed post-translational modification. In this approach, the protein of interest is fused to an acyl carrier protein (ACP) and the corresponding fusion protein is specifically labeled with CoA derivatives through a post-translational modification catalyzed by the phosphopantetheinyl transferase AcpS (SCP synthase). The ACPtag is of a small size of 9 kDa. The MCPtag, which is a mutant of the ACP tag of similar size is labeled by the phosphopantetheinyl transferase Sfp (Sfp synthase) but not by ACP synthase, thereby permitting the selective labeling of ACP and MCP fusion proteins with different probes in one sample. In contrast to substrates of the halotag, snaptag and cliptag, substrates of the ACPtag (ACPtagm and ACPtagm-2) and MCPtag (MCPtagm) are not cell permeable, although this approach may be readily utilized where the protein of interest is a cell surface protein. Expression vectors for these tags (pACP-tag(m), pACP-tag (m)-2 and pMCP-tag(m)) are available from New England Biologics, Inc., Massachussets, USA. These expression vectors may be used to readily accommodate many proteins of interest to provide an assortment of fusion proteins to determine the functionality and important of a protein of interest in methods according to the present invention. These vectors can accommodate the splicing of a gene for a protein of interest into the expression vector in order to produce the fusion protein comprising a protein of interest and a self-labeling polypeptide tag, expressed in E. coli as well as other expression vectors. The polypeptide sequences for each of the ACPtag and MCPtag polypeptides is found in FIG. 16 as pACP-tag(m) (SEQ ID NO:8), pACP-tag(m)-2 (SEQ ID NO:9) and pMCP-tag(m) (SEQ ID NO:10).

The preferred self-labeling tags for use in the present invention, halotag, snaptag, cliptag, ACPtag and MCPtag can be used to selectively label corresponding fusion proteins with synthetic probes containing hydrophobic moieties as described herein in both cell assay and in vitro applications.

The term "hydrophobic group" or "hydrophobic moiety" is used to describe a hydrophobic group which is covalently linked to a fusion protein according to the present invention which destabilizes and degrades a protein of interest in the fusion protein such that the fusion protein becomes degraded in a cell (proteasomal degradation). In the present invention, the hydrophobic group has the following physicochemical characteristics, in particular, as represented by having a ClogP value of at least about 1.5, at least about 1.75, at least about 2.0, at least about 2.25, at least about 2.5, at least about 2.75, at least about 3.0, at least about 3.25, at least about 3.5, at least about 3.75, at least about 4.0, at least about 4.25, at least about 4.5, at least about 4.75, at least about 5.0, at least about 5.25, at least about 5.5.

ClogP is a value which may be readily calculated using ClogP software, available from Biobyte, Inc., Claremont, Calif., USA and applied to any computer which utilizes Windows, linux or an Apple operating system. ClogP software is readily adaptable to a number of chemical programs including ChemDraw programs and related chemical structure drawing programs. The value ClogP assigns to the hydrophobicity of a chemical or moiety is based upon a determination of log P n-octanol/water ($logP_{OW}$), which is the log of the partition coefficient of a molecule or moiety in octanol and water. ClogP accurately estimates $logP_{OW}$ numbers and provides a readout of a value which may be readily applied to the present invention. Newer versions of Chem-Draw software, available from CambridgeSoft, Inc., Cambridge Mass., USA. incorporate the ability to interface with ClogP software and provide ClogP calculations, which may readily accomplished by simply drawing a molecule and applying the ClogP calculation app from that software to the hydrophobic molecule or moiety to be utilized. Thus, according to the present invention, virtually any hydrophobic moiety may be proposed and chemically synthesized and incorporated into a reactive linker with the expectation that that moiety when incorporated into a fusion protein as otherwise disclosed herein, will produce degradation of the fusion protein (containing a protein of interest) consistent with the method of the present invention.

Figure 14:
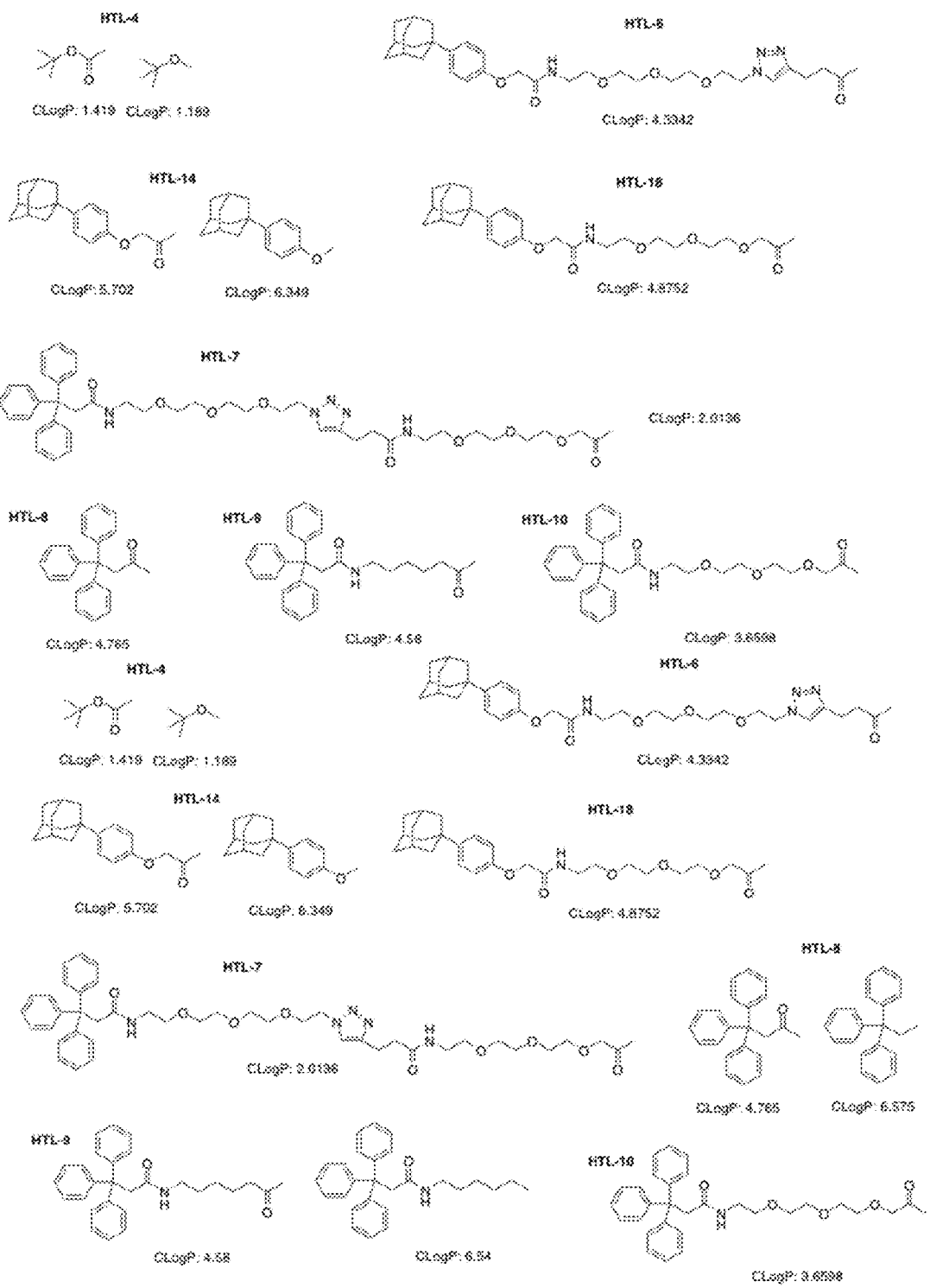
FIG. 14 shows a number of representative hydrophobic moieties which are covalently linked to fusion proteins as otherwise described herein.
Figure 14:
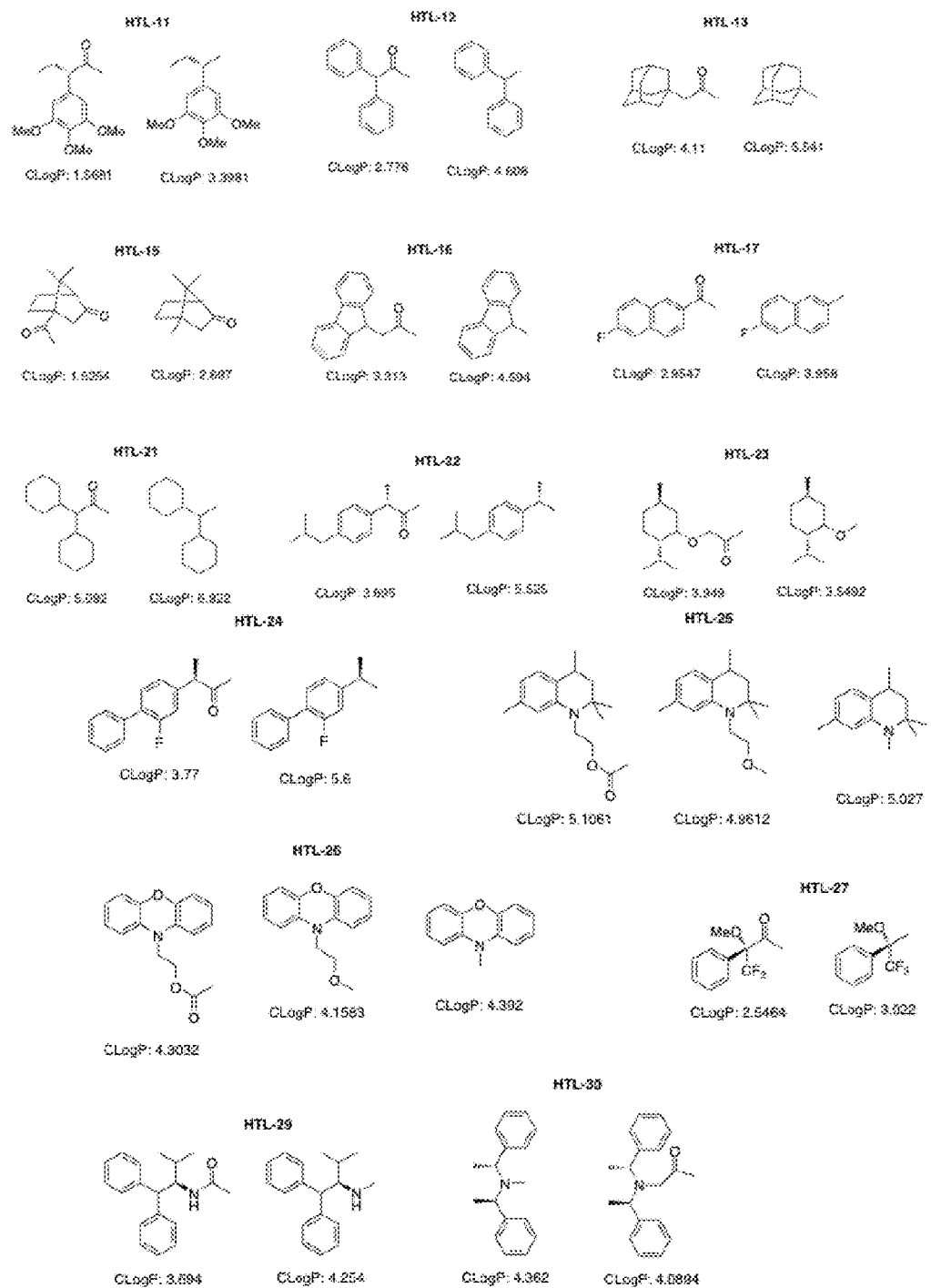
Figure 14:
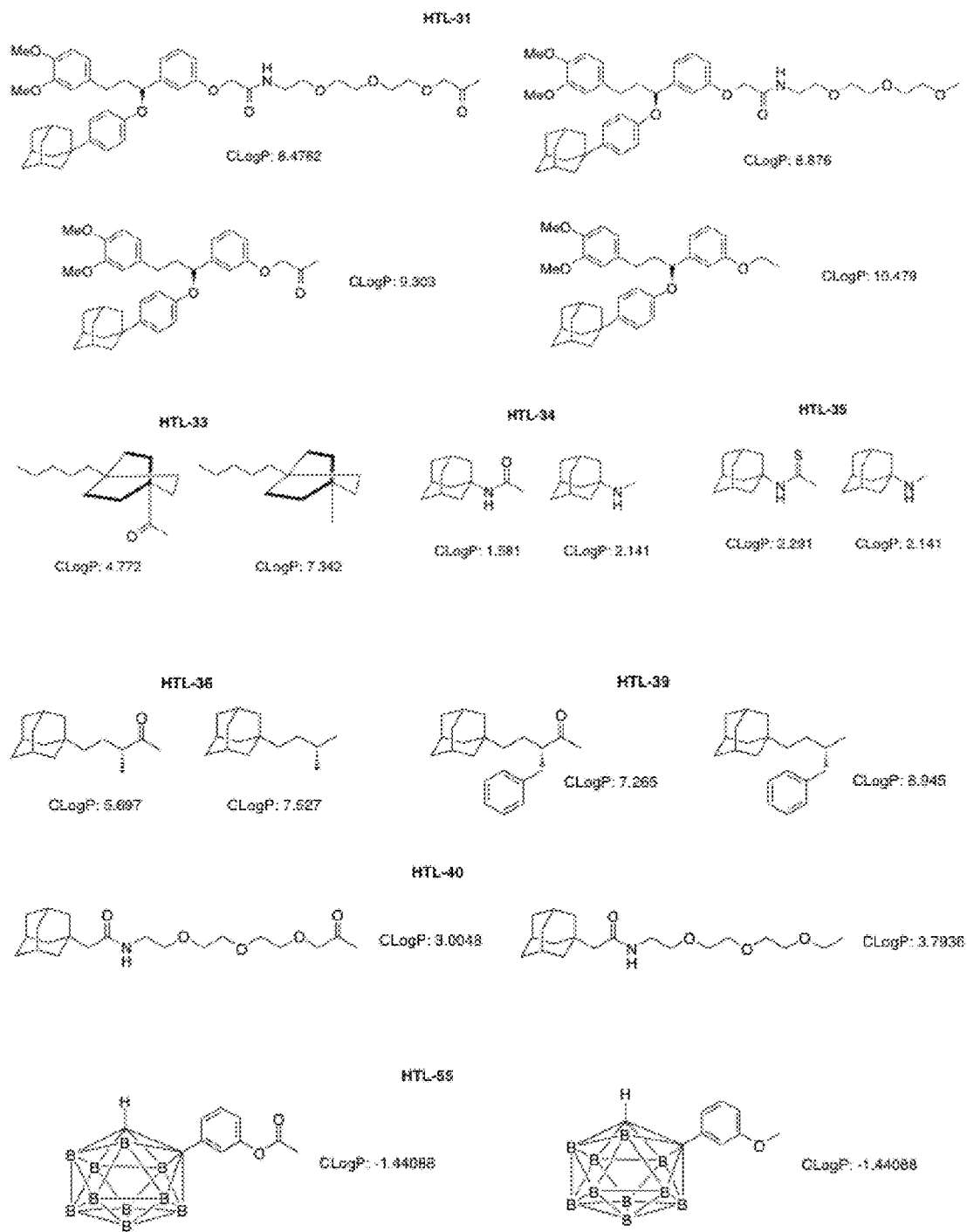

In the present invention, virtually any hydrophobic group having a calculated ClogP value of at least about 1.5 (as otherwise disclosed hereinabove) may be used to facilitate the degradation of the protein of interest in the fusion protein. Representative hydrophobic groups include optionally substituted hydrocarbyl groups containing at least three carbon atoms, such as optionally substituted $C_3$-$C_{30}$ alkyl, alkene or alkyne groups, including linear, branch-chained or cyclic (including bi-cyclo, adamantly and fused ring groups) hydrocarbon groups, aryl groups, including aryl groups containing a single ring or 2 or more fused rings (e.g., two, three or four fused rings) such as optionally substituted phenyl groups, including optionally substituted naphthyl groups (including 1- or 2-naphthyl groups), optionally substituted anthracenyl, phenanthrenyl, and phenacenyl (chrysene) groups, optionally substituted triphenyl methyl (trityl, methoxytrityl) groups, optionally substituted hydrophobic heterocyclic, including heteroaryl groups such as optionally substituted quinolinyl groups, among others. Representative hydrophobic groups are found in the chemical compounds which are presented in attached FIGS. 5 and 14 respectively. One of ordinary skill in the art may readily adapt ClogP software, combined with a structural chemical program (e.g. ChemDraw) to readily provide hydrophobic moieties useful in the present invention. In addition, the person of ordinary skill may modify numerous moieties with hydrophobic moieties to increase the hydrophobicity of the moiety to provide a ClogP value significantly greater than 1.5. It is noted that in certain instances, useful hydrophobic moieties may have values of ClogP less than 1.5, but those moities contain substantial steric bulk which compensates for the low levels of hydrophobicity. The inclusion of a borane nido-decaborane group ($B_{10}H_{14}$) substituent on an aryl group such as a phenyl, naphthyl, phenanthrenyl, anthracenyl (paranaphthyl), etc.

The term "hydrocarbon" or "hydrocarbyl" refers to any monovalent radical containing carbon and hydrogen, which may be straight, branch-chained or cyclic in nature. Hydrocarbons include linear, branched and cyclic hydrocarbons, including alkyl groups, alkylene groups, saturated and unsaturated hydrocarbon groups (e.g., alkene, alkyne), including aromatic groups both substituted and unsubstituted.

"Alkyl" refers to a fully saturated monovalent radical containing carbon and hydrogen, and which may be cyclic, branched or a straight chain containing from 1 to 30 carbon atoms, from 1 to 20 carbon atoms, preferably 1 to 10 carbon atoms. Examples of alkyl groups are methyl, ethyl, n-butyl, n-hexyl, n-heptyl, n-octyl, isopropyl, 2-methylpropyl, cyclopropyl, cyclo-propylmethyl, cyclobutyl, cyclopentyl, cyclopentylethyl, cyclohexylethyl and cyclohexyl. Preferred alkyl groups are $C_1$-$C_6$ or $C_3$-$C_{10}$ alkyl groups. "Alkylene" refers to a fully saturated hydrocarbon which is divalent (may be linear, branched or cyclic) and which is optionally substituted. Other terms used to indicate substitutent groups in compounds according to the present invention are as conventionally used in the art.

"Aryl" or "aromatic", in context, refers to a substituted or unsubstituted monovalent aromatic radical having a single ring (e.g., benzene) or multiple condensed rings (e.g., naphthyl, anthracenyl, phenanthryl, phenacenyl) and can be can be bound to the compound according to the present invention at any position on the ring(s). Other examples of aryl groups, in context, may include heterocyclic aromatic ring systems "heteroaryl" groups having one or more nitrogen, oxygen, or sulfur atoms in the ring (moncyclic) such as imidazole, furyl, pyrrole, pyri-dyl, furanyl, thiene, thiazole, pyridine, pyrimidine, pyrazine, triazole, oxazole, indole or preferably fused ring systems (bicyclic, tricyclic), among others, which may be substituted or unsubstituted as otherwise described herein. Preferred heteroaryl groups are hydrophobic in nature or can be rendered hydrophobic by including one or more hydrophobic substituents on the heteroaryl group, or creating a fused system where at least one of the rings is a benzene (phenyl) ring.

The term "cyclic" shall refer to an optionally substituted carbocyclic or heterocyclic group, preferably a 5- or 6-membered ring or fused rings (two, three or four rings) preferably containing from 8 to 14 atoms. A heterocyclic ring or group shall contain at least one monocyclic ring containing between 3 and 7 atoms of which up to four of those atoms are other than carbon and are selected from nitrogen, sulfur and oxygen. Carbocyclic and heterocyclic rings according to the present invention may be unsaturated or saturated. Preferred cyclic groups are hydrocarbyl groups, preferably unsaturated hydrocarbyl groups which are optionallyl substituted. Other preferred cyclic groups are bicyclo alkyl groups or adamantly groups, each of which may be optionally substituted. Preferred heterocyclic groups are heteroaryl or heteroaromatic.

The term "heterocyclic group" as used throughout the present specification refers to an aromatic ("heteroaryl") or non-aromatic cyclic group forming the cyclic ring(s) and including at least one hetero atom such as nitrogen, sulfur or oxygen among the atoms forming the cyclic ring. The heterocyclic ring may be saturated (heterocyclic) or unsaturated (heteroaryl). Exemplary heterocyclic groups include, for example pyrrolidinyl, piperidinyl, morpholinyl, pyrrole, pyridine, pyridone, pyrimidine, imidazole, indole, quinoline, isoquinoline, quinolizine, phthalazine, naphthyridine, quinazoline, cinnoline, acridine, phenacene, thiophene, benzothiophene, furan, pyran, benzofuran, thiazole, benzothiazole, phenothiazine and carbostyryl, more preferably pyrrolidinyl, piperidinyl, morpholinyl, pyrrole, pyridine, thiophene, benzothiophene, thiazole, benzothiazole, quinoline, quinazoline, cinnoline and carbostyryl, and even more preferably thiazole, quinoline, quinazoline, cinnoline, carbostyryl, piperazinyl, N-methylpiperazinyl, tetrahydropyranyl, 1,4-dioxane and phthalimide, among others.

Exemplary heteroaryl moieties which may be used in the present invent ion include for example, pyrrole, pyridine, pyridone, pyridazine, pyrimidine, pyrazine, pyrazole, imidazole, triazole, tetrazole, indole, isoindole, indolizine, purine, indazole, quinoline, isoquinoline, quinolizine, phthalazine, naphthyridine, quinoxaline, quinazoline, cinnoline, pteridine, imidazopyridine, imidazotriazine, pyrazinopyridazine, acridine, phenanthridine, carbazole, carbazoline, perimidine, phenanthroline, phenacene, oxadiazole, benzimidazole, pyrrolopyridine, pyrrolopyrimidine and pyridopyrimidine; sulfur-containing aromatic heterocycles such as thiophene and benzothiophene; oxygen-containing aromatic heterocycles such as furan, pyran, cyclopentapyran, benzofuran and isobenzofuran; and especially aromatic heterocycles comprising 2 or more hetero atoms selected from among nitrogen, sulfur and oxygen, such as thiazole, thiadizole, isothiazole, benzoxazole, benzothiazole, benzothiadiazole, phenothiazine, isoxazole, furazan, phenoxazine, pyrazoloxazole, imidazothiazole, thienofuran, furopyrrole, pyridoxazine, furopyridine, furopyrimidine, thienopyrimidine and oxazole. Further heteroaryl groups may include pyridine, triazine, pyridone, pyrimidine, imidazole, indole, quinoline, isoquinoline, quinolizine, phthalazine, naphthyridine, quinazoline, cinnoline, acridine, phenacene, thiophene, benzothiophene, furan, pyran, benzofuran, thiazole, benzthiazole, phenothiazine, pyrrolopyrimidine, furopyridine, furopyrimidine and thienopyrimidine, preferably benzothiophene, benzothiazole, quinoline, quinazoline, cinnoline, pyrrolopyrimidine, furopyridine and thienopyrimidine.

The term "substituted" shall mean substituted at a carbon (or nitrogen) position within context, hydroxyl, carboxyl, cyano (C≡N), nitro ($NO_2$), halogen (preferably, 1, 2 or 3 halogens, especially on an alkyl, especially a methyl group such as a trifluoromethyl), thiol, alkyl group (preferably, $C_1$-$C_{10}$ more preferably, $C_1$-$C_6$), alkoxy group (preferably, $C_1$-$C_{10}$ alkyl or aryl, including phenyl and substituted phenyl), ester (preferably, $C_1$-$C_{10}$ alkyl or aryl) including alkylene ester (such that attachment is on the alkylene group, rather than at the ester function which is preferably substituted with a $C_1$-$C_{10}$ alkyl or aryl group), thioether (preferably, $C_1$-$C_{10}$ alkyl or aryl), thioester (preferably, $C_1$-$C_{10}$ alkyl or aryl), (preferably, $C_1$-$C_{10}$ alkyl or aryl), halogen (F, Cl, Br, I), nitro or amine (including a five- or six-membered cyclic alkylene amine, further including a $C_1$-$C_{10}$ alkyl amine or $C_1$-$C_{10}$ dialkyl amine), amido, which is preferably substituted with one or two $C_1$-$C_{10}$ alkyl groups (including a carboxamide which is substituted with one or two $C_1$-$C_{10}$ alkyl groups), alkanol (preferably, $C_1$-$C_{10}$ alkyl or aryl), or alkanoic acid (preferably, $C_1$-$C_{10}$ alkyl or aryl). Preferably, the term "substituted" shall mean within its context of use alkyl, alkoxy, halogen, ester, keto, nitro, cyano and amine (especially including mono- or di-$C_1$-$C_{10}$ alkyl substituted amines). Any substitutable position in a compound according to the present invention may be substituted in the present invention, but preferably no more than 5, more preferably no more than 3 substituents are present on a single ring or ring system. Preferably, the term "unsubstituted" shall mean substituted with one or more H atoms. Preferred substituents are those which have hydrophobic characteristics as otherwise described herein. It is noted that the incorporation of a hydrophobic substituent onto an otherwise less hydrophobic or non-hydrophobic moiety may render the enter moiety hydrophobic as described for the present invention. A preferred substituent on aryl groups (e.g., phenyl, naphthyl) for use in the present invention is the borane nido-decaborane group ($B_{10}H_{14}$), which although is not a hydrophobic group per se, provides the favorable characteristics of a significant steric effect to enhance degradation of fusion proteins in the present invention.

The term "linker" is used to describe a chemical group which covalently links the hydrophobic moiety to the fusion protein in preferred aspects of the present invention. In particular, the linker binds to the hydrophobic moiety at one end and to the fusion protein at the other end. In its broadest aspects, the linker may link the hydrophobic moiety to the fusion protein using conventional chemistry, by reacting (condensing) a nucleophilic group on the fusion protein (an amine, sulfhydryl or hydroxyl group) with an electrophilic group (carboxylic acid, etc.) on the linker to which the hydrophobic groups is attached, thus providing a compound which links the hydrophobic moiety to the fusion protein via the linker. In certain preferred embodiments, the linker binds to a self-labeling tag of the fusion protein by the action of the self-labeling tag on a reactive portion of the linker ("reactive linker"), depending upon the type of self-labeling tag. The chemistry associated with the various linkers according to the present invention will be a function of the fusion protein to which the hydrophobic moiety is to be linked, especially in the case where the fusion protein comprises a self-labeling protein tag (halotag, etc. as otherwise disclosed herein), in which case the chemistry of the linker will reflect the substrate specificity of the self-labeling protein tag. Because the reactive moiety of the linker is specific to the self-labeling tag used in the fusion protein of the present invention, the chemistry of the linker at that (reactive end) end which covalently binds to the fusion protein will be a function of the substrate specificity for that self-labeling tag protein. Thus, the reactive moiety of the linker is specific as a substrate for the self-labeling tag of the fusion protein, wherein the self-labeling tag is preferably a HALOtag, a SNAPtag, a CLIPtag, a ACPtag or a MCPtag, all well-known in the art.

Preferably, the self-labeling tag is a HALOtag, in particular a haloalkane group (preferably a $C_2$-$C_{12}$ chloralkyl, even more preferably, a haloalkyl diether group, in preferred aspects a group according to the chemical structure:

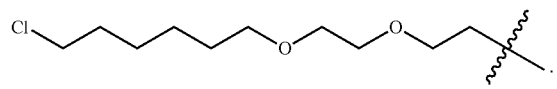 [SMILES: *CCOCCOCCCCCCCl]

In the case of where the fusion protein comprises a self-labeling tag as a SNAPtag, $Y_R$ is a benzylguanine group which forms a compound according to the chemical structure:

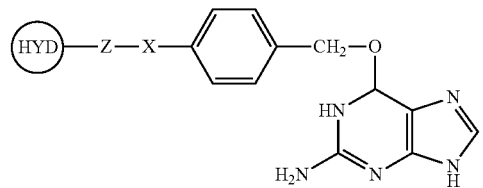

Where

,

Z and X are as otherwise described above.

In the case where the fusion protein comprises a self-labeling tag as a CLIPtag, $Y_R$ is a benzylcytosine group which forms a compound according to the chemical structure:

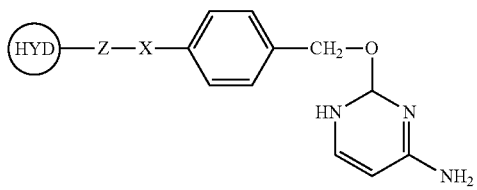

Where

,

Z and X are as otherwise described above.

In the case where the fusion protein comprises a self-labeling tag as a ACPtag or a MCPtag, $Y_R$ is a coenzyme A derivative which forms a compound according to the chemical structure:

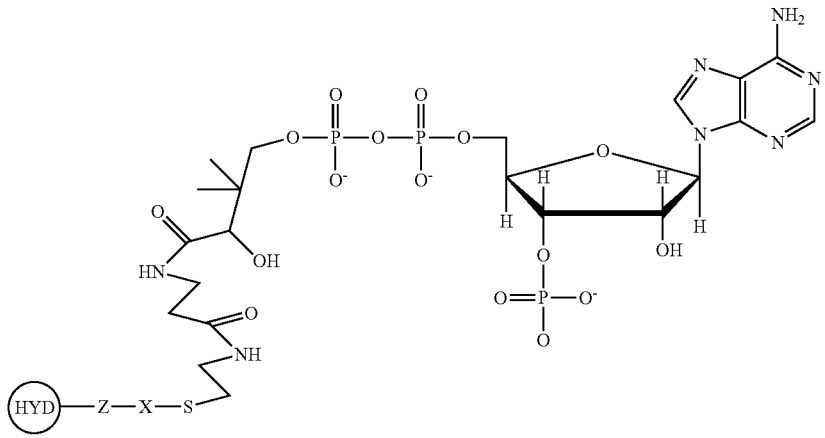

Where

,

Z and X are as otherwise described above.

The term "connector", symbolized in compounds according to the present invention by the symbol [CON], is used to describe a chemical moiety which is optionally included in compounds according to the present invention in linker groups as otherwise described herein. The connector group is the resulting moiety which forms from the facile condensation of two separate chemical fragments which contain reactive groups which can provide connector groups as otherwise described to produce linker groups which covalent link hydrophobic moieties to fusion proteins in compounds according to the present invention. It is noted that a connector is distinguishable from a linker in that the connector is the result of a specific chemistry which is used to provide compounds according to the present invention wherein the reaction product of these groups results in an identifiable connector group which forms a linker group of greater length as otherwise described herein.

Common connector groups which are used in the present invention include the following chemical groups:

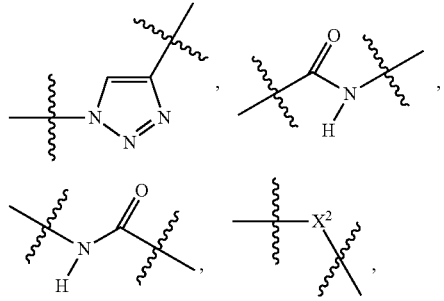

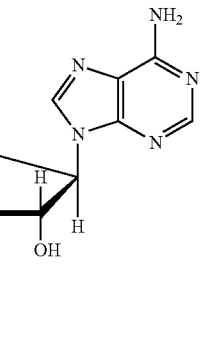

-continued

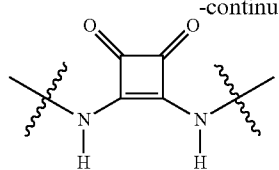

Where $X^2$ is O, S, $NR^4$, S(O), $S(O)_2$, —$S(O)_2O$, —$OS(O)_2$, or $OS(O)_2O$;

$X^3$ is O, S, $NR^4$; and $R^4$ is H or a $C_1$-$C_3$ alkyl group.

Compounds according to the present invention are readily synthesized using methods well known in the art. In the present invention, a preferred approach to providing a reactive linker with a hydrophobic moiety covalently linked to same follows well established synthetic chemical methods. A hydrophobic moiety may be derivatived and a convenient approach is to provide a hydrophobic moiety which contains a carboxylic acid or other electrophilic functional group to react with a nucleophilic (e.g. amine, hydroxyl or sulfhydryl) group on a linker molecule to provide a hydrophobic moiety-containing linker. The hydrophobic linker may contain a reactive moiety to covalently bond the linker to a fusion protein or the hydrophobic linker may be derivatized to provide a functional group (e.g., a nucleophilic or electrophilic moiety) which is capable of reacting with the fusion protein. In the case of the use of a self-labeling polypeptide tag to covalently link the hydrophobic moiety to the fusion protein, the hydrophobic containing linker is derivatized to contain (preferably, at the distil end away from the hydrophobic moiety) a chemical moiety which acted upon by the self-labeling tag (e.g., halo, snap, clip, ACP or MCP) as otherwise described herein. The formation of the function groups which are reactive with the self-labeling tag is well known and readily provided using chemical synthetic technicals which are well known in the art. In the case of the halotag, the formation of a haloalkane, in particularly preferred aspects of the present invention, a chloroalkyldiether moiety as otherwise described herein is readily accomplished from commercially available intermediates. Particular synthetic approaches are provided in the examples section which follows. In the case of the benzyl guanosine and benzyl cytosine linker analog substrates of snaptag and cliptag self-labeling tags, these are readily provided from reactive linkers which are end-capped with benzyl guanosine and benzyl cytosine respectively.

Once the reactive linker comprising a hydrophobic moiety is provided, reaction with the fusion protein commences to covalently link the hydrophobic moiety to the fusion protein. The reactive linker may be covalently linked to the fusion protein outside of the cell via standard chemical reaction, but preferably is linked via the self-labeling tag intracellularly. The reactive linker and fusion protein may be reacted intracellularly, separate and then utilized in an assay to determine the function and importance of the protein of interest in the fusion protein as a potential target, or alternatively, the fusion protein and reactive linker may be introduced intracellularly within the same cell in which the assay for function and importance takes place. The compounds according to the present invention may be utilized in vitro or in vivo, and may be used in cell-based assays and in animals models, given that the relatively low toxicity of many of the the compounds is consistent with in vivo utilization.

The compounds according to the present invention may be used in cell based assays to determine the function and importance of a protein of interest, by assaying cell function as a consequence of the degradation of the fusion protein to which the hydrophobic moiety is covalently bonded. These assays may be based upon prokaryote and/or eukaryote cells and may be directed to animal and plant proteins, as well as microbial proteins, such as fungal and bacterial proteins, as well as viral proteins. Degradation of the fusion protein containing the protein of interest may be indicative of the importance of the protein of interest to an important function which modulates a disease state or condition, for example, the growth of cancer cells, an inflammatory response or other biological response, or the proliferation of bacteria and/or viruses. Degradation of the fusion protein under assay conditions may be readily monitored using one of the many standard techniques available in the art, including immunoblot, immunoassay (e.g. ELISA, among others), absorbance assays, mass spectrometric methods and proteomics methods, among others. Virtually any technique for measuring proteins may be adapted for use in the present method provided it is otherwise consistent with the integrity of the assay performed using compounds according to the present invention.

Elucidating the in vivo function of protein function for drug target validation is a stumbling block in drug development, which may be readily addressed using the present invention hydrophobic tagging methodology. For example, many G Protein-Coupled Receptors (GPCRs) GPCRs lack a known ligand or function. One could introduce the HaloTag gene into the mouse genome such that the knock-in transgene encodes a halotag fusion protein fused to a protein of interest, e.g., an orphan GCPR. Administration of a hydrophobic tagged reactive linker to animals expressing the fusion protein would induce the degradation of the fusion protein (by facilitating the covalent linking of the hydrophobic moiety containing reactive linker to the fusion protein) and the resulting phenotypic response would mimic the effect of a drug (e.g., as an inhibitor of the protein of interest), thus validating the GPCR (or any other protein) as a drug target.

Another example of the temporal control advantage offered by the present invention is in the area of parasite drug target validation. It is difficult to determine the functional consequence of inhibiting certain parasite proteins due to their complex life cycles, i.e., a protein might be needed at two stages, an early one in an animal vector and a latter one in humans. It would be desirable to retain protein function during the early stage but then to be able to eliminate it at the later stage so as to mimic the effects of a human drug against this parasite. By replacing the gene for a particular parasite protein with a self-labeling tag (e.g., halotag) fused with a candidate gene (producing a protein of interest) and then inducing the degradation of this expressed fusion protein using the hydrophobic tagging methodology, one will be able to validate the candidate parasite protein as a drug target.

The present invention will now be further described by way of the following examples, the description of which should be taken to merely exemplify, but not limit, the present invention.

EXAMPLES

Overview

To develop a general method to degrade any intracellular protein using a small molecule, we sought to enlist the cellular protein quality control machinery. The burial of internal hydrophobic residues within a protein's core is a major driving force behind protein folding, and, correspondingly, exposure of such hydrophobic regions is considered a hallmark of an unfolded protein[21-23]. For instance, the endoplasmic reticulum Hsp70-class chaperone BiP specifically binds hydrophobic amino acids and helps slow-folding proteins to fold[22,24]. Should the cell fail to fold the target protein correctly, the unfolded protein is eliminated by either the ubiquitin-proteasome system or autophagy[25]. We sought to mimic the partially denatured state of a protein by appending a hydrophobic tag on its surface in order to induce its degradation. To test this hypothesis, we selected the HaloTag dehalogenase system developed by Promega as the fusion protein component[26]. This system was chosen because HaloTag fusion proteins are commercially available in various formats and the haloalkane reactive linker binds to the HaloTag domain covalently, suggesting a high specificity of the ligand for HaloTag. Here, we demonstrate that hydrophobic tagging affords rapid and robust control of the abundance of numerous proteins, including transmembrane receptors, in cultured cells as well as in zebrafish and mouse models.

Chemical Synthesis

Materials, Purification, and Analysis.

Reagents used for chemical synthesis were purchased from Sigma-Aldrich Co. and were used without further purification. All reactions were performed in oven-dried or flame-dried glassware fitted with rubber septa under a positive pressure of nitrogen. THF was distilled from sodium/benzophenone. Dichloromethane was distilled from calcium hydride. Analytical thin layer chromatography (TLC) was performed using glass plates precoated with silica gel (0.25 mm). TLC plates were visualized by exposure to UV light (UV), and then were stained by submersion into aqueous ceric ammonium molybdate (CAM) or ethanolic ninhydrin solution (Ninhydrin) followed by brief heating on hot plate. Flash column chromatography was performed using silica gel 60 (230-400 mesh, Merck) with the indicated solvents.

$^1$H and $^{13}$C spectra were recorded on Bruker Avance DPX-500 or Bruker Avance DPX-400 NMR spectrometers. $^1$H NMR spectra are represented as follows: chemical shift, multiplicity (s=singlet, d=doublet, t=triplet, q=quartet, m=multiplet, br=broad), integration, and coupling constant (J) in Hertz (Hz). $^1$H NMR chemical shifts are reported relative to CDCl$_3$ (7.26 ppm) and d$_4$-MeOD (3.30 ppm). $^{13}$C NMR was recorded relative to the central line of CDCl$_3$ (77.00 ppm) and d$_4$-MeOD (49.00 ppm). High resolution mass spectra were measured at the Keck Biotechnology Resource Laboratory of Yale University. Low resolution mass spectra were acquired on a Waters Micromass ZQ mass spectrometer or a Perkin-Elmer API 150 EX LCMS spectrometer.

Synthetic Experimental Procedures and Characterization Data

Compounds (2, 3, 4, 5, 6) and Control Compound (1).

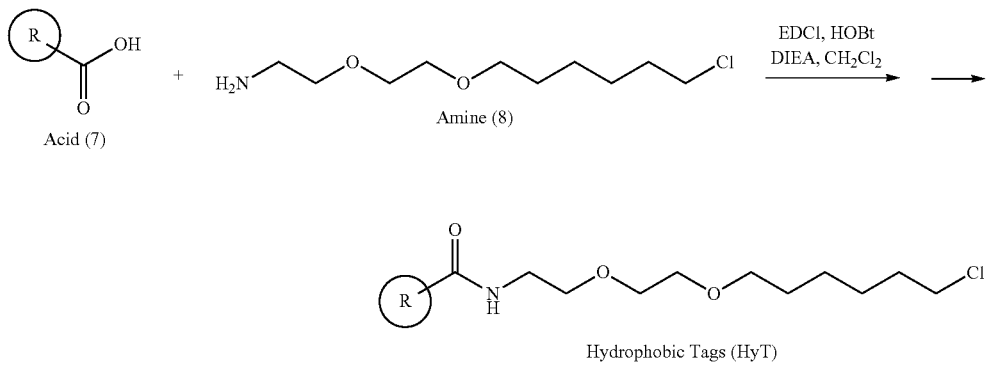

Scheme 1. General Synthetic Scheme for Hydrophobic Tags (Halotag)

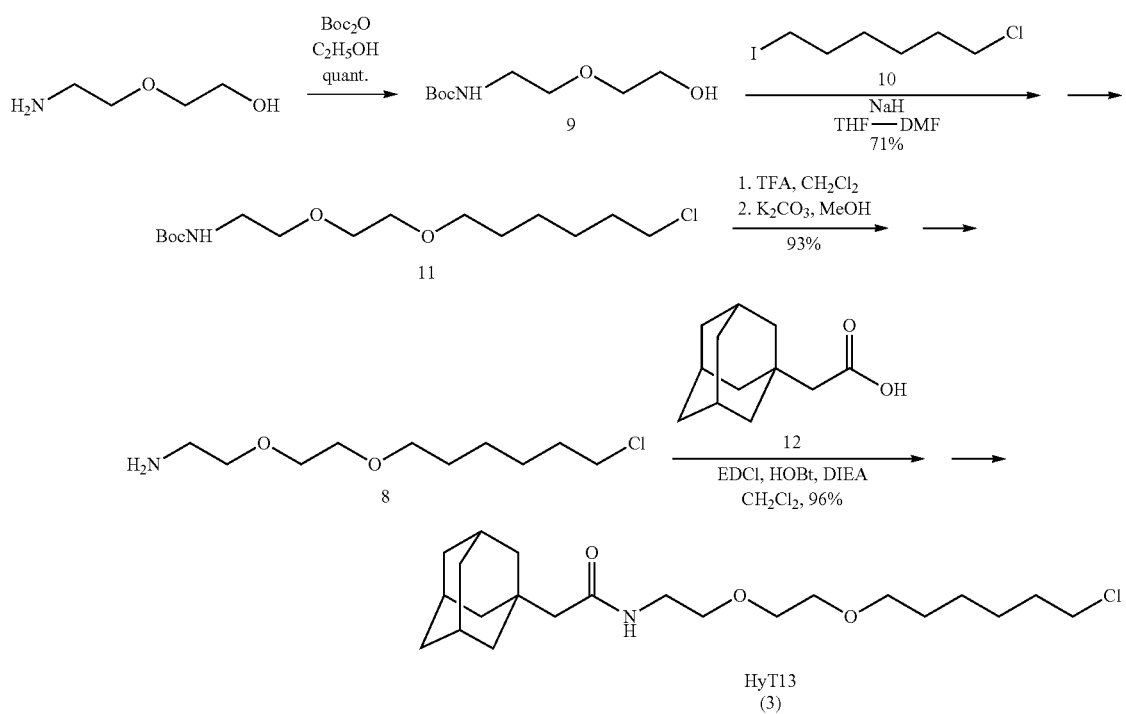

Scheme 2. Synthesis of HyT13 (3)

tert-Butyl (2-(2-hydroxyethoxy)ethyl)carbamate (9): To a solution of 2-(2-aminoethoxy)-ethanol (2.1 g, 20 mmol) in $C_2H_5OH$ (50 mL) at 0° C. was added $Boc_2O$ (4.36 g, 20 mmol). The reaction mixture was stirred at rt for 5 h, evaporated, and diluted with $CH_2Cl_2$ (20 mL) and $H_2O$ (20 mL). The mixture was extracted twice with $CH_2Cl_2$, and the combined extracts were washed with brine, dried over $Na_2SO_4$, filtered, and concentrated. The residue was chromatographed on silica gel to furnish tert-butyl (2-(2-hydroxyethoxy)ethyl)carbamate 9 (4.09 g, quant.). $^1$H NMR (400 MHz, $CDCl_3$) δ 5.01 (brs, 1H), 3.76-3.72 (m, 2H), 3.58-3.54 (m, 4H), 3.35-3.32 (m, 2H), 2.39 (t, J=5.9 Hz, 1H), 1.44 (s, 9H). $^{13}$C NMR (100 MHz, $CDCl_3$) δ 156.1, 79.3, 72.1, 70.3, 61.7, 40.3, 28.7. LRMS (ES+) $[M+Na]^+$ 228.4. TLC (33% EtOAc in hexanes), $R_f$ 0.08 (Ninhydrin).

tert-Butyl (2-(2-((6-chlorohexyl)oxy)ethoxy)ethyl)carbamate (11): To a solution of tert-butyl (2-(2-hydroxyethoxy)ethyl)carbamate 9 (2.15 g, 10.48 mmol) in THF (20 mL) and DMF (10 mL) at 0° C. added portionwise NaH (60% dispersion in mineral oil, 560 mg, 14.04 mmol). After stirring at 0° C. for 0.5 h, 6-chloro-1-iodohexane 10 (Sigma-Aldrich, 2.4 mL, 15.72 mmol) was added to the mixture at 0° C. The reaction mixture was stirred at 0° C. for 20 min, at rt for 14 h, and quenched at 0° C. with saturated $NH_4Cl$ solution in $H_2O$. The mixture was extracted twice with ethyl acetate and the combined extracts were washed with brine, dried over $Na_2SO_4$, filtered, and concentrated. The residue was chromatographed on silica gel to afford tert-butyl (2-(2-((6-chlorohexyl)oxy)ethoxy)ethyl) carbamate 11 (2.4 g, 71%). $^1$H NMR (400 MHz, $CDCl_3$) δ 4.98 (brs, 1H), 3.61-3.51 (m, 8H), 3.46 (t, J=6.7 Hz, 2H), 3.31 (t, J=4.7 Hz, 2H), 1.81-1.74 (m, 2H), 1.61-1.57 (m, 2H), 1.49-1.33 (m, 4H), 1.43 (s, 9H). $^{13}$C NMR (125 MHz, $CDCl_3$) δ 155.9, 79.2, 71.2, 70.3, 70.2, 70.0, 45.0, 32.5, 29.4, 28.4, 26.7, 25.4. LRMS (ES+) $[M+Na]^+$ 346.3. TLC (33% EtOAc in hexanes), $R_f$ 0.36 (Ninhydrin).

2-(2-((6-Chlorohexyl)oxy)ethoxy)ethanamine (8): To a solution of tert-butyl (2-(2-((6-chlorohexyl)oxy)ethoxy) ethyl)carbamate 11 (1.348 g, 4.171 mmol) in $CH_2Cl_2$ (30 mL) at 0° C. were added TFA (5 mL). After stirring at 0° C. for 2.5 h, TFA and solvent were removed in vacuo and the residue was diluted with MeOH (30 mL). The solution was cooled to 5° C. and $K_2CO_3$ (1.65 g, 11.929 mmol) was added to the mixture. The mixture was stirred at the same temperature for 10 min, filtered, and evaporated. The residue was diluted with $H_2O$ (20 mL) and the mixture was extracted four times with ethyl acetate. The combined extracts were dried over $Na_2SO_4$, filtered, and concentrated. The crude amine was purified by flash column chromatography on silica gel to give 2-(2-((6-chlorohexyl)oxy)ethoxy)ethanamine 8 (867 mg, 93%). $^1$H NMR (400 MHz, $CDCl_3$) δ 6.47 (brs, 1H), 3.69 (t, J=4.9 Hz, 2H), 3.63-3.60 (m, 2H), 3.56-3.53 (m, 2H), 3.52 (t, J=6.6 Hz, 2H), 3.44 (t, J=6.8 Hz, 2H), 3.12 (t, J=4.9 Hz, 2H), 1.79-1.71 (m, 2H), 1.60-1.53 (m, 2H), 1.46-1.39 (m, 2H), 1.36-1.28 (m, 2H). $^{13}$C NMR (100 MHz, $CDCl_3$) δ 71.1, 70.1, 69.7, 45.0, 39.4, 32.4, 29.1, 26.5, 25.1. LRMS (ES+) $[M+H]^+$ 223.8, $[M+Na]^+$246.1. TLC (10% $CH_3OH$ in EtOAc), $R_f$ 0.08 (CAM).

2-((3r,5r,7r)-Adamantan-1-yl)-N-(2-(2-((6-chlorohexyl) oxy)ethoxy)ethyl)acetamide (HyT13, 3): To a solution of 1-adamantaneacetic acid 12 (Sigma-Aldrich, 19.5 mg, 0.10 mmol, 1.0 equiv.) and 2-(2-((6-chlorohexyl)oxy)ethoxy) ethanamine 8 (23 mg, 0.10 mmol, 1.0 equiv.) in $CH_2Cl_2$ (1.5 mL) at rt were added HOBt (16 mg, 0.12 mmol, 1.2 equiv.) and DIEA (52 μL, 3.0 equiv.). The reaction mixture was cooled to 0° C. and EDCI (23 mg, 0.12 mmol, 1.2 equiv.) was added to the mixture. The resulting mixture was stirred at rt for 20 h and quenched at 0° C. with $H_2O$ (5 mL). The mixture was extracted twice with ethyl acetate and the combined extracts were washed with brine, dried over $Na_2SO_4$, filtered, and concentrated. The residue was chromatographed on silica gel to afford 3 (HyT13, 38 mg, 96%). $^1$H NMR (400 MHz, $CDCl_3$) δ 5.89 (brs, 1H), 3.61-3.59 (m, 2H), 3.57-3.50 (m 6H), 3.47-3.42 (m, 4H), 1.95 (s, 2H), 1.92 (s, 2H), 1.80-1.73 (m, 2H), 1.70-1.56 (m, 13H), 1.48-1.41 (m, 2H), 1.40-1.33 (m, 2H). $^{13}$C NMR (100 MHz, $CDCl_3$) δ 170.9, 71.2, 70.2, 69.9, 51.7, 45.0, 42.5, 38.9, 36.7, 32.7, 32.4, 29.4, 28.6, 26.6, 25.3. HRMS (ES+) calculated for $C_{22}H_{38}N_8ClNO_3$ $[M+H]^+$ 400.2613, found 400.2609. TLC (5% $CH_3OH$ in $CH_2Cl_2$), $R_f$ 0.29 (CAM).

N-(2-(2-((6-chlorohexyl)oxy)ethoxy)ethyl)-2,2-diphenylacetamide (HyT12, 2): HyT12 was synthesized by the same methods as HyT13 (3).

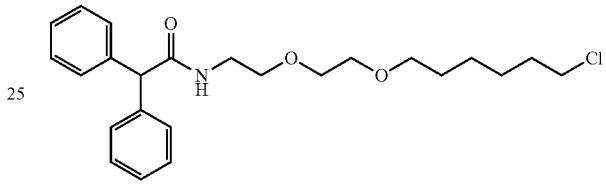

$^1$H NMR (400 MHz, $CDCl_3$) δ 7.35-7.24 (m, 10H), 6.15 (s, 1H), 4.91 (s, 1H), 3.56-3.47 (m, 10H), 3.42 (t, J=6.7 Hz, 2H), 1.80-1.73 (m, 2H), 1.62-1.55 (m, 2H), 1.48-1.41 (m, 2H), 1.39-1.31 (m, 2H). $^{13}$C NMR (100 MHz, $CDCl_3$) δ 171.8, 139.4, 128.8, 128.6, 127.1, 71.2, 70.2, 69.9, 69.6, 59.1, 45.0, 39.4, 32.4, 29.4, 26.6, 25.3. LRMS (ES+) $[M+H]^+$ 418.4. TLC (5% $CH_3OH$ in $CH_2Cl_2$), $R_f$ 0.33 (UV, CAM).

N-(2-(2-((6-chlorohexyl)oxy)ethoxy)ethyl)-2-(9H-fluoren-9-yl)acetamide (HyT16, 4): HyT16 was synthesized by the same methods as HyT13 (3).

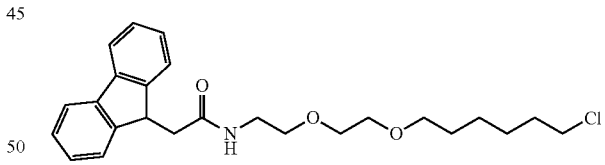

$^1$H NMR (400 MHz, $CDCl_3$) δ 7.75 (d, J=7.5 Hz, 2H), 7.50 (d, J=7.4 Hz, 2H), 7.38 (d, J=7.4 Hz, 1H), 7.36 (d, J=7.4 Hz, 1H), 7.29 (dd, J=7.4, 1.0 Hz, 1H), 7.28 (dd, J=7.4, 1.0 Hz, 1H), 6.0 (brs, 1H), 4.52 (t, J=7.4 Hz, 1H), 3.59-3.53 (m, 6H), 3.51-3.49 (m, 2H), 3.47 (t, J=6.7 Hz, 2H), 3.36 (t, J=6.7 Hz, 2H), 2.59 (d, J=7.4 Hz, 2H), 1.72-1.65 (m, 2H), 1.52-1.45 (m, 2H), 1.39-1.32 (m, 2H), 1.30-1.24 (m, 2H). $^{13}$C NMR (100 MHz, $CDCl_3$) δ 171.2, 146.4, 140.6, 127.3, 127.0, 124.5, 119.8, 71.1, 70.2, 69.8, 69.6, 45.0, 43.9, 40.9, 39.3, 32.4, 29.3, 26.5, 25.3. LRMS (ES+) $[M+H]^+$ 430.5. TLC (5% $CH_3OH$ in $CH_2Cl_2$), $R_f$ 0.36 (CAM).

N-(2-(2-((6-chlorohexyl)oxy)ethoxy)ethyl)-2,2-dicyclohexylacetamide (HyT21, 5): HyT21 was synthesized by the same methods as HyT13 (3).

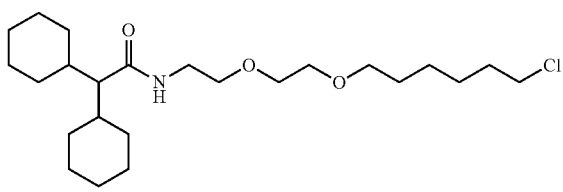 [SMILES: O=C(NCCOCCOCCCCCCCl)C(C1CCCCC1)C1CCCCC1]
¹H NMR (400 MHz, CDCl₃) δ 5.85 (s, 1H), 3.60-3.51 (m, 8H), 3.47-3.51 (m, 4H), 1.80-1.72 (m, 2H), 1.71-1.57 (m, 13H), 1.49-1.32 (m, 4H), 1.28-1.03 (m, 8H), 0.97-0.88 (m, 2H). ¹³C NMR (100 MHz, CDCl₃) δ 174.2, 71.2, 70.2, 70.1, 70.0, 59.4, 45.0, 38.7, 36.4, 32.5, 31.5, 29.6, 29.5, 26.7, 26.6, 26.5, 25.4. LRMS (ES+) [M+H]⁺ 430.6. TLC (5% CH₃OH in CH₂Cl₂), R_f 0.34 (CAM).
(S)—N-(2-(2-(6-chlorohexyl)oxy)ethoxy)ethyl)-2-(4-isobutylphenyl)propanamide (HyT22, 6): HyT22 was synthesized by the same methods as HyT13 (3).
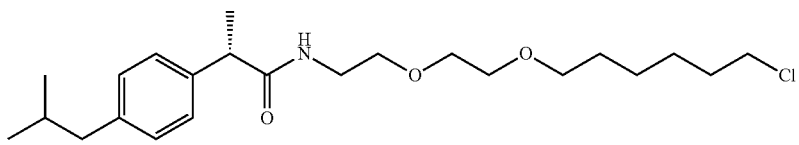 [SMILES: CC(C)Cc1ccc([C@H](C)C(=O)NCCOCCOCCCCCCCl)cc1]
¹H NMR (500 MHz, CDCl₃) δ 7.18 (d, J=8.0 Hz, 2H), 7.09 (d, J=8.0 Hz, 2H), 5.88 (s, 1H), 3.53-3.45 (m, 8H), 3.44-3.36 (m, 5H), 2.44 (d, J=7.2 Hz, 2H), 1.87-1.79 (m, 1H), 1.61-1.55 (m, 2H), 1.49 (d, J=7.2 Hz, 3H), 1.47-1.41 (m, 2H), 1.38-1.32 (m, 2H), 0.89 (d, J=6.6 Hz, 6H). ¹³C NMR (125 MHz, CDCl₃) δ 174.4, 140.5, 138.5, 129.4, 127.2, 71.2, 70.2, 69.9, 69.7, 46.7, 44.9, 39.2, 32.4, 30.1, 29.4, 26.6, 25.3, 22.3, 18.5. LRMS (ES+) [M+H]⁺ 412.6. TLC (10% CH₃OH in CH₂Cl₂), R_f 0.54 (UV, CAM).
Scheme 3. Synthesis of HyT5 (1)
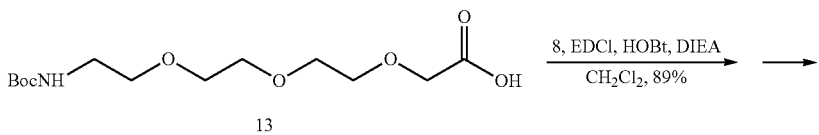
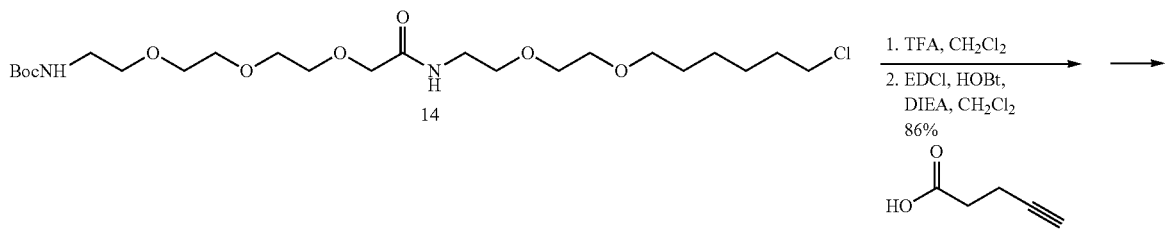
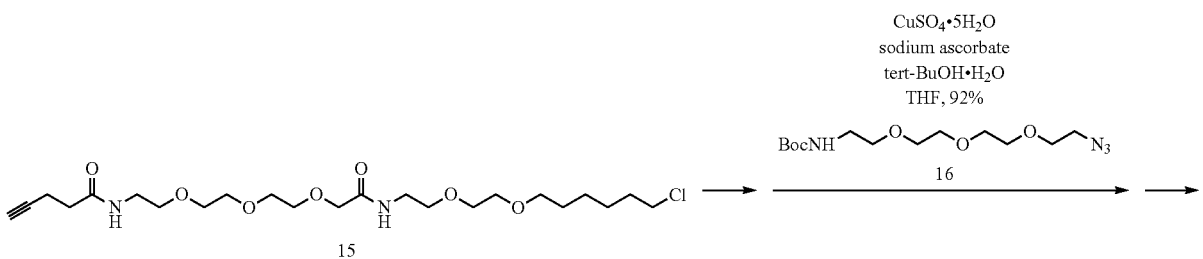

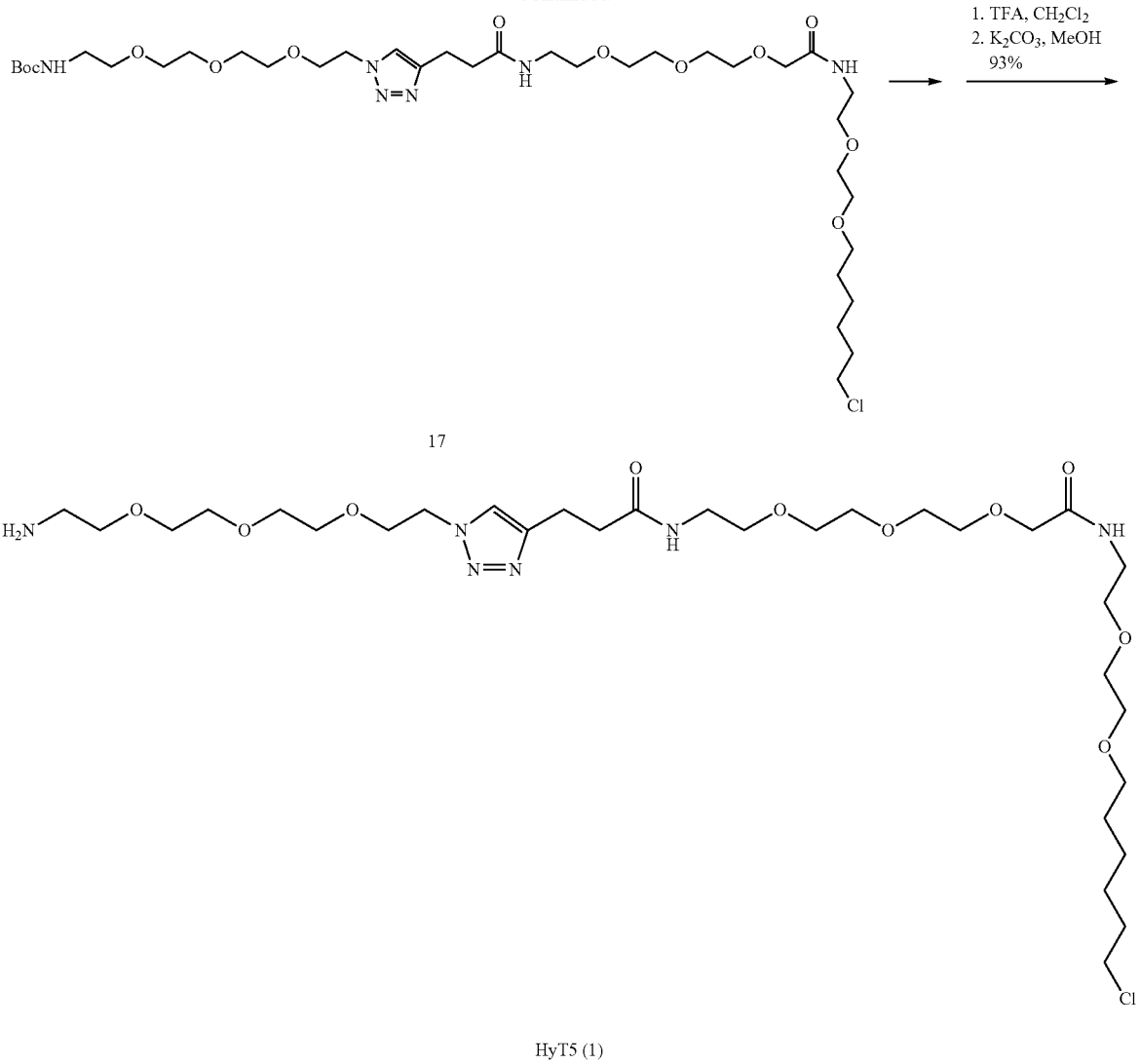

HyT5 (1)

tert-Butyl (24-chloro-11-oxo-3,6,9,15,18-pentaoxa-12-azatetracosyl)carbamate (14): To a solution of Boc-11-amino-3,6,9-trioxaundecanoic acid 13 (Peptides International Inc., Boc-mini-PEG-3, 200 mg, 0.650 mmol) and 2-(2-((6-chlorohexyl)oxy)ethoxy)ethanamine 8 (145 mg, 0.650 mmol) in $CH_2Cl_2$ (4.5 mL) at rt were added HOBt (105 mg, 0.780 mmol) and DIEA (280 μL, 1.625 mmol). The mixture was cooled to 0° C. and EDCI (150 mg, 0.780 mmol) was added to the mixture. The resulting mixture was allowed to rt, stirred at rt for 20 h, and quenched at 0° C. with $H_2O$ (10 mL). The mixture was extracted twice with ethyl acetate and the combined extracts were washed with brine, dried over $Na_2SO_4$, filtered, and concentrated. The residue was chromatographed on silica gel to afford tert-butyl (24-chloro-11-oxo-3,6,9,15,18-pentaoxa-12-azatetracosyl)carbamate 14 (296 mg, 89%). $^1H$ NMR (400 MHz, $CDCl_3$) δ 7.18 (brs, 1H), 5.13 (brs, 1H), 4.00 (s, 2H), 3.69-3.47 (m, 20H), 3.43 (t, J=6.7 Hz, 2H), 3.31-3.28 (m, 2H), 1.79-1.72 (m, 2H), 1.61-1.54 (m, 2H), 1.47-1.40 (m, 2H), 1.42 (s, 9H), 1.38-1.32 (m, 2H). $^{13}C$ NMR (100 MHz, $CDCl_3$) δ 169.9, 155.9, 79.1, 71.2, 70.8, 70.5, 70.4, 70.2, 70.1, 69.9, 69.7, 45.0, 40.2, 38.5, 32.4, 29.4, 28.3, 26.6, 25.3. LRMS (ES+) $[M+H]^+$ 535.5. TLC (10% $CH_3OH$ in $CH_2Cl_2$), $R_f$ 0.48 (CAM).

N-(24-Chloro-11-oxo-3,6,9,15,18-pentaoxa-12-azatetracosyl)pent-4-ynamide (15): To a stirred solution of tert-butyl (24-chloro-11-oxo-3,6,9,15,18-pentaoxa-12-azatetracosyl)carbamate 14 (170 mg, 0.332 mmol) in $CH_2Cl_2$ (2.5 mL) at 0° C. was added TFA (0.5 mL). The reaction mixture was stirred at 0° C. for 2.5 h and concentrated. The crude amine was used for the next reaction without further purification.

To a solution of crude amine (0.330 mmol) and 4-pentynoic acid (32 mg, 0.330 mmol) in $CH_2Cl_2$ (2.5 mL) at rt were added HOBt (54 mg, 0.396 mmol) and DIEA (150 μL, 0.825 mmol). The mixture was cooled to 0° C. and EDCI (76 mg, 0.396 mmol) was added to the mixture. The resulting mixture was allowed to rt, stirred at rt for 17 h, and quenched at 0° C. with $H_2O$ (5 mL). The mixture was extracted three times with ethyl acetate and the combined extracts were washed with brine, dried over $Na_2SO_4$, filtered, and concentrated. The residue was chromatographed on silica gel to provide N-(24-chloro-11-oxo-3,6,9,15,18-pentaoxa-12-azatetracosyl)pent-4-ynamide 15 (140 mg, 86%). $^1H$ NMR (400

MHz, CDCl$_3$) δ 7.18 (brs, 1H), 6.71 (brs, 1H), 4.02 (s, 2H), 3.70-3.64 (m, 4H), 3.63-3.59 (m, 6H), 3.57-3.54 (m, 6H), 3.53-3.48 (m, 4H), 3.47-3.42 (m, 4H), 2.54-2.49 (m, 2H), 2.43-2.39 (m, 2H), 1.99 (t, J=2.6 Hz, 1H), 1.80-1.72 (m, 2H), 1.62-1.55 (m, 2H), 1.48-1.40 (m, 2H), 1.39-1.31 (m, 2H). $^{13}$C NMR (100 MHz, CDCl$_3$) δ 171.2, 170.3, 83.1, 71.2, 70.6, 70.5, 70.3, 70.2, 70.1, 70.0, 69.9, 69.7, 69.1, 45.0, 39.3, 38.6, 35.0, 32.4, 29.4, 26.6, 25.3, 14.8. LRMS (ES+) [M+H]$^+$ 515.62. TLC (5% CH$_3$OH in CH$_2$Cl$_2$), R$_f$ 0.42 (UV, CAM).

tert-Butyl (2-(2-(2-(2-azidoethoxy)ethoxy)ethoxy)ethyl) carbamate (16): To a solution of 11-azido-3,6,9-trioxaundecan-1-amine (Fluka, 370 mg, 1.695 mmol) in C$_2$H$_5$OH (3.5 mL) at 0° C. was added Boc$_2$O (370 mg, 1.695 mmol). The reaction mixture was stirred at rt for 12 h and evaporated. The residue was diluted with CH$_2$Cl$_2$ (5 mL) & H$_2$O (5 mL) and the mixture was extracted twice with CH$_2$Cl$_2$. The combined extracts were washed with brine, dried over Na$_2$SO$_4$, filtered, and concentrated. The crude residue was purified by flash chromatography on silica gel to provide tert-butyl (2-(2-(2-(2-azidoethoxy)ethoxy)ethoxy)ethyl)carbamate 16 (518 mg, 96%). $^1$H NMR (400 MHz, CDCl$_3$) δ 5.01 (s, 1H), 3.69-3.59 (m, 10H), 3.53 (t, J=5.1 Hz, 2H), 3.38 (t, J=5.1 Hz, 2H), 3.32-3.29 (m, 2H), 1.43 (s, 9H). TLC (10% CH$_3$OH in CH$_2$Cl$_2$), R$_f$ 0.49 (CAM).

tert-Butyl (2-(2-(2-(2-(4-(28-chloro-3,15-dioxo-7,10,13,19,22-pentaoxa-4,16-diazaoctacos yl)-1H-1,2,3-triazol-1-yl)ethoxy)ethoxy)ethoxy)ethyl)carbamate (17): To a solution of tert-butyl (2-(2-(2-(2-azidoethoxy)ethoxy)ethoxy) ethyl)carbamate 16 (37 mg, 0.116 mmol) and N-(24-chloro-11-oxo-3,6,9,15,18-pentaoxa-12-azatetracosyl)pent-4-ynamide 15 (57 mg, 0.116 mmol) in t-BuOH—H$_2$O (1:1, 0.5 mL) and THF (0.5 mL) at rt were added CuSO$_4$.5H$_2$O (3 mg, 0.012 mmol) and sodium ascorbate (1.0 M in H$_2$O, 3 drops). The reaction mixture was stirred at rt for 22 h and evaporated. The residue was diluted with H$_2$O (5 mL) and the mixture was extracted three times with ethyl acetate. The combined extracts were washed with brine, dried over Na$_2$SO$_4$, filtered, and concentrated. The crude residue was purified by flash chromatography on silica gel to give tert-butyl (2-(2-(2-(2-(4-(28-chloro-3,15-dioxo-7,10,13,19,22-pentaoxa-4,16-diazaoctacosyl)-1H-1,2,3-triazol-1-yl) ethoxy) ethoxy)ethoxy)ethyl)carbamate 17 (86 mg, 92%). $^1$H NMR (400 MHz, CDCl$_3$) δ 7.54 (s, 1H), 7.17 (brs, 1H), 6.60 (brs, 1H), 5.11 (brs, 1H), 4.49 (t, J=5.1 Hz, 2H), 4.02 (s, 2H), 3.84 (t, J=5.1 Hz, 2H), 3.70-3.38 (m, 34H), 3.31-3.28 (m, 2H), 3.03 (t, J=7.4 Hz, 2H), 2.61 (t, J=5.1 Hz, 2H), 1.79-1.72 (m, 2H), 1.61-1.54 (m, 2H), 1.47-1.40 (m, 2H), 1.42 (s, 9H), 1.39-1.31 (m, 2H). $^{13}$C NMR (100 MHz, CDCl$_3$) δ 172.0, 170.1, 155.9, 146.3, 122.6, 79.1, 77.2, 71.2, 70.65, 70.62, 70.54, 70.51, 70.47, 70.42, 70.3, 70.2, 70.16, 70.14, 69.9, 69.8, 69.7, 69.4, 50.1, 45.0, 40.2, 39.2, 38.5, 35.5, 32.4, 29.4, 28.4, 26.6, 25.3, 21.4. LRMS (ES+) [M+Na]$^+$833.48. TLC (5% CH$_3$OH in CH$_2$Cl$_2$), R$_f$ 0.25 (CAM).

3-(1-(2-(2-(2-(2-aminoethoxy)ethoxy)ethoxy)ethyl)-1H-1,2,3-triazol-4-yl)-N-(24-chloro-11-oxo-3,6,9,15,18-pentaoxa-12-azatetracosyl)propanamide (HyT5, 1): To a solution of tert-butyl (2-(2-(2-(2-(4-(28-chloro-3,15-dioxo-7,10,13,19,22-pentaoxa-4,16-diazaoctacosyl)-1H-1,2,3-triazol-1-yl)ethoxy)ethoxy)ethoxy)ethyl) carbamate 17 (30 mg, 0.037 mmol) in CH$_2$Cl$_2$ (2.0 mL) at 0° C. were added TFA (0.5 mL). After stirring at 0° C. for 2.5 h, TFA and solvent were removed in vacuo and the residue was diluted with MeOH (0.5 mL). The solution was cooled to 5° C. and K$_2$CO$_3$ (26 mg, 0.185 mmol) was added to the mixture. The mixture was stirred at the same temperature for 30 min and extracted three times with ethyl acetate. The combined extracts were washed with brine, dried over Na$_2$SO$_4$, filtered, and concentrated. The crude residue was purified by flash chromatography on silica gel to give the proposed structure of 3-(1-(2-(2-(2-(2-aminoethoxy)ethoxy)ethoxy) ethyl)-1H-1,2,3-triazol-4-yl)-N-(24-chloro-11-oxo-3,6,9,15, 18-penta oxa-12-azatetracosyl)propanamide 1 (HyT5, 24.5 mg, 93%). $^1$H NMR (400 MHz, CD$_3$OD) δ 7.77 (s, 1H), 4.53 (t, J=5.1 Hz, 2H), 3.99 (s, 2H), 3.86 (t, J=5.1 Hz, 2H), 3.70-3.50 (m, 28H), 3.46 (t, J=6.5 Hz, 2H), 3.41 (t, J=5.6 Hz, 2H), 3.35 (t, J=5.4 Hz, 2H), 3.12 (t, J=5.0 Hz, 2H), 2.98 (t, J=7.5 Hz, 2H), 2.56 (t, J=7.6 Hz, 2H), 1.79-1.72 (m, 2H), 1.61-1.54 (m, 2H), 1.49-1.43 (m, 2H), 1.42-1.35 (m, 2H). $^{13}$C NMR (100 MHz, CD$_3$OD) δ 174.6, 172.7, 147.6, 124.1, 72.1, 71.8, 71.5, 71.4, 71.37, 71.33, 71.29, 71.22, 71.1, 70.6, 70.47, 70.40, 67.9, 51.2, 45.7, 40.6, 40.3, 39.8, 36.2, 33.7, 30.5, 27.7, 26.5, 22.5. LRMS (ES+) [M+H]$^+$ 711.36, [M+Na]$^+$733.36. TLC (10% CH$_3$OH in CH$_2$Cl$_2$), R$_f$ 0.09 (Ninhydrin, CAM).

Scheme 4. Synthesis of HyT6 (20)

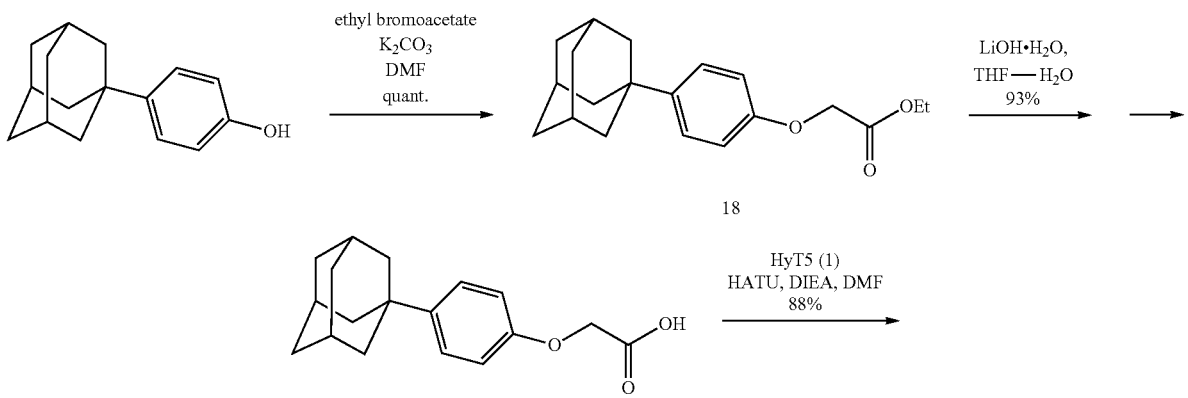

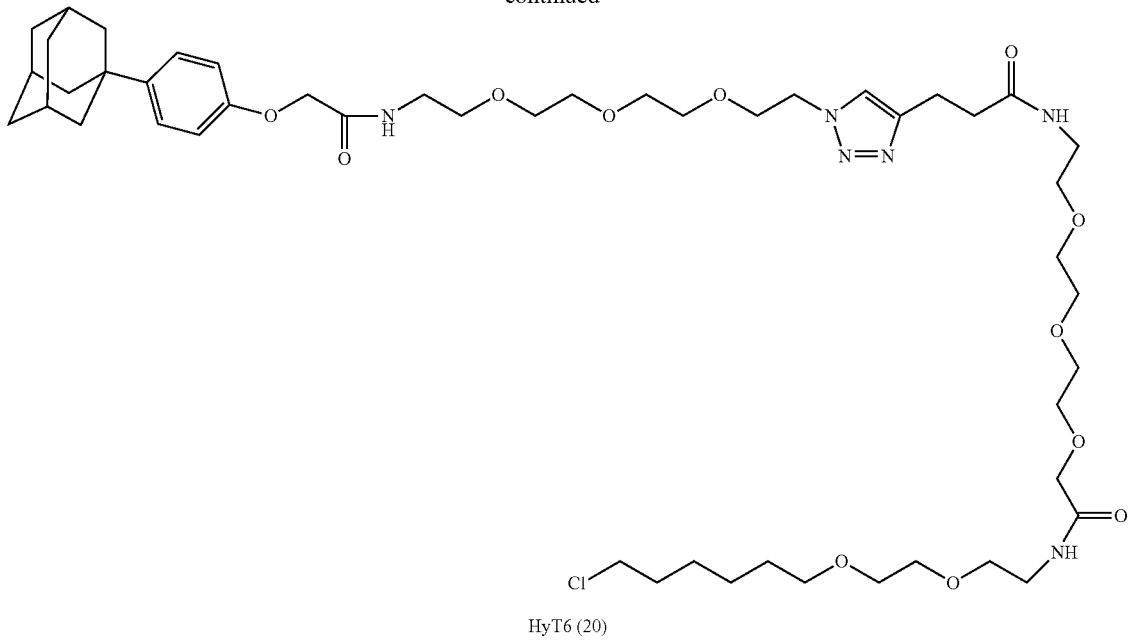

HyT6 (20)

(4-Adamantan-1-yl-phenoxy) acetic acid ethyl ester (18): To a solution of 4-(1-adamantyl)phenol (250 mg, 1.095 mmol) in DMF (2 mL) at rt were added ethyl bromoacetate (150 μL, 1.314 mmol) and K$_2$CO$_3$ (454 mg, 3.285 mmol). The reaction mixture was stirred at rt for 20 h and diluted with H$_2$O (10 mL) and ethyl acetate (10 mL). The mixture was extracted twice with ethyl acetate and the extracts were washed with sat. NaHCO$_3$ and brine. The combined organic layers were dried over Na$_2$SO$_4$, filtered, and concentrated. The crude residue was purified by flash chromatography on silica gel to give (4-adamantan-1-yl-phenoxy) acetic acid ethyl ester 18 (335 mg, quant.) as a white solid. $^1$H NMR (500 MHz, CDCl$_3$) δ 7.27 (d, J=8.7 Hz, 2H), 6.86 (d, J=8.7 Hz, 2H), 4.59 (s, 2H), 4.27 (q, J=7.1 Hz, 2H), 2.08 (s, 3H), 1.87 (d, J=2.4 Hz, 6H), 1.79-1.71 (m, 6H), 1.30 (t, J=7.0 Hz, 3H). $^{13}$C NMR (125 MHz, CDCl$_3$) δ 169.1, 155.6, 144.7, 125.9, 114.1, 65.5, 61.2, 43.3, 36.7, 35.6, 28.9, 14.1. TLC (10% CH$_3$OH in CH$_2$Cl$_2$), R$_f$ 0.48 (UV, CAM).

(4-Adamantan-1-yl-phenoxy) acetic acid (19): To a solution of ester 18 (290 mg, 0.923 mmol) in THF-H$_2$O (3 mL/3 mL) at rt was added LiOH.H$_2$O (454 mg, 3.285 mmol). The reaction mixture was stirred at rt for 15 h and THF was removed in vacuo. The aqueous mixture was diluted with H$_2$O (5 mL), cooled to 0° C., and adjusted to pH 4 with 1N—HCl. The mixture was extracted twice with ethyl acetate and the extracts were washed with brine. The combined organin layers were dried over Na$_2$SO$_4$, filtered, and concentrated. The crude residue was solidified with hexanes and the solid was filtered with hexanes and dried in vacuo to furnish (4-adamantan-1-yl-phenoxy) acetic acid 19 (246 mg, 93%) as a white solid. $^1$H NMR (400 MHz, CD$_3$OD) δ 7.26 (d, J=8.8 Hz, 2H), 6.84 (d, J=8.8 Hz, 2H), 4.60 (s, 2H), 2.05 (s, 3H), 1.89 (s, 6H), 1.83-1.75 (m, 6H).

3-(1-(1-(4-((3r,5r,7r)-Adamantan-1-yl)phenoxy)-2-oxo-6,9,12-trioxa-3-azatetradecan-14-yl)-1H-1,2,3-triazol-4-yl)-N-(24-chloro-11-oxo-3,6,9,15,18-pentaoxa-12-azatetracosyl)propanamide (HyT6, 20): To a solution of (4-adamantan-1-yl-phenoxy) acetic acid 19 (6.3 mg, 0.022 mmol) in DMF (0.5 mL) at rt were added HATU (10 mg, 0.027 mmol) and DIEA (10 μL, 0.055 mmol). The mixture was stirred at rt for 0.5 h and a solution of HyT5 1 (16.5 mg, 0.023 mmol) in DMF (0.5 mL) was added to the mixture. The resulting mixture was stirred at rt for 22 h, and quenched at 0° C. with H$_2$O (5 mL). The mixture was extracted three times with ethyl acetate and the combined extracts were washed with brine, dried over Na$_2$SO$_4$, filtered, and concentrated. The residue was chromatographed on silica gel to provide HyT6 20 (19 mg, 88%). $^1$H NMR (500 MHz, CD$_3$OD) δ 7.74 (s, 1H), 7.26 (d, J=8.8 Hz, 2H), 6.87 (d, J=8.8 Hz, 2H), 5.46 (s, 1H), 4.46 (t, J=4.9 Hz, 2H), 4.45 (s, 2H), 3.98 (s, 2H), 3.80 (t, J=5.1 Hz, 2H), 3.65 (s, 4H), 3.63-3.61 (m, 2H), 3.59-3.51 (m, 20H), 3.49 (t, J=5.5 Hz, 2H), 3.45-3.42 (m, 4H), 3.39 (t, J=5.5 Hz, 2H), 3.32 (t, J=5.2 Hz, 2H), 2.95 (t, J=7.6 Hz, 2H), 2.52 (t, J=7.6 Hz, 2H), 2.04 (s, 3H), 1.86 (d, J=2.3 Hz, 6H), 1.80-1.70 (m, 8H), 1.57-1.52 (m, 2H), 1.46-1.40 (m, 2H), 1.38-1.32 (m, 2H). $^{13}$C NMR (125 MHz, CD$_3$OD) δ 174.7, 127.0, 124.2, 115.4, 72.2, 71.8, 71.6, 71.5, 71.4, 71.32, 71.30, 71.2, 71.1, 70.8, 70.5, 70.4, 51.3, 45.7, 44.5, 40.3, 39.9, 39.8, 37.8, 36.7, 36.3, 33.7, 30.5, 30.4, 27.7, 26.5, 22.5. HRMS (ES+) calculated for C$_{49}$H$_{80}$N$_6$O$_{12}$Cl [M+H]$^+$ 979.5523, found 979.5529. TLC (10% CH$_3$OH in CH$_2$Cl$_2$), R$_f$ 0.51 (UV, CAM).

Scheme 5. Synthesis of HyT7 (21)

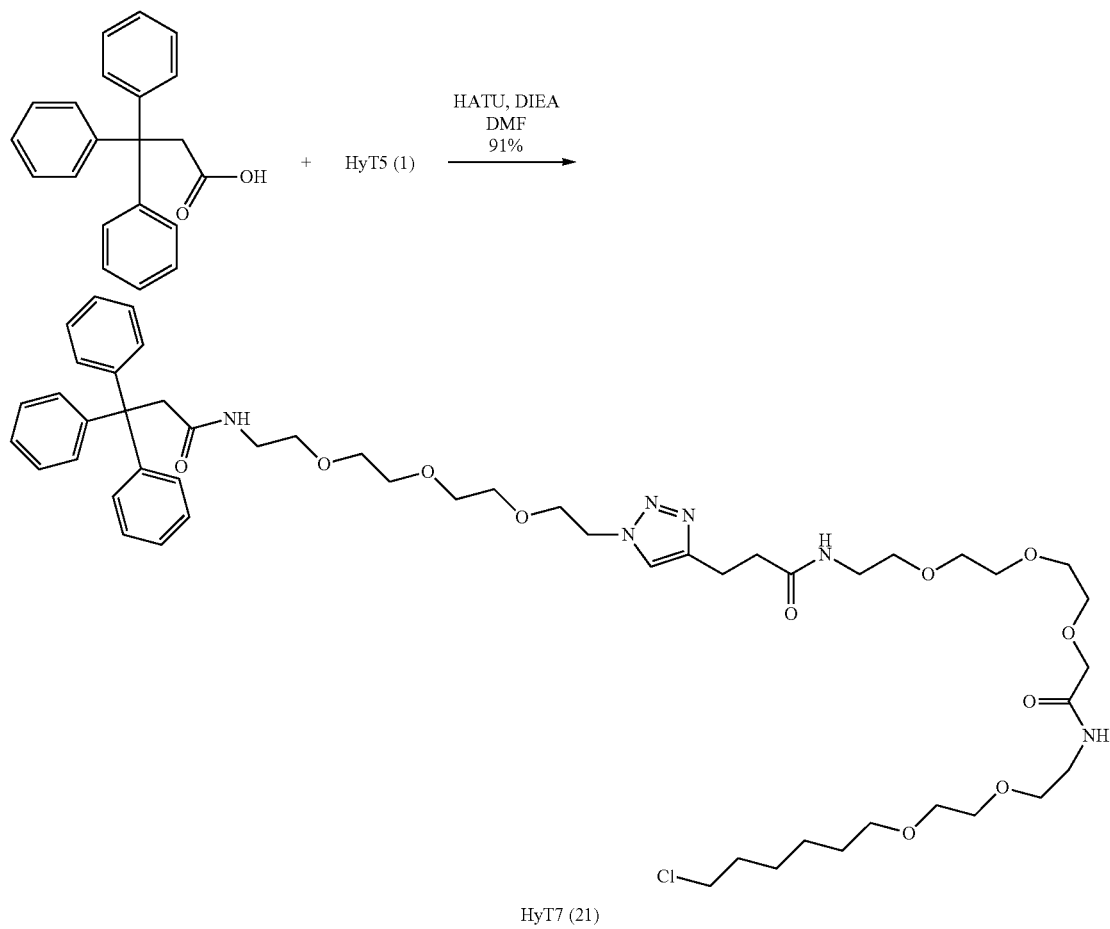

HyT7 (21)

To a solution of 3,3,3-triphenyl propionic acid (11.3 mg, 0.0373 mmol) in DMF (0.5 mL) at rt were added HATU (17 mg, 0.0447 mmol) and DIEA (16 μL, 0.0932 mmol). The mixture was stirred at rt for 0.5 h and a solution of HyT5 1 (28 mg, 0.0392 mmol) in DMF (0.5 mL) was added to the mixture. The resulting mixture was stirred at rt for 20 h, and quenched at 0° C. with H$_2$O (6 mL). The mixture was extracted three times with ethyl acetate and the combined extracts were washed with brine, dried over Na$_2$SO$_4$, filtered, and concentrated. The residue was chromatographed on silica gel to afford N-(2-(2-(2-(2-(4-(28-chloro-3,15-dioxo-7,10,13,19,22-pentaoxa-4,16-diazaocta cosyl)-1H-1,2,3-triazol-1-yl)ethoxy)ethoxy)ethoxy)ethyl)-3,3,3-triphenylpropanamide 21 (HyT7, 33.5 mg, 91%). $^1$H NMR (500 MHz, CD$_3$OD) δ 7.75 (s, 1H), 7.37 (brs, 1H), 7.27-7.20 (m, 12H), 7.16-7.13 (m, 3H), 4.47 (t, J=5.0 Hz, 2H), 4.00 (s, 2H), 3.82 (t, J=5.0 Hz, 2H), 3.68-3.47 (m, 26H), 3.46-3.40 (m, 6H), 3.34 (t, J=5.1 Hz, 2H), 3.15 (t, J=5.2 Hz, 2H), 3.03-3.01 (m, 2H), 2.96 (t, J=7.5 Hz, 2H), 2.54 (t, J=7.3 Hz, 2H), 1.77-1.71 (m, 2H), 1.58-1.53 (m, 2H), 1.46-1.41 (m, 2H), 1.38-1.34 (m, 2H). $^{13}$C NMR (125 MHz, CD$_3$OD) δ 174.7, 172.9, 172.7, 148.3, 147.5, 130.5, 128.7, 127.1, 124.2, 72.1, 71.7, 71.4, 71.36, 71.33, 71.2, 71.18, 71.13, 70.9, 70.4, 70.3, 70.2, 57.5, 51.2, 48.1, 45.7, 40.3, 40.0, 39.8, 36.3, 33.7, 30.5, 27.7, 26.4, 22.4. HRMS (ES+) calculated for C$_{52}$H$_{76}$N$_6$O$_{11}$Cl [M+H]$^+$ 995.5261, found 995.5265. TLC (10% CH$_3$OH in CH$_2$Cl$_2$), R$_f$ 0.62 (UV, CAM).

N-(2-(2-((6-Chlorohexyl)oxy)ethoxy)ethyl)-3,3,3-triphenylpropanamide (HyT8, 22): HyT8 was synthesized by the same methods as HyT13 (3).

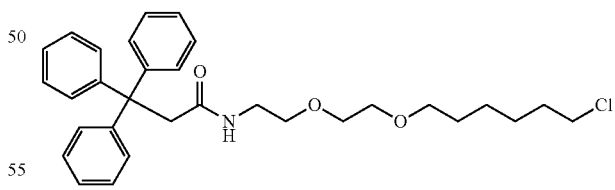

$^1$H NMR (400 MHz, CDCl$_3$) δ 7.31-7.26 (m, 12H), 7.23-7.19 (m, 3H), 5.36 (brs, 1H), 3.58 (s, 2H), 3.53 (t, J=6.7 Hz, 2H), 3.48-3.46 (m, 2H), 3.45-3.41 (m, 4H), 3.22-3.20 (m, 2H), 3.16-3.13 (m, 2H), 1.81-1.74 (m, 2H), 1.63-1.56 (m, 2H), 1.49-1.42 (m, 2H), 1.40-1.32 (m, 2H). $^{13}$C NMR (100 MHz, CDCl$_3$) δ 170.3, 146.3, 129.1, 127.9, 126.2, 71.2, 70.0, 69.8, 69.3, 56.1, 48.4, 45.0, 38.9, 32.4, 29.3, 26.6, 25.3. HRMS (ES+) calculated for C$_{31}$H$_{39}$NO$_3$Cl [M+H]$^+$ 508.2618, found 508.2617. TLC (10% CH$_3$OH in CH$_2$Cl$_2$), R$_f$ 0.69 (UV, CAM).

Supplementary Scheme 6. Synthesis of HyT9 (24)

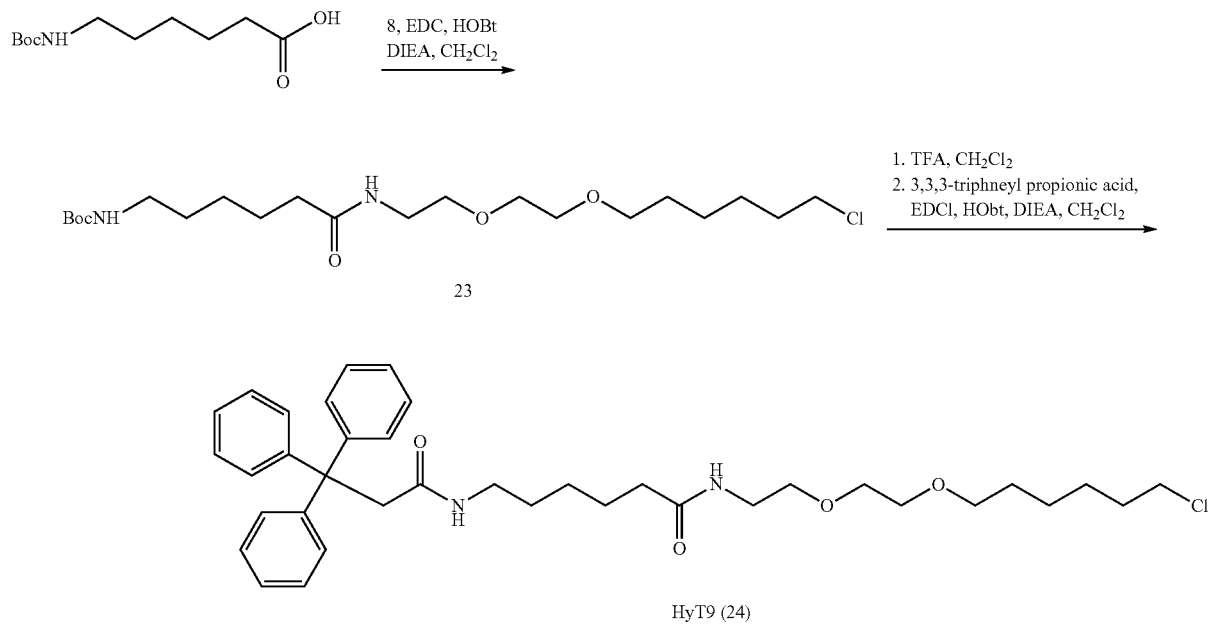

HyT9 (24)

tert-Butyl (6-((2-(2-(((6-chlorohexyl)oxy)ethoxy)ethyl)amino)-6-oxohexyl)carbamate 23: To a solution of 6-(Boc-amino)-caproic acid (28 mg, 0.121 mmol) and amine 8 (27 mg, 0.121 mmol) in $CH_2Cl_2$ (1.5 mL) at rt were added HOBt (20 mg, 0.145 mmol, 1.2 equiv.) and DIEA (63 µL, 0.363 mmol). The reaction mixture was cooled to 0° C. and EDCI (28 mg, 0.145 mmol, 1.2 equiv.) was added to the mixture. The resulting mixture was stirred at rt for 20 h and quenched at 0° C. with $H_2O$ (5 mL). The mixture was extracted twice with ethyl acetate and the combined extracts were washed with brine, dried over $Na_2SO_4$, filtered, and concentrated. The residue was chromatographed on silica gel to afford tert-Butyl (6-((2-(2-(((6-chlorohexyl)oxy)ethoxy)ethyl)amino)-6-oxohexyl)carbamate 23 (45 mg, 85%). $^1$H NMR (400 MHz, $CDCl_3$) δ 6.09 (s, 1H), 4.59 (s, 1H), 3.60-3.49 (m, 8H), 3.46-3.40 (m, 4H), 2.15 (t, J=7.4 Hz, 2H), 1.78-1.71 (m, 2H), 1.66-1.55 (m, 4H), 1.50-1.39 (m, 4H), 1.41 (s, 9H), 1.37-1.27 (m, 2H). $^{13}$C NMR (100 MHz, $CDCl_3$) δ 172.8, 155.9, 79.0, 71.2, 70.1, 69.9, 69.7, 44.9, 39.0, 36.4, 32.4, 29.7, 29.3, 28.3, 26.6, 26.3, 25.3, 25.2. TLC (10% $CH_3OH$ in $CH_2Cl_2$), $R_f$ 0.46 (UV, CAM).

N-(2-(2-(((6-Chlorohexyl)oxy)ethoxy)ethyl)-6-(3,3,3-triphenylpropanamido)hexanamide (HyT9, 24): To a stirred solution of tert-Butyl (6-((2-(2-(((6-chlorohexyl)oxy)ethoxy)ethyl)amino)-6-oxohexyl) carbamate 23 (30 mg, 0.0687 mmol) in $CH_2Cl_2$ (1.5 mL) at 0° C. was added TFA (0.5 mL). The reaction mixture was stirred at 0° C. for 2.0 h and concentrated. The crude amine was used for the next reaction without further purification.

To a solution of crude amine and 3,3,3-triphenyl propionic acid (20 mg, 0.068 mmol) in $CH_2Cl_2$ (1.0 mL) at rt were added HOBt (11 mg, 0.0816 mmol) and DIEA (36 µL, 0.204 mmol). The mixture was cooled to 0° C. and EDCI (16 mg, 0.0816 mmol) was added to the mixture. The resulting mixture was allowed to rt, stirred at rt for 17 h, and quenched at 0° C. with $H_2O$ (3 mL). The mixture was extracted three times with ethyl acetate and the combined extracts were washed with brine, dried over $Na_2SO_4$, filtered, and concentrated. The residue was chromatographed on silica gel to provide 24 (HyT9, 35 mg, 83%). $^1$H NMR (500 MHz, $CD_3OD$) δ 7.89 (s, 1H), 7.23-7.16 (m, 13H), 7.12-7.09 (m, 3H), 3.55-3.45 (m, 10H), 3.42 (t, J=6.5 Hz, 2H), 3.30-3.28 (m, 2H), 2.80-2.78 (m, 2H), 2.07 (t, J=7.2 Hz, 2H), 1.73-1.67 (m, 2H), 1.56-1.50 (m, 2H), 1.45-1.37 (m, 4H), 1.36-1.31 (m, 2H), 1.11-1.09 (m, 2H), 1.05-1.02 (m, 2H). $^{13}$C NMR (125 MHz, $CD_3OD$) δ 176.1, 172.9, 172.8, 148.3, 130.6, 128.6, 127.1, 72.2, 71.2, 71.1, 70.6, 57.6, 48.2, 40.3, 40.0, 36.8, 33.7, 30.5, 29.7, 27.7, 27.4, 26.5, 26.4. HRMS (ES+) calculated for $C_{37}H_{50}N_2O_4Cl$ [M+H]$^+$ 621.3459, found 621.3460. TLC (10% $CH_3OH$ in $CH_2Cl_2$), $R_f$ 0.48 (UV, CAM).

N-(24-chloro-11-oxo-3,6,9,15,18-pentaoxa-12-azatetracosyl)-3,3,3-triphenylpropanamide (HyT10, 25): HyT10 was synthesized by the similar methods as HyT9.

Supplementary Scheme 7. Synthesis of HyT10 (25)

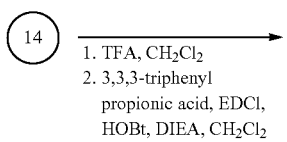

1. TFA, $CH_2Cl_2$
2. 3,3,3-triphenyl propionic acid, EDCl, HOBt, DIEA, $CH_2Cl_2$

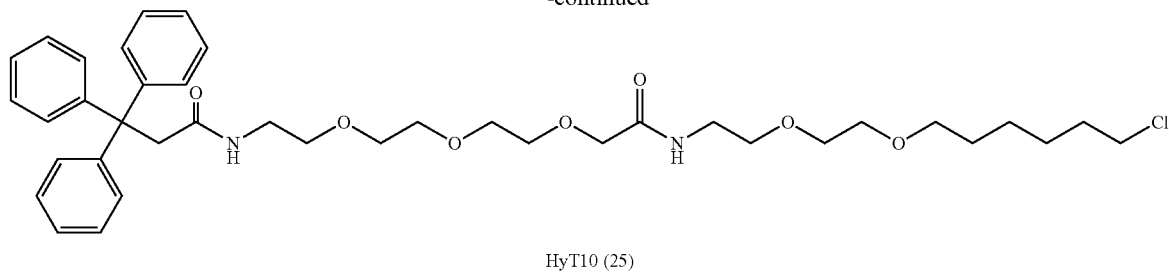

HyT10 (25)

¹H NMR (400 MHz, CDCl₃) δ 7.29-7.17 (m, 15H), 7.12 (s, 1H), 5.68 (s, 1H), 4.00 (s, 2H), 3.66-3.64 (m, 2H), 3.62-3.60 (m, 2H), 3.59-3.57 (m, 4H), 3.55-3.51 (m, 8H), 3.20-3.17 (m, 2H), 3.15-3.13 (m, 2H), 1.80-1.73 (m, 2H), 1.62-1.55 (m, 2H), 1.49-1.41 (m, 2H), 1.39-1.32 (m, 2H). ¹³C NMR (100 MHz, CDCl₃) δ 170.5, 170.1, 146.5, 129.2, 127.9, 126.2, 71.2, 70.6, 70.5, 70.4, 70.3, 70.2, 69.9, 69.7, 69.5, 56.1, 48.1, 45.0, 39.0, 38.5, 32.4, 29.4, 26.6, 25.3. HRMS (ES+) calculated for C₃₉H₅₄N₂O₇Cl [M+H]⁺ 697.3620, found 697.3622. TLC (10% CH₃OH in CH₂Cl₂), R_f 0.43 (UV, CAM).

(S)—N-(2-(2-(6-Chlorohexyl)oxy)ethoxy)ethyl)-2-(3,4,5-trimethoxyphenyl)butanamide (HyT11, 26): HyT11 was synthesized by the same methods as HyT13 (3).

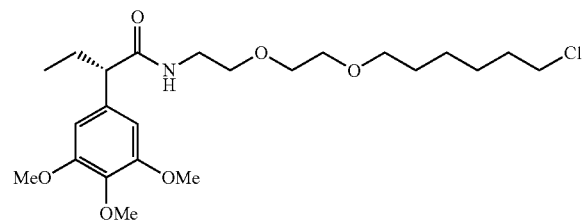 [SMILES: CC[C@H](C(=O)NCCOCCOCCCCCCCl)c1cc(OC)c(OC)c(OC)c1]

¹H NMR (400 MHz, CDCl₃) δ 6.51 (s, 2H), 6.01 (brs, 1H), 3.84 (s, 6H), 3.81 (s, 3H), 3.54-3.45 (m, 9H), 3.43-3.32 (m, 3H), 3.10 (t, J=7.5 Hz, 1H), 2.17-2.06 (m, 1H), 1.85-1.70 (m, 3H), 1.61-1.54 (m, 2H), 1.47-1.39 (m, 2H), 1.37-1.30 (m, 2H), 0.87 (t, J=7.3 Hz, 3H). ¹³C NMR (100 MHz, CDCl₃) δ 173.3, 153.2, 136.8, 135.8, 104.7, 71.1, 70.2, 69.9, 69.8, 60.7, 56.0, 55.3, 44.9, 39.2, 32.4, 29.3, 26.6, 26.5, 25.3, 12.3. HRMS (ES+) calculated for C₂₃H₃₉NO₆Cl [M+H]⁺ 460.2466, found 460.2465. TLC (10% CH₃OH in CH₂Cl₂), R_f 0.62 (UV, CAM).

2-(4-((3r,5r,7r)-Adamantan-1-yl)phenoxy)-N-(2-(2-((6-chlorohexyl)oxy)ethoxy)ethyl) acetamide (HyT14, 27): HyT14 was synthesized by the same methods as HyT13 (3).

Scheme 8. Synthesis of HyT14 (27)

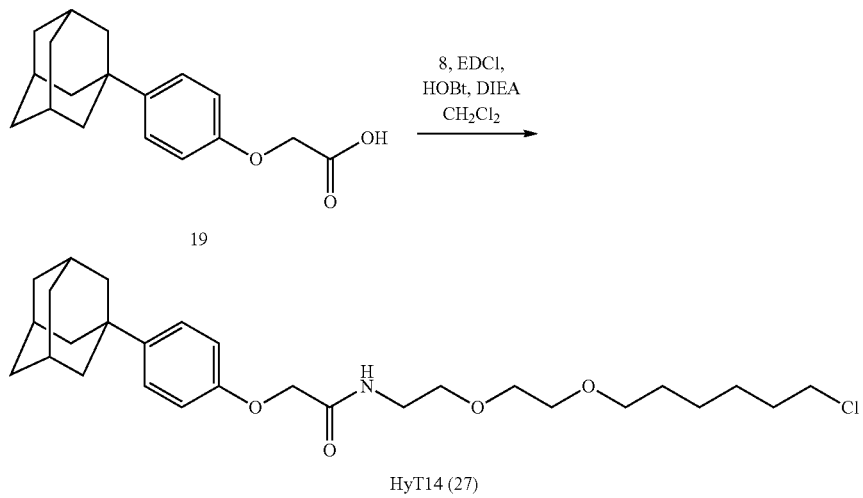

HyT14 (27)

To a solution of (4-adamantan-1-yl-phenoxy) acetic acid 19 (27 mg, 0.094 mmol) and amine 8 (21 mg, 0.094 mmol) in CH₂Cl₂ (1.5 mL) at rt were added HOBt (15 mg, 0.113 mmol) and DIEA (50 μL, 0.282 mmol). The reaction mixture was cooled to 0° C. and EDCI (22 mg, 0.113 mmol) was added to the mixture. The resulting mixture was stirred at rt for 22 h and quenched at 0° C. with H₂O (4 mL). The mixture was extracted twice with ethyl acetate and the combined extracts were washed with brine, dried over Na₂SO₄, filtered, and concentrated. The residue was chromatographed on silica gel to afford 27 (HyT14, 42 mg, 92%). ¹H NMR (400 MHz, CDCl₃) δ 7.29 (d, J=8.8 Hz, 2H), 7.04 (brs, 1H), 6.86 (d, J=8.8 Hz, 2H), 4.47 (s, 2H), 3.58-3.52 (m, 8H), 3.51 (t, J=6.7 Hz, 2H), 3.44 (d, J=6.7 Hz, 2H), 2.08 (s, 3H), 1.87 (s, 6H), 1.79-1.71 (m, 8H), 1.62-1.55 (m, 2H), 1.46-1.38 (m, 2H), 1.37-1.30 (m, 2H). ¹³C NMR (100 MHz, CDCl₃) δ 168.4, 155.0, 145.1, 126.0, 114.2, 71.2, 70.3, 69.9, 67.4, 45.0, 43.3, 38.7, 36.7, 35.6, 32.4, 29.4, 28.8, 26.6, 25.3. HRMS (ES+) calculated for $C_{28}H_{43}NO_4Cl$ [M+H]$^+$ 492.2881, found 492.2883. TLC (10% $CH_3OH$ in $CH_2Cl_2$), $R_f$ 0.65 (UV, CAM).

(1S)—N-(2-(2-(6-chlorohexyl)oxy)ethoxy)ethyl)-7,7-dimethyl-2-oxobicyclo[2.2.1]heptane-1-carboxamide (HyT15, 28): Hy15 was synthesized by the same methods as HyT13 (3).

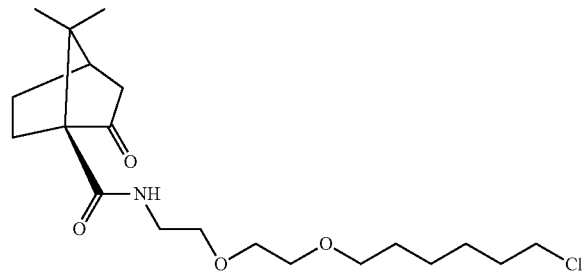 [SMILES: CC1(C)C2CC[C@@]1(C(=O)NCCOCCOCCCCCCCl)C(=O)C2]

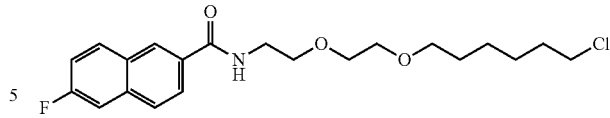

$^1$H NMR (400 MHz, CDCl$_3$) δ 8.31 (s, 1H), 7.91 (dd, J=9.0, 5.6 Hz, 1H), 7.85 (dd, J=8.7, 8.7 Hz, 1H), 7.83 (dd, J=8.5, 8.5 Hz, 1H), 7.47 (dd, J=9.6, 2.4 Hz, 1H), 7.31 (ddd, J=8.7, 8.7, 2.5 Hz, 1H), 3.72-3.70 (m, 4H), 3.69-3.66 (m, 2H), 3.62-3.59 (m, 2H), 3.46 (d, J=6.5 Hz, 2H), 3.44 (d, J=6.5 Hz, 2H), 1.71-1.64 (m, 2H), 1.57-1.50 (m, 2H), 1.39-1.21 (m, 4H). $^{13}$C NMR (100 MHz, CDCl$_3$) δ 167.2, 162.8, 160.3, 135.6, 135.5, 131.4, 131.3, 131.23, 131.21, 129.5, 127.7, 127.6, 127.5, 124.6, 117.3, 117.1, 111.0, 110.8, 71.2, 70.2, 69.9, 69.7, 44.9, 39.7, 32.4, 29.4, 26.5, 25.3. HRMS (ES+) calculated for $C_{21}H_{28}NO_3ClF$ [M+H]$^+$ 396.1742, found 396.1744. TLC (10% $CH_3OH$ in $CH_2Cl_2$), $R_f$ 0.65 (UV, CAM).

2-(4-((3r,5r,7r)-adamantan-1-yl)phenoxy)-N-(24-chloro-11-oxo-3,6,9,15,18-pentaoxa-12-aza tetracosyl)acetamide (HyT18, 30): HyT18 was synthesized by the same methods as HyT9.

Scheme 9. Synthesis of HyT18 (30)

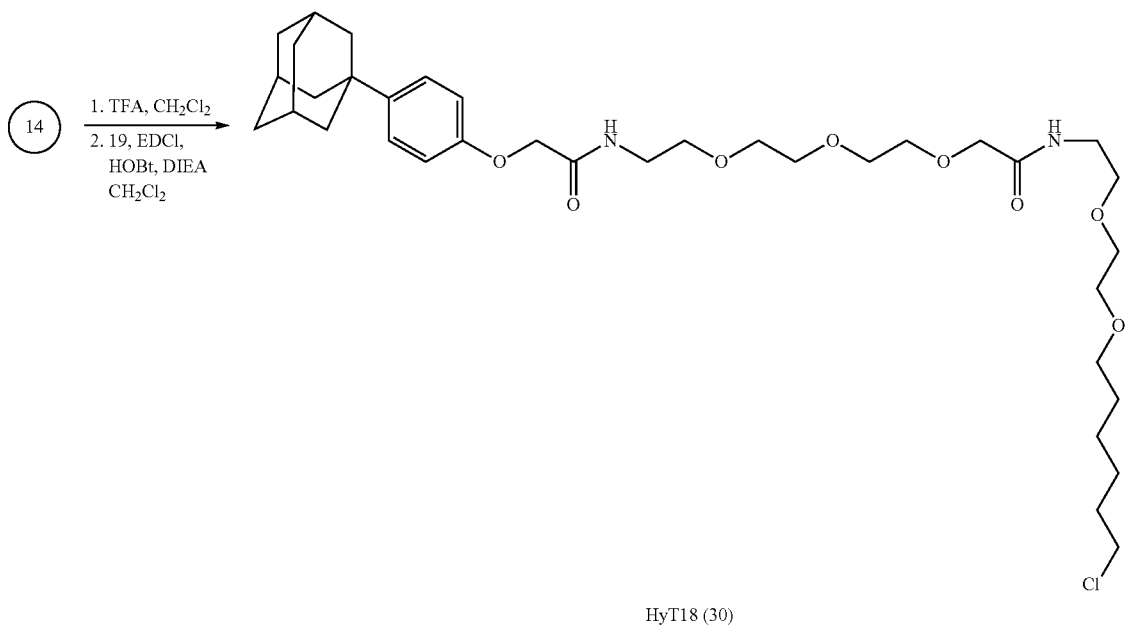

HyT18 (30)

$^1$H NMR (400 MHz, CDCl$_3$) δ 7.79 (s, 1H), 3.62-3.53 (m, 6H), 3.54-3.48 (m, 4H), 3.46 (t, J=6.4 Hz, 2H), 2.53 (dd, J=13.9, 4.0 Hz, 1H), 2.48 (dd, J=5.6, 5.0 Hz, 1H), 2.17-2.09 (m, 1H), 2.07 (t, J=4.5 Hz, 1H), 1.95 (d, J=18.6 Hz, 2H), 1.80-1.73 (m, 2H), 1.62-1.55 (m, 2H), 1.47-1.32 (m, 4H). $^{13}$C NMR (100 MHz, CDCl$_3$) δ 216.9, 169.1, 71.2, 70.4, 70.0, 69.8, 64.6, 50.1, 45.0, 43.7, 43.2, 38.6, 32.5, 29.4, 28.1, 27.6, 26.7, 25.4, 20.9, 20.4. HRMS (ES+) calculated for $C_{20}H_{35}NO_4Cl$ [M+H]$^+$ 388.2255, found 388.2253. TLC (10% $CH_3OH$ in $CH_2Cl_2$), $R_f$ 0.57 (UV, CAM).

N-(2-(2-((6-chlorohexyl)oxy)ethoxy)ethyl)-6-fluoro-2-naphthamide (HyT17, 29): HyT17 was synthesized by the same methods as HyT13 (3).

$^1$H NMR (400 MHz, CD$_3$OD) δ 7.29 (d, J=8.8 Hz, 2H), 6.90 (d, J=8.8 Hz, 2H), 4.47 (s, 2H), 3.95 (s, 2H), 3.64 (s, 4H), 3.60-3.51 (m, 14H), 3.47-3.39 (m, 6H), 2.06 (s, 3H), 1.89 (d, J=2.2 Hz, 6H), 1.80-1.70 (m, 8H), 1.59-1.52 (m, 2H), 1.48-1.42 (m, 2H), 1.41-1.34 (m, 2H). $^{13}$C NMR (100 MHz, CD$_3$OD) δ 172.8, 171.4, 156.9, 146.1, 127.0, 115.4, 72.2, 71.9, 71.5, 71.4, 71.3, 71.2, 71.1, 70.5, 70.4, 68.4, 45.7, 44.5, 39.9, 39.8, 37.8, 36.7, 33.7, 30.5, 30.4, 27.7, 26.5. HRMS (ES+) calculated for $C_{36}H_{58}N_2O_8Cl$ [M+H]$^+$ 681.3871, found 681.3861. TLC (10% $CH_3OH$ in $CH_2Cl_2$), $R_f$ 0.62 (UV, CAM).

N-(2-(2-((6-chlorohexyl)oxy)ethoxy)ethyl)-2-(((2S,5R)-2-isopropyl-5-methylcyclohexyl)oxy)acetamide (HyT23, 31): HyT23 was synthesized by the same methods as 3.

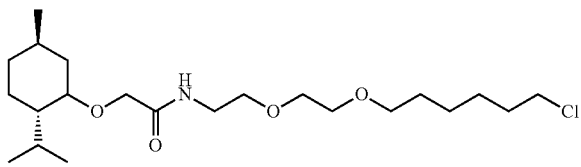 [SMILES: CC(C)[C@@H]1CC[C@@H](C)CC1OCC(=O)NCCOCCOCCCCCCCl]

¹H NMR (400 MHz, CDCl₃) δ 6.97 (brs, 1H), 4.05 (d, J=15.1 Hz, 1H), 3.84 (d, J=15.1 Hz, 1H), 3.61-3.59 (m, 2H), 3.57-3.54 (m, 4H), 3.52 (t, J=6.7 Hz, 2H), 3.49 (t, J=5.0 Hz, 2H), 3.45 (t, J=6.6 Hz, 2H), 3.13 (td, J=10.6, 4.1 Hz, 1H), 2.12 (dtd, J=14.0, 7.0, 2.8 Hz, 1H), 2.06-2.00 (m, 1H), 1.80-1.73 (m, 2H), 1.67-1.63 (m, 2H), 1.62-1.55 (m, 2H), 1.48-1.23 (m, 7H), 0.96 (qd, J=13.8, 3.2 Hz, 1H), 0.91 (d, J=1.2 Hz, 3H), 0.90 (d, J=1.8 Hz, 3H), 0.89-0.81 (m, 2H), 0.77 (d, J=6.9 Hz, 3H). ¹³C NMR (100 MHz, CDCl₃) δ 170.4, 80.5, 71.2, 70.3, 70.0, 69.8, 67.9, 47.9, 45.0, 40.1, 38.4, 34.3, 32.5, 31.3, 29.4, 26.6, 25.9, 25.4, 23.2, 22.2, 20.9, 16.2. HRMS (ES+) calculated for $C_{22}H_{43}NO_4Cl$ [M+H]⁺ 420.2881, found 420.2881. TLC (33% EtOAc in Hexanes), $R_f$ 0.14 (CAM).

(R)—N-(2-(2-((6-chlorohexyl)oxy)ethoxy)ethyl)-2-(2-fluoro-[1,1'-biphenyl]-4-yl) propanamide (HyT24, 32): HyT24 was synthesized by the same methods as HyT13 (3).

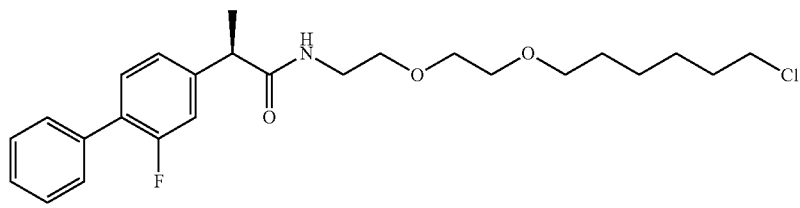 [SMILES: C[C@@H](C(=O)NCCOCCOCCCCCCCl)c1ccc(-c2ccccc2)c(F)c1]

¹H NMR (400 MHz, CDCl₃) δ 7.53-7.51 (m, 2H), 7.45-7.33 (m, 4H), 7.17-7.11 (m, 2H), 6.04 (brs, 1H), 3.59-3.48 (m, 9H), 3.46-3.39 (m, 4H), 1.78-1.71 (m, 2H), 1.60-1.53 (m, 2H), 1.54 (d, J=7.1 Hz, 3H), 1.46-1.39 (m, 2H), 1.37-1.29 (m, 2H). ¹³C NMR (100 MHz, CDCl₃) δ 173.4, 160.9, 158.4, 142.9, 142.8, 135.4, 130.9, 130.8, 128.9, 128.8, 128.4, 127.7, 127.6, 71.2, 70.2, 69.9, 69.6, 46.5, 44.9, 39.3, 32.4, 29.4, 26.6, 25.3, 18.5. HRMS (ES+) calculated for $C_{25}H_{34}NO_3ClF$ [M+H]⁺ 450.2211, found 450.2209. TLC (10% CH₃OH in CH₂Cl₂), $R_f$ 0.66 (UV, CAM).

2-(2,2,4,7-tetramethyl-3,4-dihydroquinolin-1(2H)-yl) ethyl(2-(2-((6-chlorohexyl)oxy) ethoxy)ethyl)carbamate (HyT25, 33): HyT25 was synthesized by the similar methods as 3.

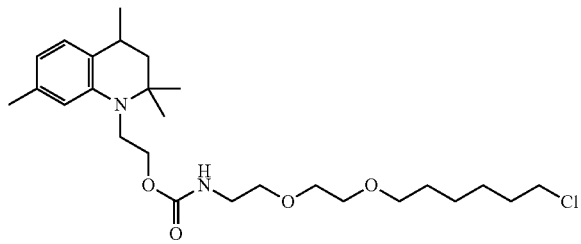 [SMILES: Cc1ccc2c(c1)N(CCOC(=O)NCCOCCOCCCCCCCl)C(C)(C)CC2C]

¹H NMR (400 MHz, CD₃OD) δ 6.97 (d, J=7.7 Hz, 1H), 6.51 (s, 1H), 6.42 (d, J=7.7 Hz, 1H), 4.13 (dd, J=8.7, 5.8 Hz, 1H), 4.06 (dd, J=8.7, 5.7 Hz, 1H), 3.64-3.56 (m, 4H), 3.55-3.50 (m, 4H), 3.47 (t, J=6.5 Hz, 2H), 3.30-3.26 (m, 4H), 2.87-2.78 (m, 1H), 2.23 (s, 3H), 1.77-1.70 (m, 3H), 1.62-1.55 (m, 2H), 1.48-1.35 (m, 5H), 1.29 (s, 3H), 1.26 (d, J=6.7 Hz, 3H), 1.13 (s, 3H). ¹³C NMR (125 MHz, CD₃OD) δ 159.0, 145.8, 137.3, 126.9, 126.5, 118.1, 113.4, 72.2, 71.3, 71.2, 70.9, 63.8, 55.2, 45.6, 44.9, 41.7, 33.7, 30.5, 30.0, 28.3, 27.7, 26.5, 24.4, 21.8, 20.8. HRMS (ES+) calculated for $C_{26}H_{44}N_2O_4Cl$ [M+H]⁺ 483.2990, found 483.2986. TLC (10% CH₃OH in CH₂Cl₂), $R_f$ 0.43 (UV, CAM).

2-(10H-phenoxazin-10-yl)ethyl (2-(2-((6-chlorohexyl)oxy)ethoxy)ethyl)carbamate (HyT26, 34): HyT26 was synthesized by the similar methods as HyT13 (3).

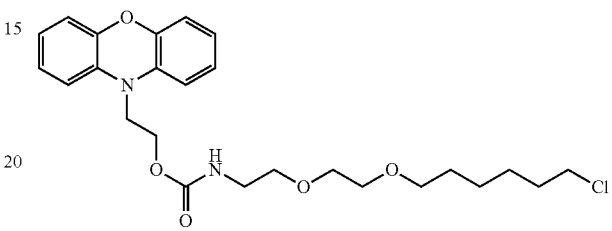

¹H NMR (500 MHz, CD₃OD) δ 6.79 (dd, J=8.2, 1.5 Hz, 1H), 6.78 (dd, J=8.2, 1.5 Hz, 1H), 6.72 (d, J=7.5 Hz, 2H), 6.64 (dd, J=7.5, 1.3 Hz, 1H), 6.62 (dd, J=7.4, 1.3 Hz, 1H), 6.57 (dd, J=7.8, 1.3 Hz, 2H), 4.25 (t, J=6.4 Hz, 2H), 3.81 (t, J=6.4 Hz, 2H), 3.56-3.53 (m, 3H), 3.51 (t, J=6.6 Hz, 3H), 3.48 (t, J=5.5 Hz, 2H), 3.44 (t, J=6.5 Hz, 2H), 3.26 (t, J=5.5 Hz, 2H), 1.76-1.70 (m, 2H), 1.59-1.53 (m, 2H), 1.46-1.40 (m, 2H), 1.39-1.32 (m, 2H). ¹³C NMR (125 MHz, CD₃OD) δ 159.1, 146.5, 134.8, 125.3, 122.6, 116.7, 113.5, 72.6, 71.7, 71.6, 71.3, 61.6, 46.1, 44.7, 42.2, 34.1, 30.9, 28.2, 26.9. HRMS (ES+) calculated for $C_{25}H_{34}N_2O_5Cl$ [M+H]⁺ 477.2156, found 477.2152. TLC (10% CH₃OH in CH₂Cl₂), $R_f$ 0.43 (UV, CAM).

(R)—N-(2-(2-((6-chlorohexyl)oxy)ethoxy)ethyl)-3,3,3-trifluoro-2-methoxy-2-phenyl propanamide (HyT27, 35): HyT27 was synthesized by the same methods as HyT13 (3).

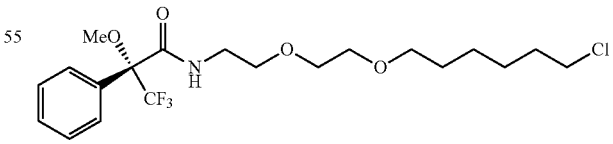

¹H NMR (400 MHz, CDCl₃) δ 7.55-7.53 (m, 2H), 7.40-7.38 (m, 3H), 7.17 (brs, 1H), 3.59-3.56 (m, 5H), 3.54-3.48 (m, 5H), 3.43 (t, J=6.7 Hz, 2H), 3.41 (s, 3H), 1.79-1.72 (m, 2H), 1.61-1.54 (m, 2H), 1.48-1.40 (m, 2H), 1.39-1.31 (m, 2H). ¹³C NMR (100 MHz, CDCl₃) δ 166.3, 132.6, 129.4, 128.4, 127.6, 71.2, 70.2, 69.9, 69.4, 54.9, 45.0, 39.1, 32.4, 29.4, 26.6, 25.3. HRMS (ES+) calculated for $C_{20}H_{30}NO_4ClF_3$ [M+H]$^+$ 440.1815, found 440.1814. TLC (33% EtOAc in Hexanes), $R_f$ 0.51 (UV, CAM).

(R)-1-(2-(2-((6-chlorohexyl)oxy)ethoxy)ethyl)-3-(3-methyl-1,1-diphenylbutan-2-yl)urea (HyT29, 36): HyT29 was synthesized by the same methods as HyT13 (3).

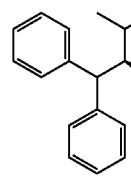

$^1$H NMR (400 MHz, CDCl$_3$) δ 7.38 (dd, J=6.7, 6.7 Hz, 4H), 7.32-7.25 (m, 4H), 7.22-7.14 (m, 2H), 4.72 (t, J=9.7 Hz, 1H), 4.60 (t, J=5.7 Hz, 1H), 4.23 (d, J=9.8 Hz, 1H), 3.95 (d, J=11.0 Hz, 1H), 3.57 (t, J=6.6 Hz, 2H), 3.55-3.42 (m, 7H), 3.37-3.32 (m, 1H), 3.30-3.15 (m, 2H), 1.85-1.78 (m, 2H), 1.76-1.68 (m, 1H), 1.67-1.60 (m, 2H), 1.54-1.46 (m, 2H), 1.44-1.36 (m, 2H), 0.98 (d, J=6.8 Hz, 3H), 0.88 (d, J=6.8 Hz, 3H), 0.04 (s, 6H). $^{13}$C NMR (100 MHz, CDCl$_3$) δ 158.3, 143.1, 142.8, 128.7, 128.4, 128.3, 127.9, 126.4, 126.3, 71.2, 70.9, 70.3, 70.0, 55.7, 45.0, 40.5, 32.5, 29.4, 29.2, 26.6, 25.4, 20.8, 15.1, 0.0. HRMS (ES+) calculated for $C_{28}H_{42}N_2O_3Cl$ [M+H]$^+$ 489.2884, found 489.2881. TLC (10% CH$_3$OH in CH$_2$Cl$_2$), $R_f$ 0.62 (UV, CAM).

2-(bis((R)-1-phenylethyl)amino)-N-(2-(2-((6-chlorohexyl)oxy)ethoxy)ethyl)acetamide (HyT30, 37): HyT30 was synthesized by the same methods as HyT13 (3).

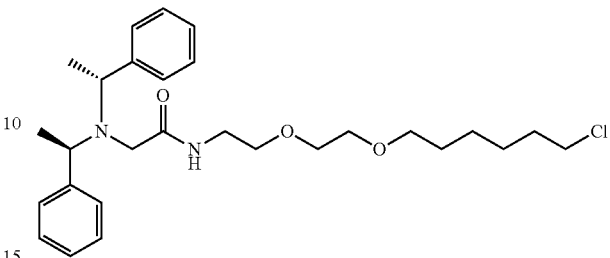

$^1$H NMR (500 MHz, CD$_3$OD) δ 7.34 (s, 4H), 7.33 (s, 4H), 7.27-7.23 (m, 2H), 4.87 (s, 2H), 3.95 (q, J=6.8 Hz, 2H), 3.67-3.60 (m, 4H), 3.52-3.42 (m, 6H), 3.38 (d, J=17.6 Hz, 1H), 3.27-3.16 (m, 2H), 2.85 (d, J=17.6 Hz, 1H), 1.73-1.68 (m, 2H), 1.60-1.54 (m, 2H), 1.45-1.34 (m, 4H), 1.35 (d, J=6.8 Hz, 6H). $^{13}$C NMR (100 MHz, CDCl$_3$) δ 170.0, 142.7, 128.4, 127.7, 127.2, 71.3, 70.4, 70.0, 69.8, 59.5, 50.3, 45.0, 38.4, 32.4, 29.4, 26.5, 25.4, 20.0, −0.03. HRMS (ES+) calculated for $C_{28}H_{42}N_2O_3Cl$ [M+H]$^+$ 489.2884, found 489.2883. TLC (10% CH$_3$OH in CH$_2$Cl$_2$), $R_f$ 0.56 (UV, CAM).

Scheme 10. Synthesis of HyT31 (42)

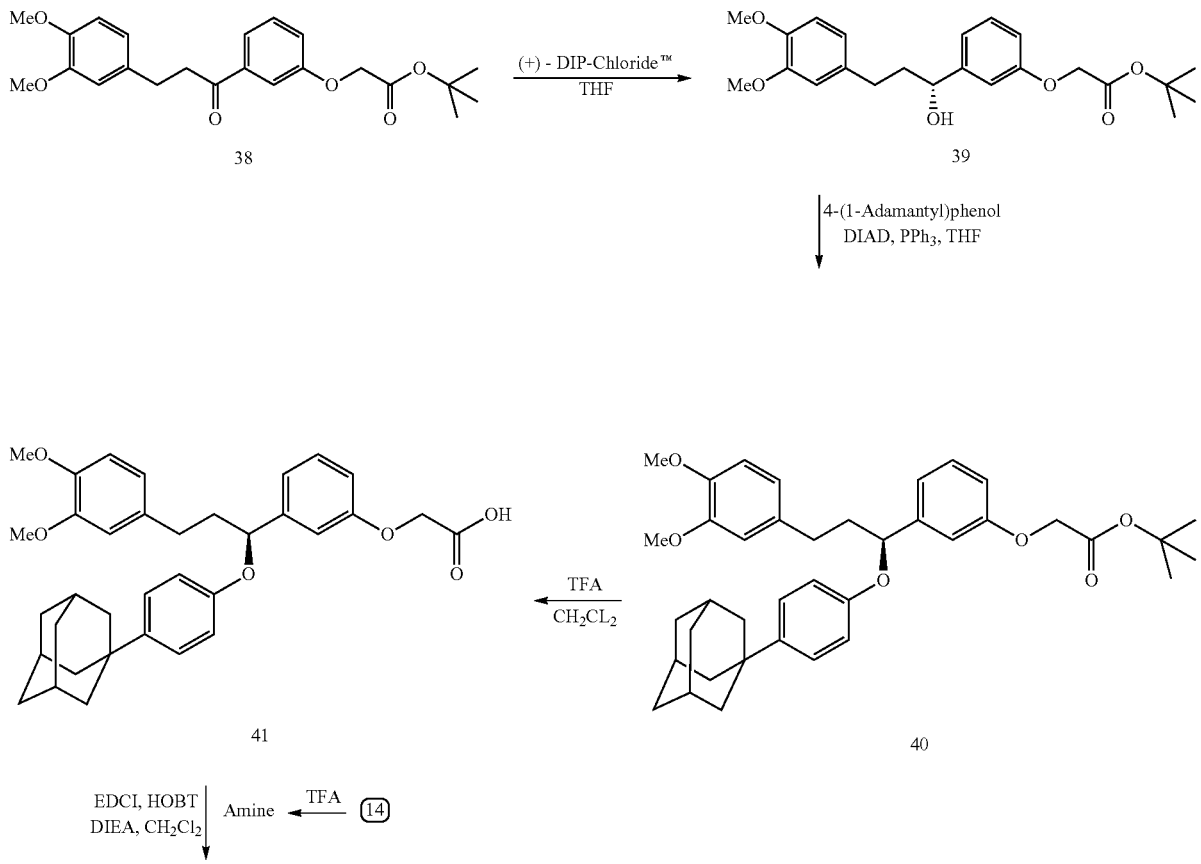

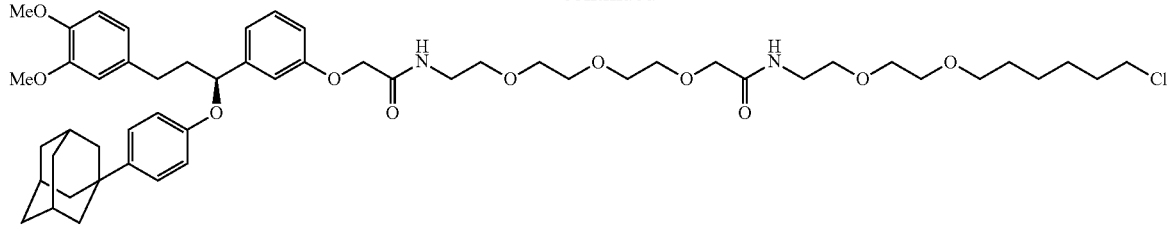

HyT31 (42)

Ketone 38 and Alcohol 39 were prepared by the reported procedure (*Bioorg. Med. Chem.,* 1998, 6, 1309-1335).

Ketone 38: $^1$H NMR (500 MHz, CDCl$_3$) δ 7.55 (d, J=7.9 Hz, 1H), 7.44 (dd, J=2.6, 1.4 Hz, 1H), 7.35 (t, J=7.9 Hz, 1H), 7.10 (ddd, J=8.2, 2.7, 0.8 Hz, 1H), 6.79-6.74 (m, 3H), 4.54 (s, 2H), 3.85 (s, 3H), 3.83 (s, 3H), 3.23 (t, J=8.0 Hz, 2H), 2.98 (t, J=6.9 Hz, 2H), 1.47 (s, 9H). $^{13}$C NMR (125 MHz, CDCl$_3$) δ 198.8, 167.6, 158.1, 148.9, 147.4, 138.2, 133.8, 129.7, 121.4, 120.1, 120.0, 113.1, 111.8, 111.3, 82.6, 77.6, 65.6, 55.9, 55.8, 40.7, 29.8, 28.0.

Alcohol 39: $^1$H NMR (500 MHz, CDCl$_3$) δ 7.26 (dd, J=8.2, 8.2 Hz, 1H), 6.96 (d, J=7.7 Hz, 1H), 6.93 (s, 1H), 6.81-6.78 (m, 2H), 6.74-6.71 (m, 2H), 4.68-4.65 (m, 1H), 4.52 (s, 2H), 3.86 (s, 3H), 3.85 (s, 3H), 2.72-2.66 (m, 1H), 2.64-2.58 (m, 1H), 2.12-2.04 (m, 1H), 2.02-1.95 (m, 1H), 1.83 (d, J=3.3 Hz, 1H), 1.55 (s, 1H), 1.48 (s, 9H). $^{13}$C NMR (100 MHz, CDCl$_3$) δ 168.0, 158.1, 148.8, 147.2, 146.4, 134.3, 129.6, 120.2, 119.1, 113.6, 112.2, 111.7, 111.2, 82.4, 77.2, 73.7, 65.6, 55.9, 55.8, 40.6, 31.6, 28.0. TLC (33% EtOAc in Hexanes), R$_f$ 0.19 (UV, CAM).

tert-Butyl 2-(3-((S)-1-(4-((3S,5S,7S)-adamantan-1-yl) phenoxy)-3-(3,4-dimethoxyphenyl)propyl)phenoxy)acetate 40: To a solution of alcohol 39 (48 mg, 0.1193 mmol), 4-(1-adamantyl)phenol (27 mg, 0.1193 mmol), and triphenylphosphine (35 mg, 0.1312 mmol) in THF (1.2 mL) at rt was added DIAD (26 µL, 0.1312 mmol). The resulting mixture was stirred at rt for 20 h, and diluted at rt with H$_2$O/EtOAc (1:1, 5 mL). The mixture was extracted twice with ethyl acetate and the combined extracts were washed with brine, dried over Na$_2$SO$_4$, filtered, and concentrated. The residue was chromatographed on silica gel to provide tert-Butyl 2-(3-((S)-1-(4-((3S,5S,7S)-adamantan-1-yl)phenoxy)-3-(3,4-dimethoxyphenyl) propyl) phenoxy)acetate 40 (55 mg, 76%). $^1$H NMR (400 MHz, CDCl$_3$) δ 7.23 (dd, J=7.9, 7.9 Hz, 1H), 7.15 (d, J=8.8 Hz, 2H), 6.95 (d, J=7.7 Hz, 1H), 6.88 (s, 1H), 6.80-6.75 (m, 4H), 6.72 (ddd, J=8.2, 8.2, 1.8 Hz, 1H), 6.62 (d, J=1.6 Hz, 1H), 4.94 (dd, J=8.9, 4.0 Hz, 1H), 4.48 (s, 2H), 3.85 (s, 3H), 3.65 (s, 3H), 2.80-2.72 (m, 2H), 2.29-2.20 (m, 1H), 2.05-1.96 (m, 4H), 1.82-1.69 (m, 11H), 1.45 (s, 9H). $^{13}$C NMR (100 MHz, CDCl$_3$) δ 167.9, 158.1, 156.0, 148.5, 147.0, 144.3, 143.6, 133.9, 129.6, 125.6, 120.1, 119.0, 115.1, 113.2, 112.0, 111.9, 111.1, 82.3, 78.5, 77.2, 65.5, 55.8, 55.4, 43.2, 40.6, 36.7, 35.4, 31.5, 28.9, 27.9. LRMS (ES+) [M+Na]$^+$635.8, TLC (25% EtOAc in Hexanes), R$_f$ 0.57 (UV, CAM).

2-(3-((S)-1-(4-((3S,5S,7S)-adamantan-1-yl)phenoxy)-3-(3,4-dimethoxyphenyl)propyl)phenoxy) acetic acid 41: To a stirred solution of tert-Butyl 2-(3-((S)-1-(4-((3S,5S,7S)-adamantan-1-yl)phenoxy)-3-(3,4-dimethoxyphenyl) propyl) phenoxy)acetate 40 (40 mg, 0.0653 mmol) in CH$_2$Cl$_2$ (2.0 mL) at 0° C. was added TFA (0.15 mL). The reaction mixture was stirred at 0° C. for 2.0 h and concentrated. The residue was chromatographed on silica gel to provide acid 41 (31 mg, 85%). $^1$H NMR (400 MHz, CD$_3$OD) δ 7.22 (dd, J=7.9, 7.9 Hz, 1H), 7.13 (d, J=8.8 Hz, 2H), 6.93-6.88 (m, 2H), 6.84 (d, J=8.1 Hz, 1H), 6.78 (dd, J=8.2, 2.2 Hz, 1H), 6.74 (d, J=8.8 Hz, 2H), 6.71 (dd, J=8.2, 1.7 Hz, 1H), 6.67 (d, J=1.7 Hz, 1H), 4.97 (dd, J=8.8, 4.2 Hz, 1H), 4.59 (s, 2H), 3.78 (s, 3H), 3.56 (s, 3H), 2.74 (t, J=7.6 Hz, 2H), 2.22-2.15 (m, 1H), 2.03-1.96 (m, 4H), 1.84-1.79 (m, 6H), 1.78-1.71 (m, 6H). $^{13}$C NMR (100 MHz, CD$_3$OD) δ 159.7, 157.4, 150.2, 148.6, 145.7, 144.9, 135.6, 130.7, 126.6, 121.7, 120.2, 116.4, 114.3, 113.7, 113.5, 113.2, 79.4, 56.5, 56.1, 44.5, 41.8, 37.8, 36.6, 32.5, 30.5. TLC (10% CH$_3$OH in CH$_2$Cl$_2$), R$_f$ 0.24 (UV, CAM).

2-(3-((S)-1-(4-((3S,5S,7S)-adamantan-1-yl)phenoxy)-3-(3,4-dimethoxyphenyl)propyl)phenoxy)-N-(24-chloro-11-oxo-3,6,9,15,18-pentaoxa-12-azatetracosyl)acetamide (HyT31, 42): 42 synthesized by the similar methods as 3. $^1$H NMR (500 MHz, CD$_3$OD) δ 7.25 (dd, J=7.1, 7.1 Hz, 1H), 7.15 (d, J=8.7 Hz, 2H), 6.96 (d, J=6.8 Hz, 2H), 6.84 (d, J=8.2 Hz, 2H), 6.75 (d, J=8.8 Hz, 2H), 6.71 (d, J=8.2 Hz, 1H), 6.67 (d, J=1.4 Hz, 1H), 5.00 (dd, J=8.9, 4.0 Hz, 1H), 4.47 (d, J=3.2 Hz, 2H), 3.92 (s, 2H), 3.77 (s, 3H), 3.59 (s, 3H), 3.56-3.50 (m, 18H), 3.43-3.36 (m, 6H), 2.76 (t, J=7.0 Hz, 2H), 2.25-2.17 (m, 1H), 2.02-1.97 (m, 4H), 1.84-1.69 (m, 14H), 1.56-1.51 (m, 2H), 1.45-1.39 (m, 2H), 1.37-1.32 (m, 2H). $^{13}$C NMR (125 MHz, CD$_3$OD) δ 172.7, 171.1, 159.5, 157.4, 150.4, 148.8, 145.9, 145.0, 135.8, 130.9, 126.7, 121.8, 120.7, 116.5, 114.8, 113.7, 113.5, 79.5, 72.2, 72.0, 71.4, 71.33, 71.31, 71.2, 71.1, 70.5, 70.4, 68.4, 56.7, 56.3, 45.7, 44.6, 41.8, 40.0, 39.8, 37.9, 36.6, 33.7, 32.5, 30.6, 30.5, 27.7, 26.5. HRMS (ES+) calculated for C$_{53}$H$_{76}$N$_2$O$_{11}$Cl [M+H]$^+$ 951.5138, found 951.5142. TLC (10% CH$_3$OH in CH$_2$Cl$_2$), R$_f$ 0.68 (UV, CAM).

N-(2-(2-((6-chlorohexyl)oxy)ethoxy)ethyl)-4-pentylbicyclo[2.2.2]octane-1-carboxamide (HyT33, 43): HyT33 was synthesized by the same methods as HyT13 (3).

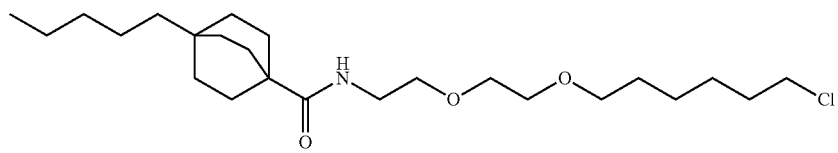 [SMILES: CCCCCC12CCC(C(=O)NCCOCCOCCCCCCCl)(CC1)CC2]

$^1$H NMR (400 MHz, CDCl$_3$) δ 6.01 (t, J=4.8 Hz, 1H), 3.60-3.58 (m, 2H), 3.56-3.54 (m, 2H), 3.52 (t, J=6.5 Hz, 4H), 3.45 (t, J=6.7 Hz, 2H), 3.19 (t, J=5.3 Hz, 2H), 1.80-1.73 (m, 2H), 1.72-1.68 (m, 6H), 1.63-1.56 (m, 2H), 1.49-1.41 (m, 2H), 1.40-1.34 (m, 8H), 1.30-1.23 (m, 2H), 1.20-1.12 (m, 4H), 1.09-1.03 (m, 2H), 0.86 (t, J=7.0 Hz, 3H). $^{13}$C NMR (100 MHz, CDCl$_3$) δ 178.2, 77.2, 71.2, 70.2, 69.9, 69.8, 45.0, 41.2, 39.0, 38.9, 32.7, 32.5, 30.6, 30.3, 29.4, 28.8, 26.6, 25.4, 23.3, 22.6, 14.0. HRMS (ES+) calculated for C$_{24}$H$_{45}$NO$_3$Cl [M+H]$^+$ 430.3088, found 430.3088. TLC (5% CH$_3$OH in CH$_2$Cl$_2$), R$_f$ 0.51 (CAM).

Scheme 11. Synthesis of HyT34 (44)

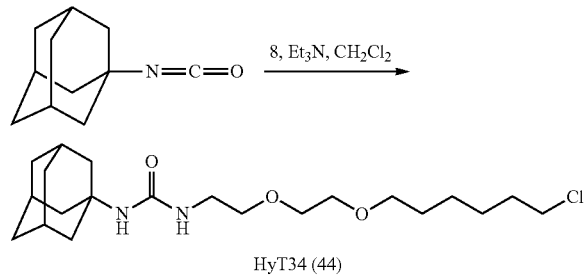

To a solution of amine 8 (23 mg, 0.1 mmol) in CH$_2$Cl$_2$ (1.5 mL) at rt were triethylamine (140 μL, 1.0 mmol) and 1-adamantyl isocyanate (18 mg, 0.1 mmol). The reaction mixture was stirred at rt for 16 h, and evaporated. The residue was chromatographed on silica gel to give 1-((3s,5s,7s)-adamantan-1-yl)-3-(2-(2-((6-chlorohexyl)oxy)ethoxy)ethyl)urea 44 (HyT34, 40 mg, 76%). $^1$H NMR (400 MHz, CDCl$_3$) δ 4.81 (t, J=5.6 Hz, 1H), 4.46 (s, 1H), 3.60-3.58 (m, 2H), 3.56-3.54 (m, 2H), 3.53 (t, J=6.7 Hz, 2H), 3.52 (t, J=6.7 Hz, 2H), 3.44 (t, J=6.7 Hz, 2H), 3.31 (t, J=5.4 Hz, 1H), 3.30 (t, J=5.4 Hz, 1H), 2.04 (brs, 3H), 1.93 (t, J=2.8 Hz, 6H), 1.79-1.72 (m, 2H), 1.64 (t, J=2.8 Hz, 6H), 1.62-1.56 (m, 2H), 1.48-1.40 (m, 2H), 1.39-1.31 (m, 2H). $^{13}$C NMR (100 MHz, CDCl$_3$) δ 157.4, 77.2, 71.2, 70.9, 70.2, 70.0, 50.7, 45.0, 42.4, 39.9, 36.4, 32.4, 29.5, 29.4, 26.6, 25.3. HRMS (ES+) calculated for C$_{21}$H$_{38}$N$_2$O$_3$Cl [M+H]$^+$ 401.2571, found 401.2573. TLC (10% CH$_3$OH in CH$_2$Cl$_2$), R$_f$ 0.59 (CAM).

1-((3s,5s,7s)-Adamantan-1-yl)-3-(2-(2-((6-chlorohexyl)oxy)ethoxy)ethyl)thiourea (HyT35, 45): HyT35 was synthesized by the same methods as HyT34 (44).

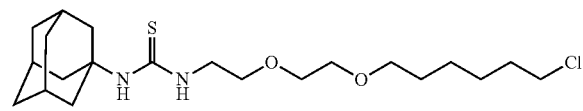 [SMILES: S=C(NCCOCCOCCCCCCCl)NC12CC3CC(CC(C3)C1)C2]

$^1$H NMR (500 MHz, CDCl$_3$) δ 6.20 (s, 1H), 3.76 (s, 2H), 3.63-3.60 (m, 3H), 3.55-3.49 (m, 5H), 3.45-3.38 (m, 2H), 2.14-1.93 (m, 9H), 1.77-1.72 (m, 2H), 1.69-1.63 (m, 6H), 1.59-1.54 (m, 2H), 1.48-1.39 (m, 2H), 1.38-1.30 (m, 2H). $^{13}$C NMR (125 MHz, CDCl$_3$) δ 180.8, 77.2, 71.3, 70.4, 70.1, 53.8, 45.0, 42.4, 42.1, 42.0, 36.2, 32.5, 29.7, 29.6, 29.5, 26.8, 25.4. HRMS (ES+) calculated for C$_{11}$H$_{38}$N$_2$O$_2$SCl [M+H]$^+$ 417.2343, found 417.2341. TLC (10% CH$_3$OH in CH$_2$Cl$_2$), R$_f$ 0.58 (CAM).

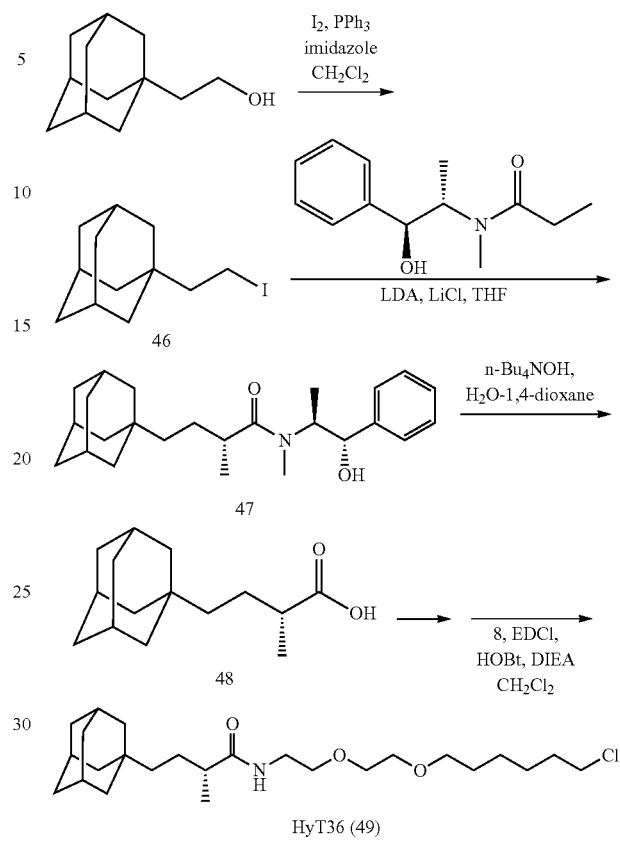

(3r,5r,7r)-1-(2-iodoethyl)adamantine 46: To a stirred solution of PPh$_3$ (1.57 g, 6.0 mmol) in CH$_2$Cl$_2$ (14 mL) at rt were added imidazole (442 mg, 6.5 mmol) and iodine (1.52 g, 6.0 mmol). The reaction mixture was cooled to 0° C. and stirred at 0° C. for 5 min. A solution of 1-adamantane ethanol (901 mg, 5.0 mmol) in CH$_2$Cl$_2$ (6 mL) was added dropwise to the mixture via cannula. The resulting mixture was stirred at 0° C. for 2.0 h and H$_2$O (20 mL) was added to the mixture at ice-bath. The organic layer was separated and the aqueous phase was extracted twice with CH$_2$Cl$_2$. The combined organic layers were concentrated. The concentrate was purified by column chromatography to afford (3r,5r,7r)-1-(2-iodoethyl)adamantine 46 (1.375 g, 95%) as a white solid. $^1$H NMR (400 MHz, CDCl$_3$) δ 3.17 (d, J=17.9 Hz, 1H), 3.17 (dt, J=3.2, 1.8 Hz, 1H), 1.95 (brs, 3H), 1.78 (d, J=17.9 Hz, 1H), 1.78 (dt, J=3.3, 1.8 Hz, 1H), 1.71 (brs, 1H), 1.68 (brs, 2H), 1.63-1.61 (m, 1H), 1.61-1.58 (m, 1H), 1.49 (d, J=2.4 Hz, 1H). TLC (10% EtOAc in Hexanes), R$_f$ 0.81 (UV, CAM).

(R)-4-((3R,5R,7R)-adamantan-1-yl)-N-((1S,2S)-1-hydroxy-1-phenylpropan-2-yl)-N,2-dimethyl butanamide 47: A solution of n-butyllithium (2.5 M in hexanes, 0.8 mL, 2.0 mmol, 4.0 eq.) was added to a suspension of lithium chloride (275 mg, 6.5 mmol, 13.0 eq.) and diisopropylamine (0.3 mL, 2.15 mmol, 4.3 eq.) in THF (2 mL) at −78° C. The resulting suspension was warmed briefly to 0° C., then was cooled to −78° C. An ice-cooled solution of (1S,2S)-(+)-pseudoephedrine propionamide (221 mg, 1.0 mmol, 2.0 eq.) in THF (2 mL) was added dropwise over 30 min via cannula and the reaction mixture was stirred at 78° C. for 1.0 h, at 0° C. for 15 min, and at room temperature for 5 min, and cooled to 0°

C. To this solution at 0° C. was added a solution of iodide 46 (145 mg, 0.5 mmol, 1.0 eq.) in THF (1 mL) via cannula, and the reaction mixture was stirred at 0° C. for 6 h and at room temperature for 20 h. The pale yellow mixture was cooled to 0° C., then treated with half-saturated aqueous NH$_4$Cl solution (10 mL), and extracted with ethyl acetate (10 mL×3). The combined organic layers were dried over Na$_2$SO$_4$, filtered, and concentrated. The residue was purified by flash chromatography on silica gel to afford (R)-4-((3R,5R,7R)-adamantan-1-yl)-N-((1S,2S)-1-hydroxy-1-phenyl-propan-2-yl)-N,2-dimethylbutanamide 47 (178 mg, 93%). $^1$H NMR (400 MHz, CDCl$_3$) δ 7.38-7.30 (m, 5H), 4.62 (dd, J=7.3, 7.3 Hz, 1H), 4.35 (brs, 1H), 2.81 (s, 3H), 2.50-2.41 (m, 1H), 1.93 (s, 3H), 1.71-1.60 (m, 7H), 1.57-1.41 (m, 8H), 1.17 (d, J=7.0 Hz, 3H), 1.08 (d, J=6.7 Hz, 3H), 0.98-0.87 (m, 2H). $^{13}$C NMR (100 MHz, CDCl$_3$) δ 179.3, 142.7, 128.7, 128.3, 127.5, 126.9, 126.3, 77.2, 76.5, 42.3, 42.2, 37.4, 37.2, 32.1, 28.7, 26.9, 17.2, 15.4. TLC (33% EtOAc in Hexanes), R$_f$ 0.24 (UV, CAM).

(R)-4-((3R,5R,7R)-adamantan-1-yl)-2-methylbutanoic acid 48: To a solution of (R)-4-((3R,5R,7R)-adamantan-1-yl)-N-((1S,2S)-1-hydroxy-1-phenylpropan-2-yl)-N,2-dimethylbutanamide 47 (120 mg, 0.313 mmol) in 1,4-dioxane (3 mL) and H$_2$O (2 mL) at rt was added n-Bu$_4$NOH (40% wt % in H$_2$O, 1.22 mL, 1.878 mmol). The reaction mixture was stirred at 110° C. for 20 h, cooled to rt, and evaporated. The residue was diluted with H$_2$O (2 mL), cooled to 0° C., adjusted to pH 4 with 3N—HCl. The mixture was extracted twice with ethyl acetate and the combined extracts were washed with brine, dried over Na$_2$SO$_4$, filtered, and concentrated. The residue was chromatographed on silica gel to afford acid 48 (73 mg, quant.). $^1$H NMR (400 MHz, CDCl$_3$) δ 10.8 (brs, 1H), 2.41-2.32 (m, 1H), 1.93 (brs, 3H), 1.71-1.60 (m, 7H), 1.46 (d, J=2.0 Hz, 6H), 1.42-1.34 (m, 1H), 1.18 (d, J=7.0 Hz, 3H), 1.11-1.03 (m, 2H). $^{13}$C NMR (100 MHz, CDCl$_3$) δ 183.5, 42.3, 41.7, 40.0, 37.2, 32.1, 28.7, 26.5, 16.8. TLC (33% EtOAc in Hexanes), R$_f$ 0.62 (CAM).

(R)-4-((3R,5R,7R)-adamantan-1-yl)-N-(2-(2-((6-chloro-hexyl)oxy)ethoxy)ethyl)-2-methylbutan amide (HyT36, 49): HyT36 was synthesized by the EDC-mediated coupling method as HyT13. $^1$H NMR (400 MHz, CDCl$_3$) δ 5.93 (s, 1H), 3.62-3.59 (m, 2H), 3.57-3.55 (m, 2H), 3.54 (t, J=5.0 Hz, 2H), 3.52 (t, J=6.5 Hz, 2H), 3.47-3.43 (m, 4H), 2.09-2.01 (m, 1H), 1.92 (s, 3H), 1.79 (t, J=6.7 Hz, 1H), 1.75 (t, J=6.7 Hz, 1H), 1.69-1.57 (m, 9H), 1.47-1.27 (m, 11H), 1.12 (d, J=6.8 Hz, 3H), 1.03-0.98 (m, 2H). $^{13}$C NMR (100 MHz, CDCl$_3$) δ 176.6, 71.2, 70.2, 70.0, 44.9, 42.4, 42.2, 42.1, 38.9, 37.2, 32.5, 32.1, 29.4, 28.7, 27.2, 26.6, 25.4, 17.8. HRMS (ES+) calculated for C$_{25}$H$_{45}$NO$_3$Cl [M+H]$^+$ 442.3088, found 442.3086. TLC (5% CH$_3$OH in CH$_2$Cl$_2$), R$_f$ 0.40 (CAM).

HyT39 was synthesized by the same methods as HyT36.

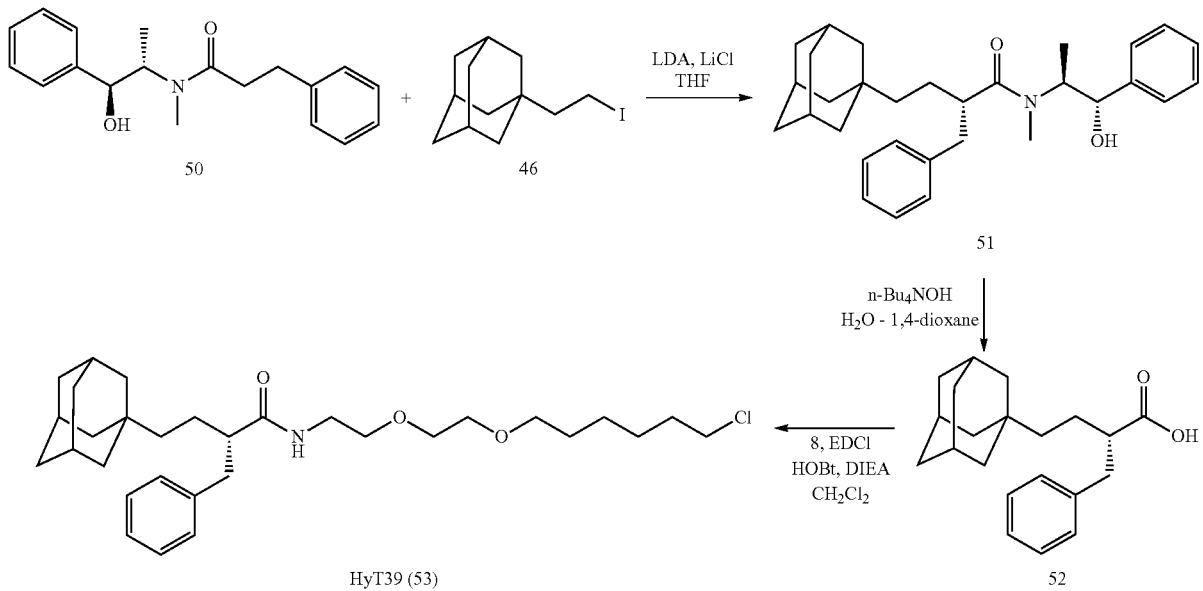

Scheme 13. Synthesis of HyT39 (53)

N-((1S,2S)-1-hydroxy-1-phenylpropan-2-yl)-N-methyl-3-phenylpropanamide 50: To a solution of (1S,2S)-(+)-pseudoephedrine (496 mg, 3.0 mmol) in THF (9 mL) at rt was added triethylamine (0.59 mL, 4.2 mmol). The mixture was cooled to 0° C., and hydrocinnamoyl chloride (0.54 mL, 3.6 mmol) was added to the mixture. The resulting mixture was stirred at 0° C. for 0.5 h, quenched with H$_2$O (10 mL), and extracted twice with ethyl acetate. The combined extracts were washed with brine, dried over Na$_2$SO$_4$, filtered, and concentrated. The residue was chromatographed on silica gel to afford N-((1S,2S)-1-hydroxy-1-phenylpropan-2-yl)-N-methyl-3-phenylpropanamide 50 (865 mg, 97%). $^1$H NMR (500 MHz, CD$_3$OD) δ 7.38-7.31 (m, 4H), 7.29-7.13 (m, 6H), 4.77 (brs, ½H), 4.58 (dd, J=11.2, 8.2 Hz, 1H), 4.03-3.97 (m, ½H), 2.88 (d, J=10.7 Hz, 3H), 2.87 (t, J=8.1 Hz, 2H), 2.76-2.58 (m, 2H), 0.88 (t, J=7.0 Hz, 3H). $^{13}$C NMR (extra peaks are due to amide-bond rotamers, 125 MHz, CD$_3$OD) δ 175.7, 175.6, 143.8, 142.6, 142.5, 130.0, 129.6, 129.5, 129.4, 129.3, 128.8, 128.1, 128.0, 127.13, 127.11, 76.3, 76.1, 59.7, 36.8, 36.2, 32.7, 32.4, 27.9, 15.6, 14.4. TLC (33% EtOAc in Hexanes), R$_f$ 0.08 (UV, CAM).

(S)-4-((3S,5S,7S)-adamantan-1-yl)-2-benzyl-N-((1S,2S)-1-hydroxy-1-phenylpropan-2-yl)-N-methylbutanamide 51: 51 was synthesized by the same method as 47. $^1$H NMR (400 MHz, CDCl$_3$) δ 7.30-7.28 (m, 4H), 7.27-7.24 (m, 4H), 7.20-7.17 (m, 2H), 4.48 (dd, J=6.5, 6.5 Hz, 1H), 2.80-2.71 (m, 2H), 2.49 (s, 3H), 1.94 (s, 3H), 1.72-1.59 (m, 7H), 1.55 (s, 3H), 1.43 (d, J=2.2 Hz, 6H), 0.99 (d, J=7.0 Hz, 3H), 0.97-0.92 (m, 1H), 0.90-0.83 (m, 2H). TLC (33% EtOAc in Hexanes), $R_f$ 0.43 (UV, CAM).

(S)-4-((3S,5S,7S)-adamantan-1-yl)-2-benzylbutanoic acid 52: 52 was synthesized by the same method as 48. $^1$H NMR (400 MHz, CDCl$_3$) δ 10.15 (brs, 1H), 7.28-7.23 (m, 2H), 7.20-7.14 (m, 3H), 2.94 (dd, J=13.8, 8.2 Hz, 1H), 2.76 (dd, J=13.8, 6.5 Hz, 1H), 2.61-2.53 (m, 1H), 1.92 (s, 3H), 1.69-1.56 (m, 7H), 1.54-1.46 (m, 1H), 1.43 (d, J=2.0 Hz, 6H), 1.13-1.03 (m, 2H). $^{13}$C NMR (100 MHz, CDCl$_3$) δ 181.8, 139.2, 128.6, 128.4, 126.3, 47.9, 42.3, 41.6, 37.9, 37.2, 32.1, 28.7, 24.8. TLC (25% EtOAc in Hexanes), $R_f$ 0.54 (UV).

(S)-4-((3S,5S,7S)-adamantan-1-yl)-2-benzyl-N-(2-(2-((6-chlorohexyl)oxy)ethoxy)ethyl)butanamide (HyT39, 53): HyT39 was synthesized by the EDC-mediated coupling method as HyT13. $^1$H NMR (500 MHz, CDCl$_3$) δ 7.25-7.22 (m, 2H), 7.17-7.14 (m, 3H), 5.72 (t, J=5.4 Hz, 1H), 3.52 (t, J=6.6 Hz, 2H), 3.50-3.45 (m, 3H), 3.44-3.40 (m, 1H), 3.42 (t, J=6.6 Hz, 2H), 3.69-3.33 (m, 2H), 3.31-3.25 (m, 1H), 3.23-3.19 (m, 1H), 2.88 (dd, J=13.3, 9.6 Hz, 1H), 2.72 (dd, J=13.4, 5.3 Hz, 1H), 2.16-2.11 (m, 1H), 1.92 (s, 3H), 1.79-1.73 (m, 2H), 1.69-1.56 (m, 9H), 1.47-1.41 (m, 3H), 1.44 (d, J=2.2 Hz, 6H), 1.38-1.33 (m, 2H), 1.09-0.97 (m, 2H). $^{13}$C NMR (125 MHz, CDCl$_3$) δ 174.8, 140.1, 128.9, 128.2, 126.0, 71.2, 70.1, 70.0, 69.9, 51.0, 44.9, 42.3, 42.1, 39.2, 38.8, 37.2, 32.5, 32.1, 29.4, 28.6, 26.6, 25.7, 25.4. HRMS (ES+) calculated for $C_{31}H_{49}NO_3Cl$ [M+H]$^+$ 518.3401, found 518.3405. TLC (5% CH$_3$OH in CH$_2$Cl$_2$), $R_f$ 0.55 (UV, CAM).

2-((3r,5r,7r)-adamantan-1-yl)-N-(24-chloro-11-oxo-3,6,9,15,18-pentaoxa-12-azatetracosyl) acetamide (HyT40, 54): HyT40 was synthesized by the similar methods as 3.

$^1$H NMR (400 MHz, CDCl$_3$) δ 7.18 (s, 1H), 6.19 (s, 1H), 4.04 (s, 2H), 3.70-3.41 (m, 24H), 1.95 (s, 3H), 1.80-1.73 (m, 4H), 1.70-1.55 (m, 8H), 1.61 (d, J=2.2 Hz, 6H), 1.48-1.41 (m, 2H), 1.39-1.33 (m, 2H). $^{13}$C NMR (100 MHz, CDCl$_3$) δ 171.1, 171.0, 71.2, 70.7, 70.6, 70.5, 70.4, 70.2, 70.1, 70.0, 69.9, 69.8, 51.5, 45.0, 42.5, 39.0, 38.6, 36.7, 32.6, 32.5, 29.4, 28.6, 26.6, 25.4. HRMS (ES+) calculated for $C_{30}H_{54}N_2O_7Cl$ [M+H]$^+$ 589.3620, found 589.3622. TLC (10% CH$_3$OH in CH$_2$Cl$_2$), $R_f$ 0.66 (UV, CAM).

Biological Experiments
Methods
Cell Culture and Materials

Indicated cells were grown at 37° C. in DMEM, supplemented with 10% fetal bovine serum and penicillin/streptomycin. The HaloTag protein was obtained from pHT2 vector (Promega). The luciferase sequence was obtained from pGL3-Basic vector (Promega), mouse Ror2 was kindly provided by Sigmar Stricker (Max Planck-Institute for Molecular Genetics), *Danio rerio* Smad5 was cloned from a zebrafish cDNA library and H-RasG12V was obtained from Addgene plasmid 9051, contributed by Robert Weinberg (MIT). The remaining transmembrane proteins were cloned from a human spleen cDNA library (Invitrogen). A D106A point mutation was introduced into the HaloTag gene by the QuikChange Site Directed mutagenesis kit (Stratagene). Flp-In 293 cells were purchased from Invitrogen. HA-HaloTag-Smad5 and EGFP-HaloTag were cloned into the pCS2+ vector, while the rest of the constructs were cloned into a retroviral pEYK3.1 vector (kindly provided by George Daley, MIT) by excising GFP[41]. Retrovirus was generated in GP2-293 cells (Clontech) with a pVSV-G and a corresponding pEYK plasmid, and the indicated cells were infected as described[41]. Anti-HA antibody was purchased from Covance (clone 16B12) and anti-β-actin antibody was purchased from Sigma (clone AC-74). HyT compounds were stored and aliquoted in DMSO as 1000× stock solutions.

Scheme 14. Synthesis of HyT40 (54)

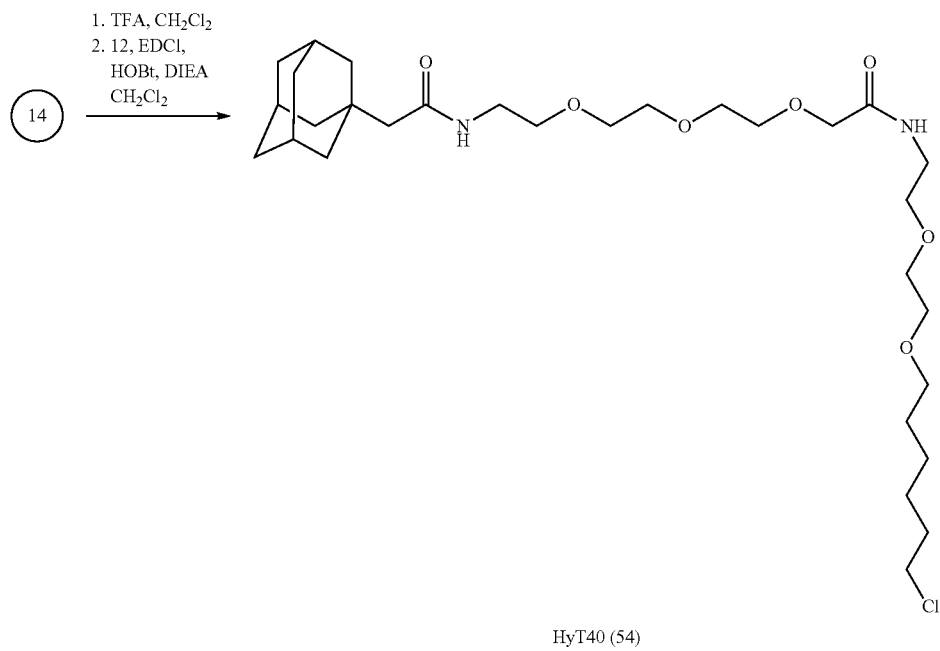

HyT40 (54)

Luciferase Assay

Ten thousand stable HEK 293T cells infected with HA-luciferase-HaloTag were plated into each well in a 96-well plate. The next day, indicated HyT compounds were added in triplicate and the cells were cultured for another 24 hours. The cells were washed once with cold PBS and lysed in Passive Lysis Buffer (Promega). The luciferase activity was performed by Steady-Glo Luciferase Assay System (Promega) on a Wallac Victor 2 Plate Reader (Perkin Elmer) and the luciferase activity was normalized by protein concentration, as determined by the Bradford assay.

Immunoblotting

The indicated cells were washed twice with cold PBS and the cells were lysed in lysis buffer (1×PBS, 1% NP-40, 1 mM EDTA, 40 mM HEPES) with protease inhibitors. The lysates were cleared by centrifugation at 10,000 g for 5 min. The total protein concentration was determined by Bradford assay and 50 µg of protein was loaded onto an 8% Bis-Tris gel. To solubilize polyubiquitinated and aggregated proteins upon proteasome inhibition[42] samples generated for FIG. 12d were lysed with a SDS lysis buffer (1×PBS, 1% NP-40, 1% SDS, 1% sodium deoxycholate, 1 mM EDTA, 40 mM HEPES) with protease inhibitors. The blots were processed by standard procedures with indicated antibodies, and the band intensities were quantified by ImageJ.

Flow Cytometry Analysis

Stable HeLa cells were raised by cotransfection of pCS2/EGFP-HaloTag and p-Puro containing the puromycin resistance gene. A clonal population of cells expressing EGFP-HaloTag was isolated. These cells were treated with vehicle or 1 µM HyT13 for 24 hours, washed with PBS and trypsinized. The cells were resuspended in FBS-free DMEM and the intracellular GFP level was measured by FACSCalibur (BD Biosciences).

Zebrafish Danio rerio Experiments

The wild-type fish line TLF was used for this study. The HA-HaloTag-Smad5 in pCS2+ plasmid was in vitro transcribed with the SP6 transcription kit (Ambion). The mRNA was injected at 100 ng/µL at the one cell stage and embryos were raised to the 256-cell stage, when they were moved to glass depression slides (10-per-well) and put in 1 ml E2 media with or without HyT13 (10 µM). Embryos were cultured at 28.6° C. for 24 hours and then dechorionated and de-yolked as described[43]. Approximately 60 embryos per condition were collected for immunoblot analysis, as described above.

Focus Formation Assay

One hundred thousand NIH-3T3 cells infected with HA-HaloTag-H-RasG12V and HA-HaloTag(D106A)-H-RasG12V were plated onto 10-cm cell culture plates in 10% FBS with DMEM. The next day, the media was replaced with 1% FBS media and the cells were administered either vehicle or 1 µM HyT13. The media and the drug were replaced every two days. On day 6, the foci were photographed and counted as the number of distinct foci per 1-cm$^2$ area.

Tumor Formation Assay

One hundred thousand NIH-3T3 cells expressing HA-HaloTag-H-RasG12V were injected into the flank of anesthetized 6-week old female nu/nu nude mice (Charles River Laboratories). Two hours later, the mice were IP injected with either vehicle (10 µl, volume, with 5 µl, DMSO and 5 µl, of Cremophor EL), 25 mg/kg HyT13 or 100 mg/kg HyT13. The drug injections continued daily until the end of the experiment. Upon the appearance of tumors on day 7, the tumors were measured daily with calipers, and their volumes were calculated using the formula: $a(b)^2/2$, where a and b represent the longest and shortest diameters of the tumor, respectively.

Results

Hydrophobic Tagging Destabilizes HaloTag Fusion Proteins

Figure 5:
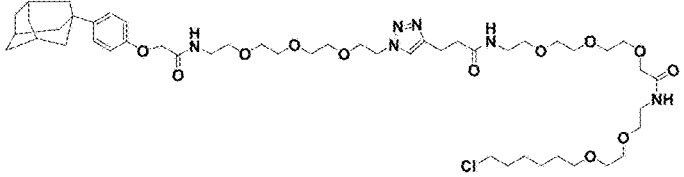
FIG. 5 shows representative compounds which were synthesized and a number which were tested.
Figure 5:
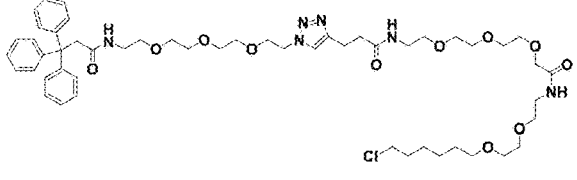
Figure 5:
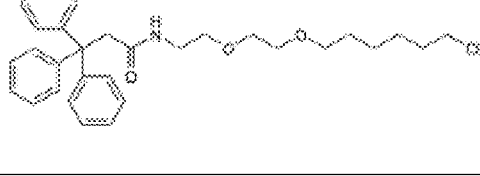
Figure 5:
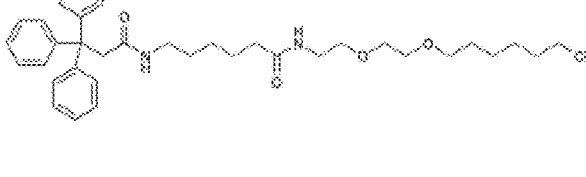
Figure 5:
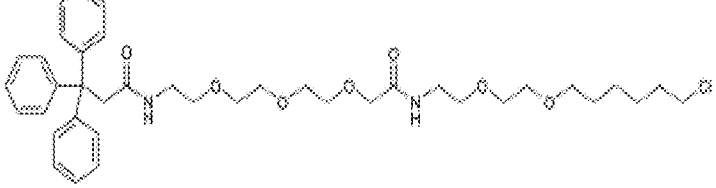
Figure 5:
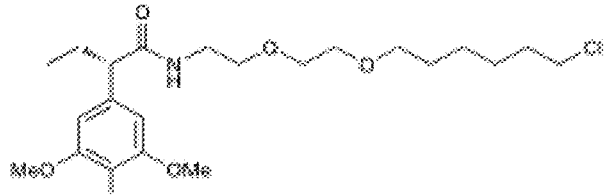
Figure 5:
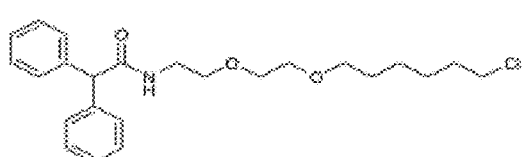
Figure 5:
Figure 5:
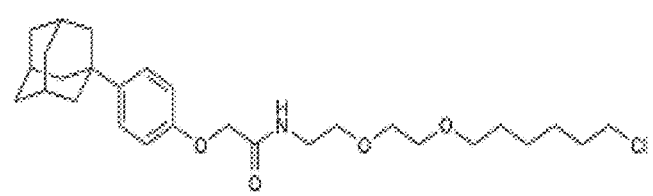
Figure 5:
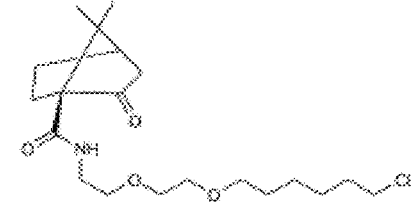
Figure 5:
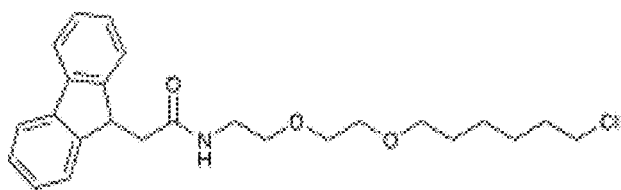
Figure 5:
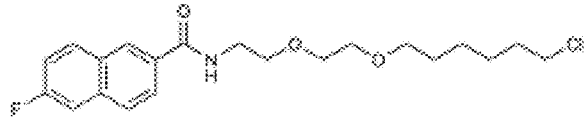
Figure 5:
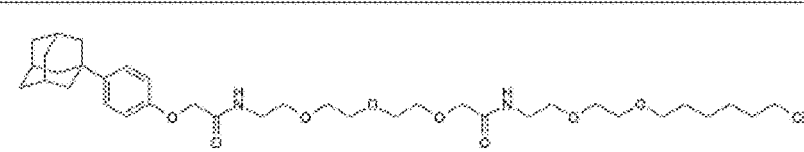
Figure 5:
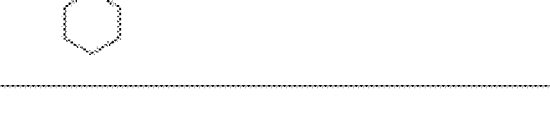
Figure 5:
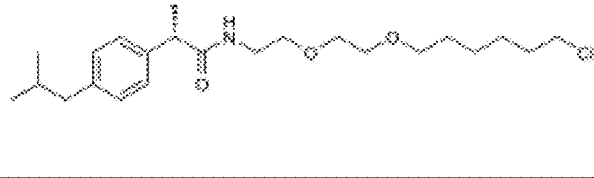
Figure 5:
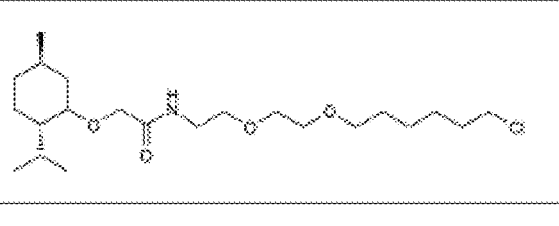
Figure 5:
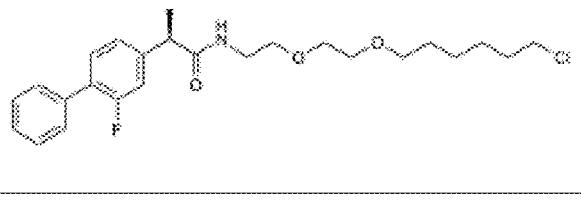
Figure 5:
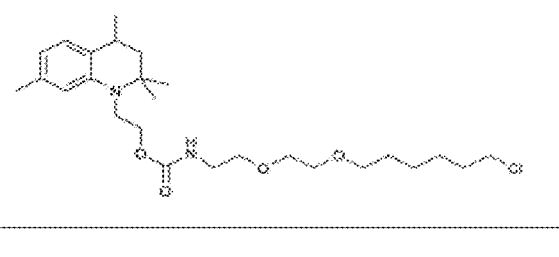
Figure 5:
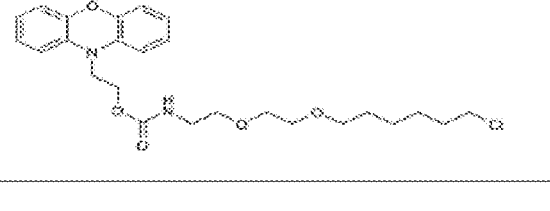
Figure 5:
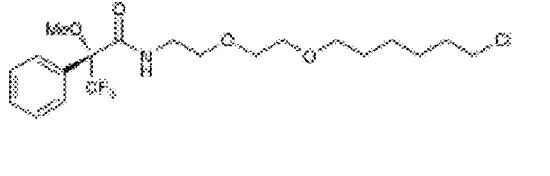
Figure 5:
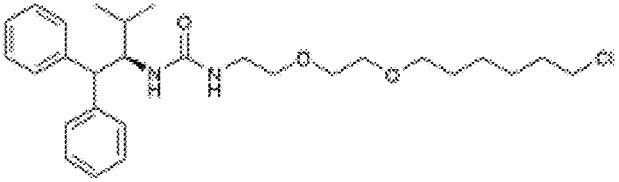
Figure 5:
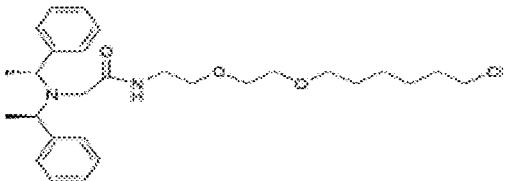
Figure 5:
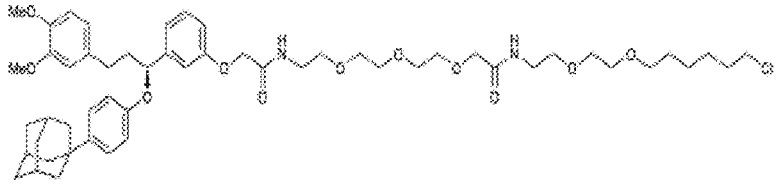
Figure 5:
Figure 5:
Figure 5:
Figure 5:
Figure 5:
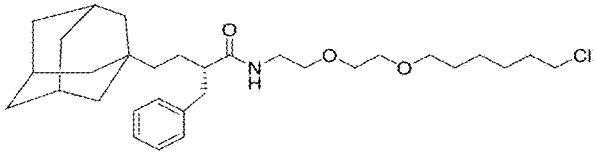
Figure 5:
Figure 5:
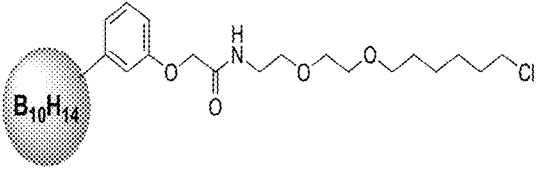

The inventors designed 21 structurally distinct scaffolds as the basis for our hydrophobic Tags (HyTs), and synthesized and tested 30 compounds across these scaffolds composed of hydrophobic moieties linked to the HaloTag haloalkane reactive linker (Table 1, FIG. 5). In designing the hydrophobic portion of these bifunctional molecules, the inventors used the compound library available in the Yale University Small Molecule Discovery Center as an informal resource to identify compounds that (1) maximized hydrophobicity, (2) minimized molecular weight, and (3) incorporated chemically diverse and commercially available scaffolds. To determine their biological activity, we generated a stable HEK 293T cell line expressing a luciferase-HaloTag fusion protein and treated these cells with the HyT compounds at 1 µM for 24 hours. Remarkably, several non-toxic compounds appeared to reduce luciferase activity and we characterized the five most potent compounds further (FIG. 1). All five HyTs exhibited high hydrophobicity scores (logP ranging from +3 to +5) and were active in a concentration-dependent manner, whereas the HyT5 control compound with two PEG groups did not decrease the luciferase activity (FIG. 1). Based on these initial data, we continued our investigation of hydrophobic tagging-induced degradation with hydrophobic containing HyT13 because of the reported high stability and cell permeability of compounds bearing adamantyl groups[27,28].

Figure 6:
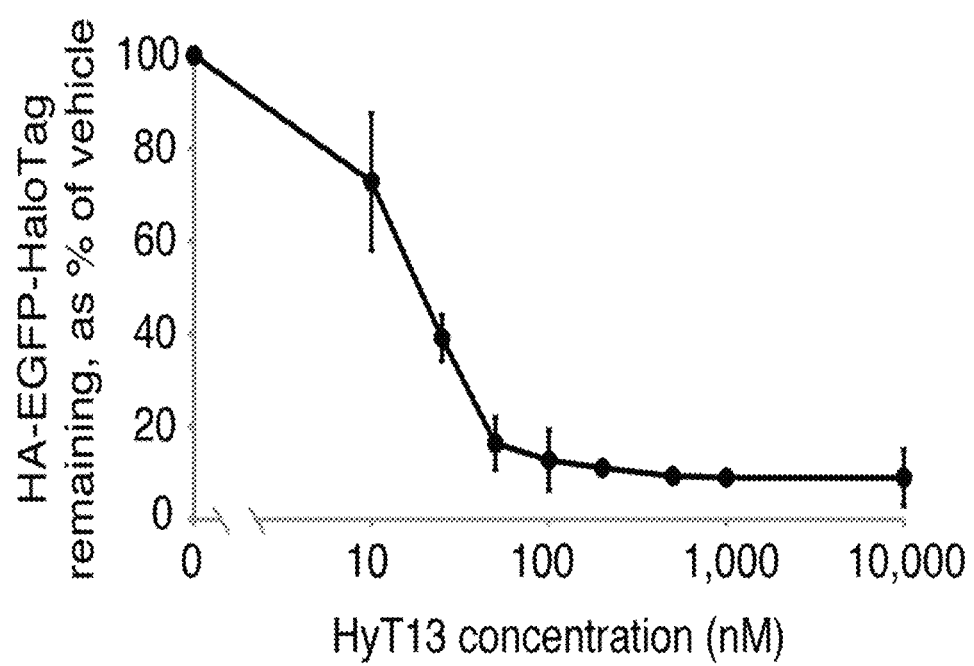
FIG. 6 shows the concentration curve of HyT13. Flp-In 293 cells expressing HA-EGFP-HaloTag were treated with indicated concentrations of HyT13 for 24 hours. The lysates were probed with anti-HA and anti-β-actin antibodies, with β-actin serving as a loading control. Shown is quantification of three separate experiments, with error bars representing SEM.
Figure 7:
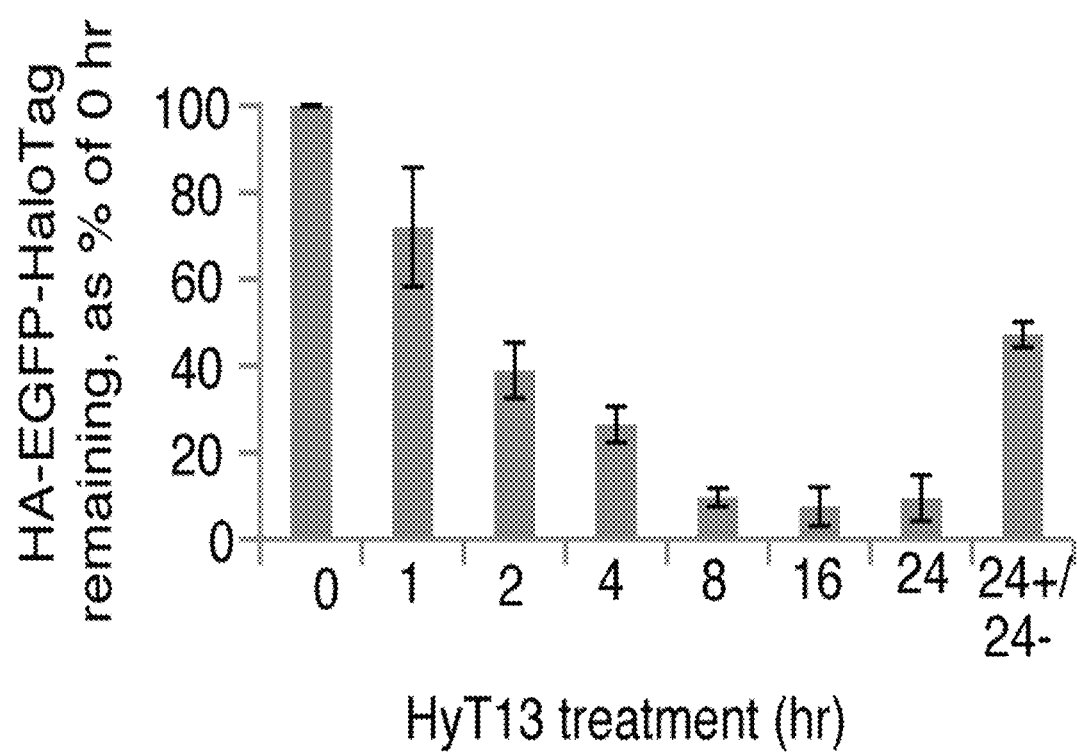
FIG. 7 shows the time course of HyT13 activity. Flp-In 293 cells expressing HA-EGFP-HaloTag cells were treated for the indicated times with 1 µM HyT13 and the lysates were probed with anti-HA and anti-β-actin antibodies. The rightmost sample was treated with HyT13 for 24 hours, after which HyT13-free media was provided for 24 hours. Shown is quantification of three separate experiments, with error bars representing SEM.
Figure 8:
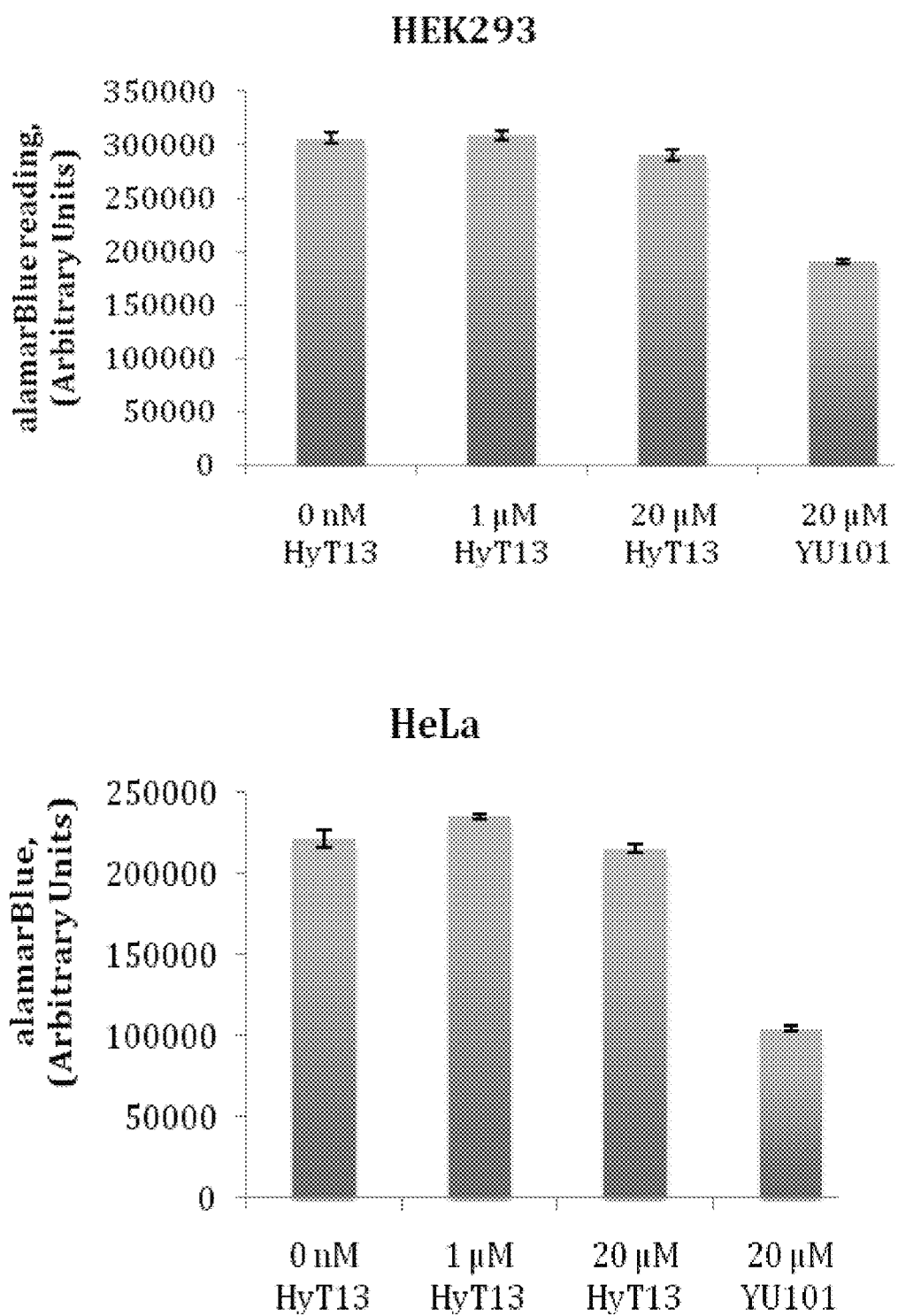
FIG. 8 shows that compound HyT13 exhibits no toxicity at doses up to 20 µM HyT13. HEK293 or HeLa cells were treated with indicated concentrations of HyT13 for 24 hours. The oxidation-reduction indicator Resazurin (alamarBlue, Invitrogen) was employed to determine cell viability. The proteasome inhibitor YU101 is toxic to cells at indicated concentration and served as a positive control for the assay.
Figure 12A:
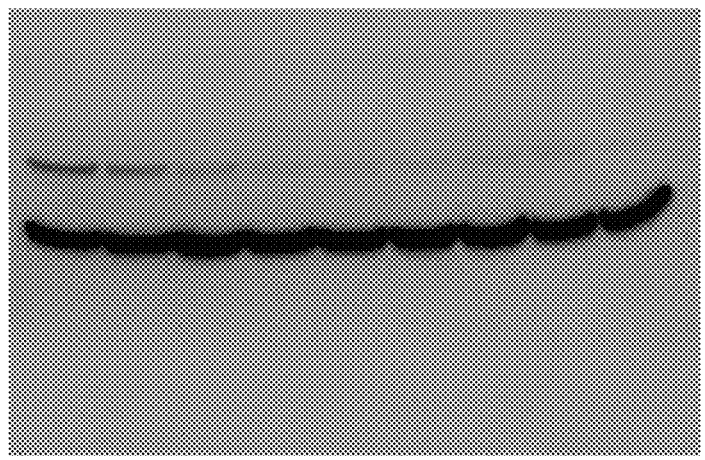
FIGS. 12a-e show representative immunoblot gel images of several fusion proteins degradations as described in the experimental section of the present application.
Figure 12B:
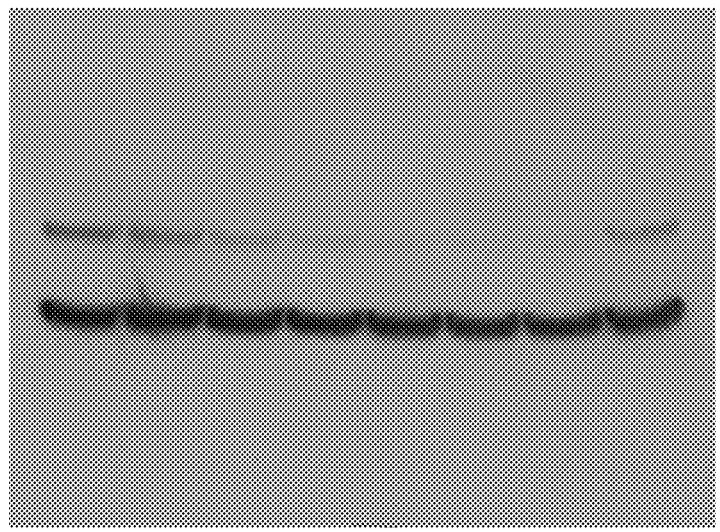
Figure 12C:
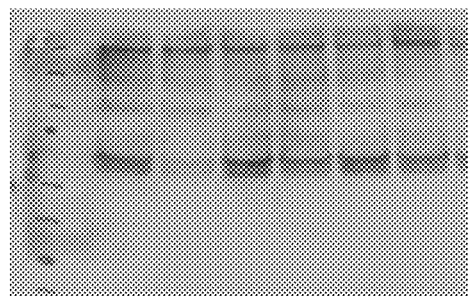
Figure 12C:
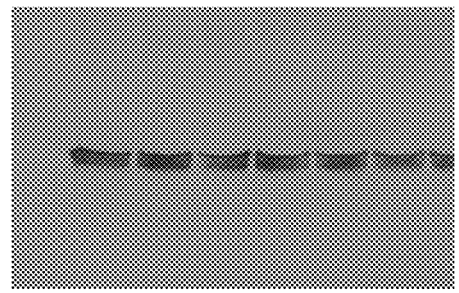
Figure 12D:
Figure 12D:
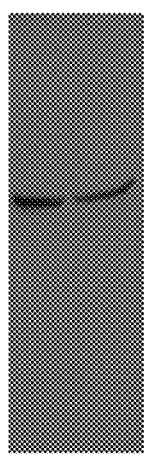
Figure 12D:
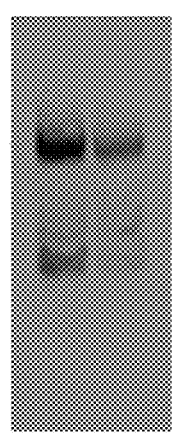
Figure 12D:
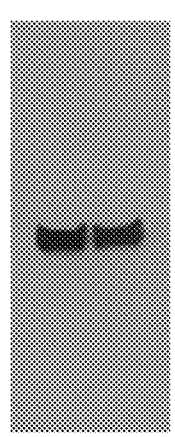
Figure 12D:
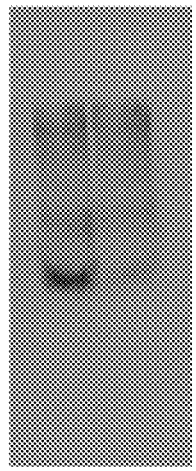
Figure 12D:
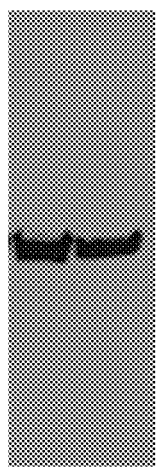
Figure 12D:
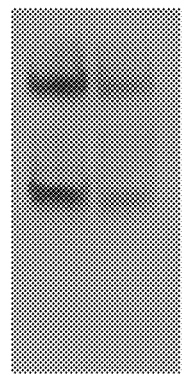
Figure 12D:
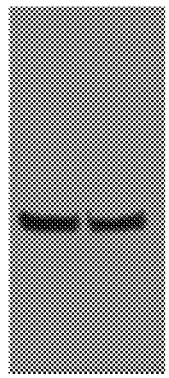
Figure 12D:
Figure 12D:
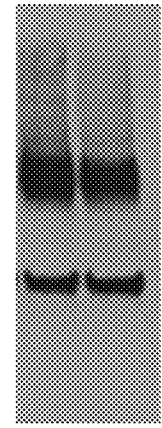

As the luciferase assay relied on the loss-of-activity of the luciferase-HaloTag fusion protein, we wanted to determine whether the decrease in luciferase activity resulted from the degradation of the entire fusion protein or perhaps simply inhibition of luciferase activity. We generated a stable Flp-In 293 cell line with a single integration site containing HA-EGFP-HaloTag fusion protein, and employed this cell line to perform kinetic studies with HyT13. Immunoblotting showed that HyT13 efficiently degraded the fusion protein, with a maximal effect achieved at 100 nM (FIG. 12a). The $IC_{50}$ of HyT13 was determined to be 21 nM (FIG. 6). A time course experiment revealed that the full effect is reached within 8 hours, with 50% degradation observed by 1.5 hours (FIG. 12b and FIG. 7). When cells were treated with 1 µM HyT13 for 24 hours, and then the HyT13 was removed for 24 hours, the protein level recovered to half the starting levels. No cellular toxicity was observed at 20 µM of HyT13, a dose of 1000-fold over the $IC_{50}$ value (FIG. 8). Consistent with our hypothesis that hydrophobic tagging mimics a partially denatured protein state and that the protein is ultimately delivered to the proteasome for degradation, inclusion of proteasome inhibitors MG132 and YU101[29] blocked HyT13 mediated degradation (FIG. 12c). To verify that the observed decrease in HA-EGFP-HaloTag levels does not result from masking of the HA epitope during immunoblotting, we generated a HeLa cell line stably expressing EGFP-HaloTag and analyzed the intracellular fluorescence by flow cytometry. Consistent with our previous observations, treatment of these cells with 1 µM of HyT13 for 24 hours reduced the mean fluorescence intensity of cells almost 7-fold. Together, these findings provide the first experimental evidence that hydrophobic tagging represents a viable strategy for the control of protein levels.

Degradation of Transmembrane and Zebrafish Proteins

One limitation of existing technologies for small molecule control of protein levels has been the difficulty of degrading transmembrane proteins[9]. To determine if hydrophobic tagging shares this limitation, we constructed several transmembrane-HA-HaloTag fusion proteins, such that the HaloTag portion would be intracellular. Ror2 is a single-pass receptor tyrosine kinase-like orphan receptor, which functions in Wnt ligand signaling[30]. Likewise, CD3E is a single-pass cell surface glycoprotein involved in antigen recognition[31]. CD9 is a 4-pass transmembrane protein from the tetraspanin family and it functions in integrin signaling[32]. Finally, G-protein coupled receptors GPR40 and Frizzled-4 are 7-pass transmembrane receptors for long-chain free fatty acids and Wnt proteins, respectively[33,34]. Treatment of HEK 293T cell lines stably expressing these transmembrane HaloTag fusion proteins with HyT13 efficiently induced their degradation (FIG. 12d), demonstrating the potential of our hydrophobic tagging system to degrade transmembrane proteins. These experiments show that fusions to either the amino or carboxy terminus of the HaloTag protein are susceptible to this small molecule-induced degradation strategy and that transmembrane proteins can be degraded by HyT13.

Figure 12E:
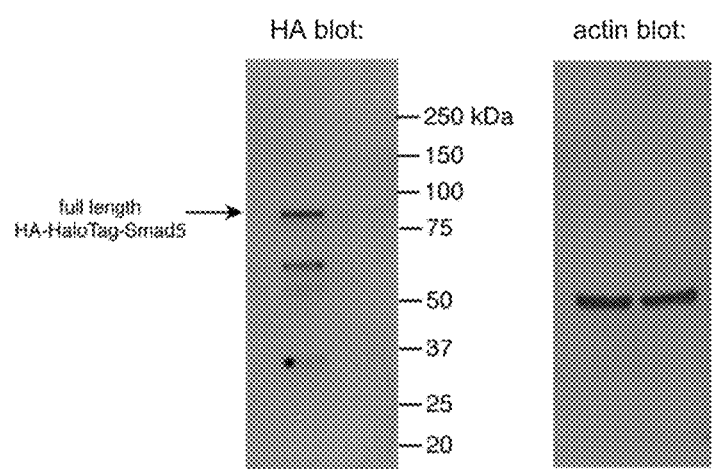

We also explored the possibility of employing the hydrophobic tagging system in the zebrafish *Danio rerio*. We injected HA-HaloTag-Smad5 cRNA into zebrafish embryos and then treated the embryos with either vehicle or HyT13. Immunoblotting of injected embryo lysates revealed that the fusion protein is very efficiently degraded, demonstrating that HyT13 is able to penetrate the chorion and can direct the HaloTag fusion proteins for degradation in zebrafish (FIG. 12e). These experiments show that HyT13 is capable of degrading fusion proteins in various cell lines, as well as in zebrafish embryos.

HyT13 Suppresses HaloTag-RasG12V Tumor Burden in Mice

Figure 13:
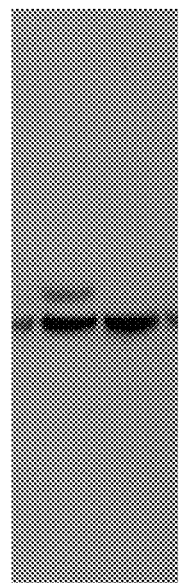
FIG. 13 shows the immunoblot gel images of HA-HaloTag-HRas(G12V) fusion protein.
Figure 13:
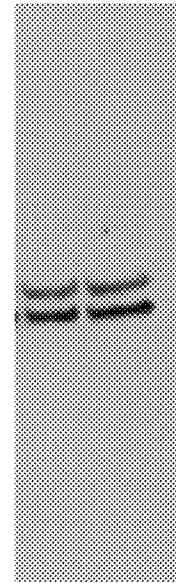

We next explored the functional utility of HaloTag-based degradation of an oncogene by HyT13 both in cell culture and in mice. The small GTPase H-Ras is one of the most commonly mutated genes in cancer, with up to 90% of cancers harboring activating mutations in this gene[35]. Activating mutations, such as the H-RasG12V allele, lead to decreased dependence on extracellular mitogenic signals. Ectopic expression of H-RasG12V in mouse fibroblast cell line NIH-3T3 can lead to a transformed phenotype, as demonstrated by assays in cell culture and in mice. When H-RasG12V expressing cells are grown in culture under low serum conditions they lose cell-to-cell contact inhibition and form distinct foci instead of growing as a cellular monolayer. Furthermore, these transformed cells are capable of tumor formation when injected into immuno-compromised nude mice[36,37]. We investigated whether (1) HaloTag-H-RasG12V driven focus formation can be suppressed in NIH-3T3 cells and (2) HaloTag-H-RasG12V driven tumor burden in mice can be reduced by administration of HyT13. First, NIH-3T3 cells were stably infected with a HA-HaloTag-H-RasG12V retroviral construct. The encoded fusion protein was readily degraded with HyT13 (FIG. 13a). To test the HaloTag receptor specificity for HyT13, we generated a point mutation in the HaloTag protein (HaloTagD106A) that is unable to form a covalent bond with the reactive chloroalkane in HyT13[26]. Unlike HA-HaloTag-H-RasG12V, HA-HaloTag(D106A)-H-RasG12V fusion protein was unaffected by HyT13 (FIG. 13a). Next, we plated both cell lines sparsely ($10^5$ cells/10-cm plate) in 10% FBS containing media. The next day, the media was replaced with 1% FBS containing media and the cultures were treated with either vehicle or HyT13. By day 6, both vehicle-treated cell lines and HyT13-treated HA-HaloTag(D106A)-H-RasG12V expressing cells had formed many foci, whereas HA-HaloTag-H-RasG12V expressing cells treated with HyT13 had grown a normal monolayer of cells, much like the parental NIH-3T3 cells (FIG. 13b-c). In the absence of HyT13, HA-HaloTag-H-RasG12V expressing cells exhibited slightly higher number of colonies than HA-HaloTag (D106A)-H-RasG12V cells. However, we attribute this observation to slight differences in retroviral infection efficiencies, since we have observed instances where the HaloTag(D106A)-H-RasG12V cells exhibit more colonies than the HA-HaloTag-H-RasG12V cells as well (data not shown). These results demonstrate that hydrophobic tagging can be used to reduce protein activity in the context of in vitro cell culture.

Figure 9:
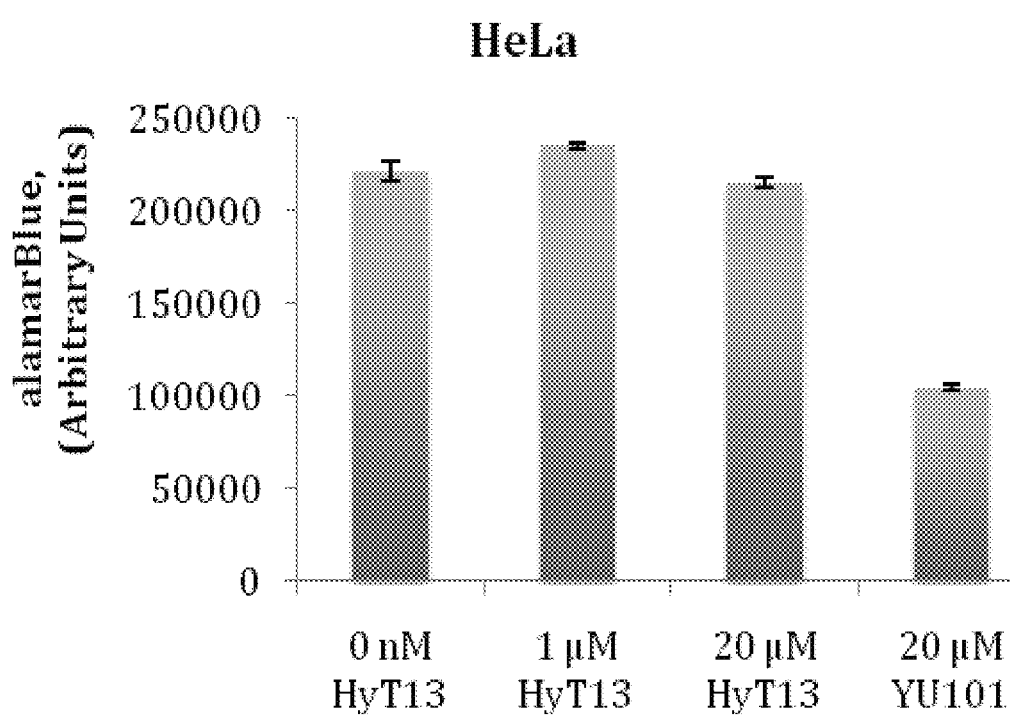
FIG. 9 shows that there was no observed toxicity in mice treated with HyT13. Nude mice were daily IP injected with indicated concentrations of HyT13 and were monitored for weight gain during the 14-day experiment. Shown is the percent weight gained during the 14-day period for each treatment group ±SEM. Each treatment group consisted of 7 mice.
Figure 10:
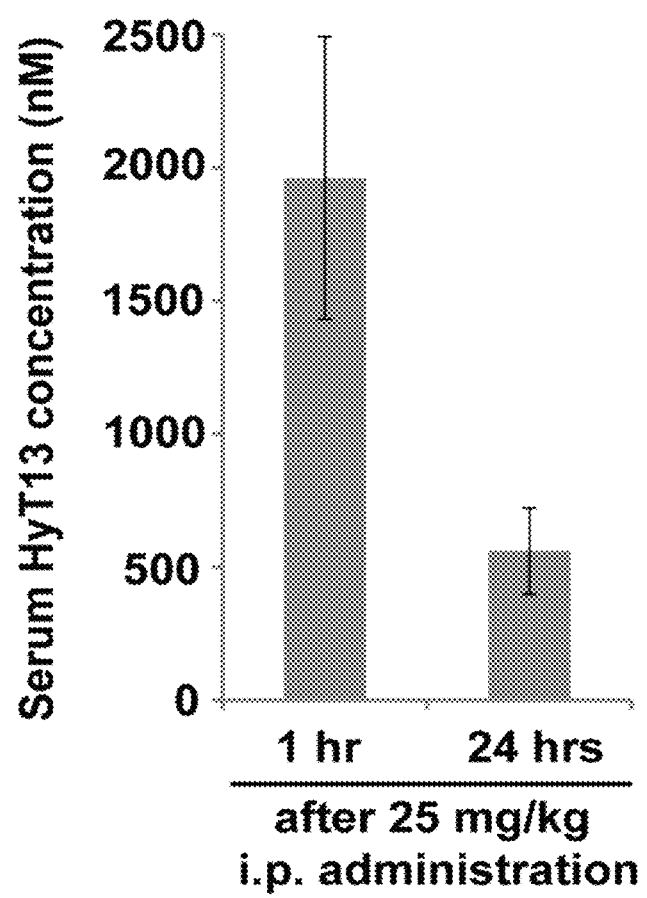
FIG. 10 shows a serum HyT13 determination. Webster Swiss mice received IP injections of 25 mg/kg of HyT13. The injection volume was 10 µL, consisting of 5 µL, of Cremophor EL excipient and 5 µL, of HyT13 in DMSO. Blood was collected from the carotid artery 1 and 24 hours after the injection. The blood was allowed to coagulate for 10 minutes, centrifuged at 10,000 g for 5 minutes and the serum was pipetted into a new tube. Ten microliters of the serum were used for a bio-reporter assay, consisting of the ability to degrade luciferase activity in HEK 293T luciferase-HaloTag cells. The serum concentration of HyT13 was based on a concentration curve of HyT13 performed alongside the bio-reporter assay. No degradation activity was observed in serum from mice receiving no HyT13. Each treatment group consisted of three mice. Shown is the mean serum HyT13 level±SEM.
Figure 11:
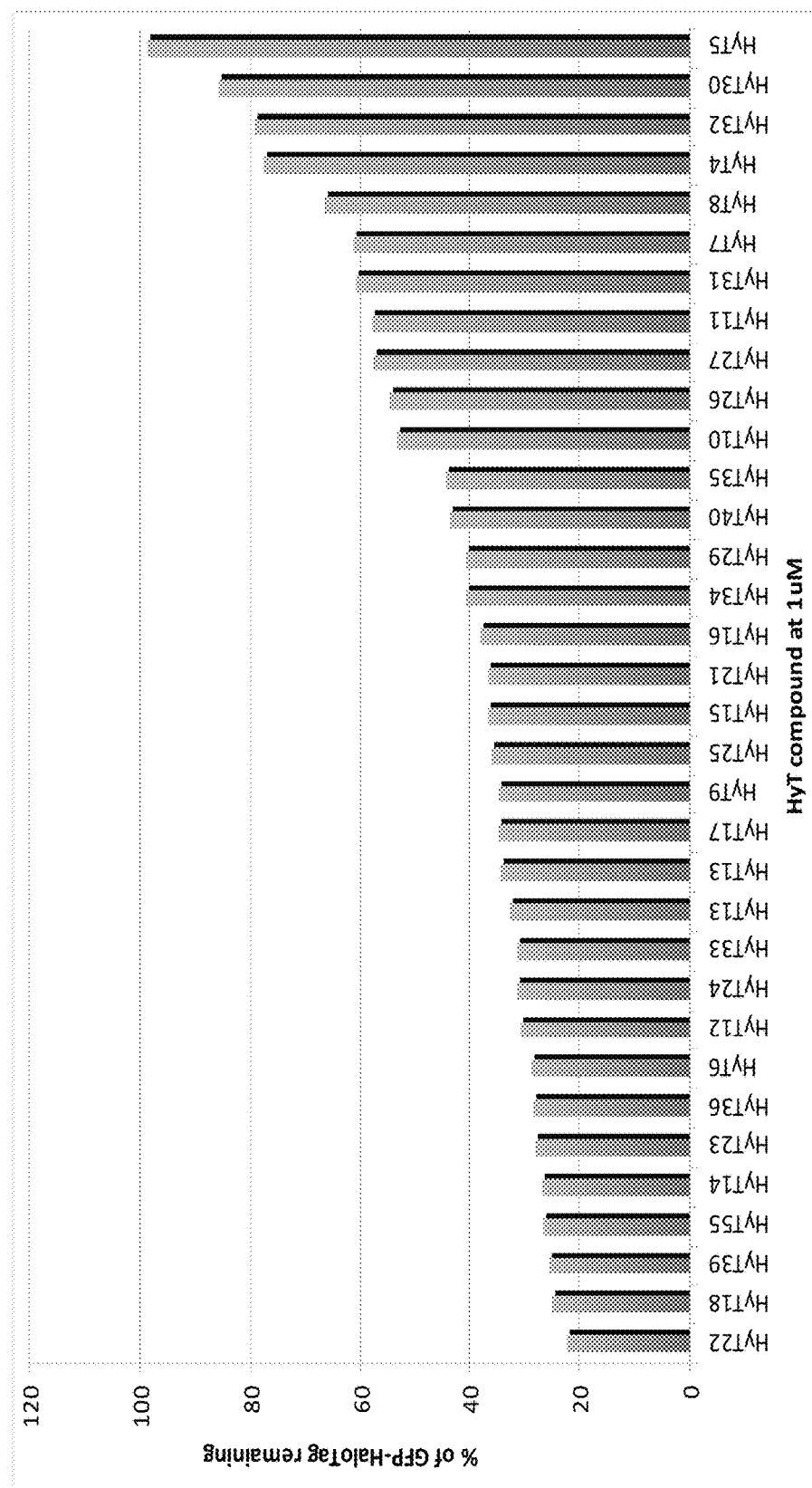
FIG. 11 shows the results of a number of synthesized HyT compounds on the degradation of a green fluorescent protein halotag fusion protein at a concentration for each compound at 1 µM.

To examine whether the HaloTag:HyT13 based system could be used in mouse models to relieve the H-RasG12V-driven tumor burden, we first evaluated the pharmacokinetics of HyT13. We performed a maximum tolerated dose experiment with HyT13 in nude mice at doses up to 100 mg/kg over a 14-day treatment regimen. No obvious phenotype was observed even at the highest dose (FIG. 9). Next, we sought to determine the serum bioavailability of HyT13 following injections. HyT13 was administered at 25 mg/kg by intraperitoneal (IP) injection into Swiss Webster mice and the serum was collected at 1 and 24 hours post-injection. At 1 hour post HyT13 administration the blood serum concentration was approximately 2 µM, and by 24 hours the HyT13 concentration had dropped to about 500 nM (FIG. 10). Based on our previous experiments in a cell culture setting, we speculated that these serum HyT13 concentrations would be sufficient to suppress H-RasG12V tumor formation in mice. To test this, we injected NIH-3T3 cells expressing HA-HaloTag-H-RasG12V into the flank of nude mice and on the same day started a daily treatment regimen of vehicle, 25 mg/kg HyT13 or 100 mg/kg HyT13. Obvious solid tumor masses were observed on day 9 in vehicle-treated mice and the tumor volume grew exponentially until day 13, when the animals were sacrificed. The tumors in HyT13 mice were on average 6 times smaller than in vehicle treated mice, suggesting that HyT13 was able to reduce H-RasG12V tumor formation (FIG. 13d). These data clearly demonstrate the utility of the HaloTag:HyT13 system in perturbing protein function in live animals.

Discussion

The present invention relates to a novel hydrophobic tagging technology to systematically degrade levels of a specific protein upon addition of a small molecule (FIG. 9). This strategy has several benefits over the existing technologies. First, protein degradation is achieved upon compound administration as opposed to following ligand withdrawal. This aspect is particularly relevant when a protein needs to be expressed for long periods before the study, as there is no continuous ligand treatment necessary to maintain expression of the POI. In contrast, DD-based methods (see Introduction) of controlling protein abundance require constant drug administration, which can be both time-consuming and expensive. Also, there are likely fluctuations in the concentration of the fusion protein between ligand administrations using the DD-based system, whereas the expression of the HaloTag fusion protein is stable in the absence of the degradation signal. Therefore, depending on the application, it can be desirable to have a system where the small molecule induces degradation, rather than stabilization, of the POI. Second, our HaloTag:HyT13 method relies on the single introduction of a fusion domain to the POI. This feature contrasts with the auxin system, where an exogenous plant E3 ligase must be expressed in addition to the fusion protein. Third, almost all human and mouse genes are commercially available as both N- and C-terminal HaloTag fusions in transient and lentiviral expression vectors. These protein fusions with the 34 kDa HaloTag receptor are proving useful in many studies of protein function since they can be readily labeled in vivo and purified using fluorescent or biotinylated HaloTag reagents. The ability to degrade these fusion proteins with the hydrophobic tag HyT13 only adds to the repertoire of possible HaloTag applications. Although HyT13 is not yet commercially available, this small molecule can be obtained using standard synthetic methods in four steps from commercially available starting materials with an overall yield of 63% (Scheme 2, above).

One of the criticisms that surround the several FKBP12 based degradation systems is their reliance on either rapamycin, FK506 or their derivatives to cause protein perturbation. Since these are bioactive small molecules, they could induce biological effects unrelated to perturbing the POI. In contrast, HaloTag dehalogenase is a bacterial gene and covalent binding of HyT13 to HaloTag affords this system a high degree of specificity. This bioorthogonality may explain the lack of noticeable HyT13 cytotoxicity even upon 1,000-fold administration over its $IC_{50}$ value of 21 nM in cell culture. Moreover, mice injected daily with HyT13 at 100 mg/kg for 14 days gained weight normally, suggesting that HyT13 possesses no in vivo toxicity even at this high dose.

Like several other systematic degradation methods, the HaloTag:HyT13 methodology is not able to degrade endogenous proteins unless the HaloTag gene is fused with the gene of interest. However, there are two viable strategies to overcome this limitation and subject endogenous proteins to Halotag:HyT13-mediated regulation in culture or live animals. First, it is possible to generate HaloTag fusion constructs via targeted genome engineering. Recent advances in zinc finger nucleases[20,38,39] and homologous recombination[40] technologies open the possibility of systematically tagging endogenous proteins in rodents in a manner similar to yeast. The second approach would be to inactivate the endogenous gene by knockdown or knockout techniques and introduce the corresponding HaloTag fusion gene into the animal. Both approaches should be amenable to bypassing an early requirement of an essential gene, thus allowing the study of its function later during organogenesis or disease development.

In summary, herein we describe a chemical biology approach to systematically degrade any POI in either cell culture or whole animals. The system requires construction of a single fusion protein, which is specifically degraded by the addition of a non-toxic, low-molecular weight hydrophobic tag. We believe this system is particularly amenable to animal studies, as we have shown here with experiments in zebrafish and mice. Additionally, our findings suggest that hydrophobic tagging represents a novel approach to promote targeted degradation of endogenous proteins independent of the HaloTag:HyT13 system.

REFERENCES

1 Overington, J. P., Al-Lazikani, B. & Hopkins, A. L. How many drug targets are there? *Nat Rev Drug Discov* 5, 993-996, doi:nrd2199 [pii] 10.1038/nrd2199 (2006).

2 Russ, A. P. & Lampel, S. The druggable genome: an update. *Drug Discov Today* 10, 1607-1610, doi:S1359-6446(05)03666-4 [pii] 10.1016/S1359-6446(05)03666-4 (2005).

3 Dixon, S. J. & Stockwell, B. R. Identifying druggable disease-modifying gene products. *Curr Opin Chem Biol* 13, 549-555, doi:S1367-5931(09)00107-0 [pii] 10.1016/j.cbpa.2009.08.003 (2009).

4 Crews, C. M. Targeting the undruggable proteome: the small molecules of my dreams. *Chem Biol* 17, 551-555, doi:S1074-5521(10)00196-1 [pii] 10.1016/j.chembiol.2010.05.011 (2010).

5 Luo, J. et al. A genome-wide RNAi screen identifies multiple synthetic lethal interactions with the Ras oncogene. *Cell* 137, 835-848, doi:S0092-8674(09)00529-7 [pii] 10.1016/j.cell.2009.05.006 (2009).

6 Krishnan, M. N. et al. RNA interference screen for human genes associated with West Nile virus infection. *Nature* 455, 242-245, doi:nature07207 [pii] 10.1038/nature07207 (2008).

7 Karlas, A. et al. Genome-wide RNAi screen identifies human host factors crucial for influenza virus replication. *Nature* 463, 818-822, doi:nature08760 [pii] 10.1038/nature08760 (2010).

8 Whitehead, K. A., Langer, R. & Anderson, D. G. Knocking down barriers: advances in siRNA delivery. *Nat Rev Drug Discov* 8, 129-138, doi:nrd2742 [pii] 10.1038/nrd2742 (2009).

9 Schrader, E. K., Wilmington, S. R. & Matouschek, A. Making it easier to regulate protein stability. *Chem Biol* 17, 917-918, doi:S1074-5521(10)00316-9 [pii] 10.1016/j.chembiol.2010.09.004 (2010).

10 Nishimura, K., Fukagawa, T., Takisawa, H., Kakimoto, T. & Kanemaki, M. An auxin-based degron system for the rapid depletion of proteins in nonplant cells. *Nat Methods* 6, 917-922, doi:nmeth.1401 [pii] 10.1038/nmeth.1401 (2009).

11 Schneekloth, J. S., Jr. et al. Chemical genetic control of protein levels: selective in vivo targeted degradation. *J Am Chem Soc* 126, 3748-3754, doi:10.1021/ja039025z (2004).

12 Sakamoto, K. M. et al. Protacs: chimeric molecules that target proteins to the Skpl-Cullin-F box complex for ubiquitination and degradation. *Proc Natl Acad Sci USA* 98, 8554-8559, doi:10.1073/pnas.141230798 141230798 [pii] (2001).

13 Robinson, M. S., Sahlender, D. A. & Foster, S. D. Rapid inactivation of proteins by rapamycin-induced rerouting to mitochondria. *Dev Cell* 18, 324-331, doi:S1534-5807(10)00013-4 [pii] 10.1016/j.devcel.2009.12.015 (2010).

14 Iwamoto, M., Bjorklund, T., Lundberg, C., Kirik, D. & Wandless, T. J. A general chemical method to regulate protein stability in the mammalian central nervous system. *Chem Biol* 17, 981-988, doi:S1074-5521(10)00305-4 [pii] 10.1016/j.chembiol.2010.07.009 (2010).

15 Banaszynski, L. A., Chen, L. C., Maynard-Smith, L. A., Ooi, A. G. & Wandless, T. J. A rapid, reversible, and tunable method to regulate protein function in living cells using synthetic small molecules. *Cell* 126, 995-1004, doi:S0092-8674(06)01013-0 [pii] 10.1016/j.cell.2006.07.025 (2006).

16 Clackson, T. et al. Redesigning an FKBP-ligand interface to generate chemical dimerizers with novel specificity. *Proc Natl Acad Sci USA* 95, 10437-10442 (1998).

17 Herm-Gotz, A. et al. Rapid control of protein level in the apicomplexan *Toxoplasma gondii*. *Nat Methods* 4, 1003-1005, doi:nmeth1134 [pii] 10.1038/nmeth1134 (2007).

18 Banaszynski, L. A., Sellmyer, M. A., Contag, C. H., Wandless, T. J. & Thorne, S. H. Chemical control of protein stability and function in living mice. *Nat Med* 14, 1123-1127, doi:nm.1754 [pii] 10.1038/nm.1754 (2008).

19. Dvorin, J. D. et al. A plant-like kinase in *Plasmodium falciparum* regulates parasite egress from erythrocytes. *Science* 328, 910-912, doi:328/5980/910 [pii] 10.1126/science.1188191 (2010).
20. Pruett-Miller, S. M., Reading, D. W., Porter, S. N. & Porteus, M. H. Attenuation of zinc finger nuclease toxicity by small-molecule regulation of protein levels. *PLoS Genet* 5, e1000376, doi:10.1371/journal.pgen.1000376 (2009).
21. Agashe, V. R., Shastry, M. C. & Udgaonkar, J. B. Initial hydrophobic collapse in the folding of barstar. *Nature* 377, 754-757, doi:10.1038/377754a0 (1995).
22. Gething, M. J. Role and regulation of the ER chaperone BiP. *Semin Cell Dev Biol* 10, 465-472, doi:S1084-9521(99)90318-X [pii] 10.1006/scdb.1999.0318 (1999).
23. Lins, L. & Brasseur, R. The hydrophobic effect in protein folding. *FASEB J* 9, 535-540 (1995).
24. Blond-Elguindi, S. et al. Affinity panning of a library of peptides displayed on bacteriophages reveals the binding specificity of BiP. *Cell* 75, 717-728, doi:0092-8674(93)90492-9 [pii] (1993).
25. Kubota, H. Quality control against misfolded proteins in the cytosol: a network for cell survival. *J Biochem* 146, 609-616, doi:mvp139 [pii] 10.1093/jb/mvp139 (2009).
26. Los, G. V. et al. HaloTag: a novel protein labeling technology for cell imaging and protein analysis. *ACS Chem Biol* 3, 373-382, doi:10.1021/cb800025k (2008).
27. Mathias, L. J., Jensen, J. J., Reichert, V. T., Lewis, C. M. & Tullos, G. L. Adamantane-containing polymers. *Acs Sym Ser* 624, 197-207 (1996).
28. Tsuzuki, N. et al. Adamantane as a brain-directed drug carrier for poorly absorbed drug. 2. AZT derivatives conjugated with the 1-adamantane moiety. *J Pharm Sci* 83, 481-484 (1994).
29. Elofsson, M., Splittgerber, U., Myung, J., Mohan, R. & Crews, C. M. Towards subunit-specific proteasome inhibitors: synthesis and evaluation of peptide alpha', beta'-epoxyketones. *Chem Biol* 6, 811-822, doi:S1074-5521(99)80128-8 [pii] (1999).
30. Oishi, I. et al. The receptor tyrosine kinase Ror2 is involved in non-canonical Wnt5a/JNK signalling pathway. *Genes Cells* 8, 645-654, doi:662 [pii] (2003).
31. DeJarnette, J. B. et al. Specific requirement for CD3epsilon in T cell development. *Proc Natl Acad Sci USA* 95, 14909-14914 (1998).
32. Masellis-Smith, A. & Shaw, A. R. CD9-regulated adhesion. Anti-CD9 monoclonal antibody induce pre-B cell adhesion to bone marrow fibroblasts through de novo recognition of fibronectin. *J Immunol* 152, 2768-2777 (1994).
33. Briscoe, C. P. et al. The orphan G protein-coupled receptor GPR40 is activated by medium and long chain fatty acids. *J Biol Chem* 278, 11303-11311, doi:10.1074/jbc.M211495200 M211495200 [pii] (2003).
34. Kirikoshi, H. et al. Molecular cloning and characterization of human Frizzled-4 on chromosome 11q14-q21. *Biochem Biophys Res Commun* 264, 955-961, doi:10.1006/bbrc.1999.1612 50006-291X(99)91612-1 [pii] (1999).
35. Bos, J. L. ras oncogenes in human cancer: a review. *Cancer Res* 49, 4682-4689 (1989).
36. Parada, L. F., Tabin, C. J., Shih, C. & Weinberg, R. A. Human E J bladder carcinoma oncogene is homologue of Harvey sarcoma virus ras gene. *Nature* 297, 474-478 (1982).
37. Shih, C. & Weinberg, R. A. Isolation of a transforming sequence from a human bladder carcinoma cell line. *Cell* 29, 161-169, doi:0092-8674(82)90100-3 [pii] (1982).
38. Porteus, M. Design and testing of zinc finger nucleases for use in mammalian cells. *Methods Mol Biol* 435, 47-61, doi:10.1007/978-1-59745-232-8_4 (2008).
39. Ostrand-Rosenberg, S. Animal models of tumor immunity, immunotherapy and cancer vaccines. *Curr Opin Immunol* 16, 143-150, doi:10.1016/j.coi.2004.01.003 S0952791504000068 [pii] (2004).
40. Rago, C., Vogelstein, B. & Bunz, F. Genetic knockouts and knockins in human somatic cells. *Nat Protoc* 2, 2734-2746, doi:nprot.2007.408 [pii] 10.1038/nprot.2007.408 (2007).
41. Koh, E. Y., Chen, T. & Daley, G. Q. Novel retroviral vectors to facilitate expression screens in mammalian cells. *Nucleic Acids Res* 30, e142 (2002).
42. Gies, E. et al. Niclosamide prevents the formation of large ubiquitin-containing aggregates caused by proteasome inhibition. *PLoS One* 5, e14410, doi:10.1371/journal.pone.0014410 (2010).
43. Link, V., Shevchenko, A. & Heisenberg, C. P. Proteomics of early zebrafish embryos. *BMC Dev Biol* 6, 1, doi:1471-213X-6-1 [pii] 10.1186/1471-213X-6-1 (2006).

The invention claimed is:

1. A compound of formula

HYD-L$_R$, wherein:

HYD is a hydrophobic group selected from the group consisting of HTL-36, HTL-39 and HTL-40:

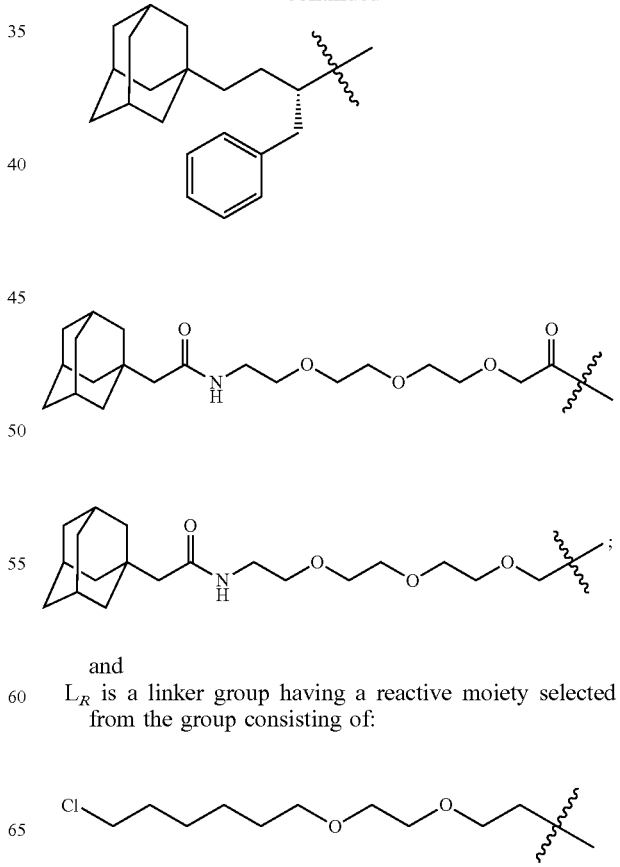

and

L$_R$ is a linker group having a reactive moiety selected from the group consisting of:

-continued

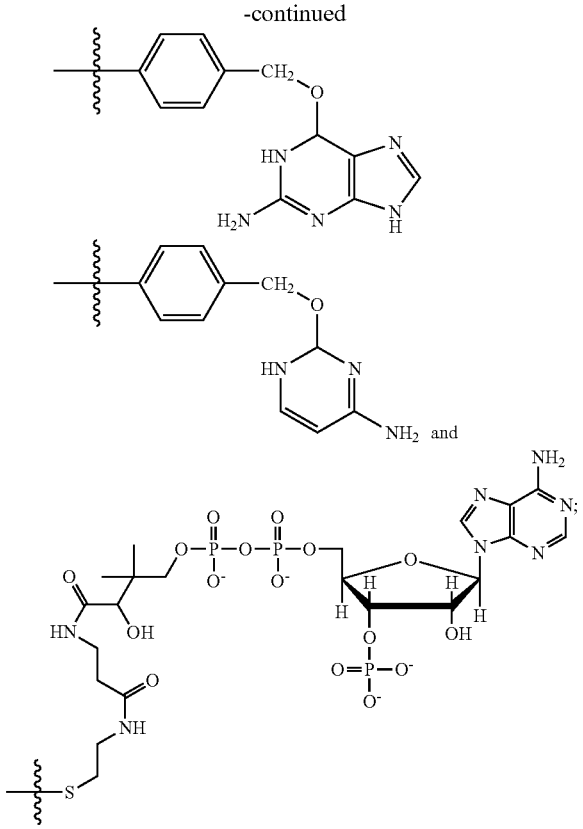

wherein the reactive moiety is capable of forming a covalent link between the HYD group and a target protein of interest.

2. The compound of claim 1, wherein the reactive moiety is a haloalkyl group optionally substituted with a monoether or diether group.

3. The compound of claim 1, wherein the target protein of interest comprises at least one selected from the group consisting of a haloalkane dehalogenase, O6-alkylguanine-DNA alkyltransferase, ACP synthase, SCP synthase, and SFP synthase.

4. The compound of claim 1, wherein the hydrophobic group has a ClogP of at least 4.0.

5. The compound of claim 1, wherein the target protein of interest is a structural protein, receptor, enzyme, cell surface protein, a protein involved in catalytic activity, an aromatase, a motor protein, a helicase, a metabolic protein, an antioxidant protein, proteolytic protein, biosynthesis related protein, a kinase, an oxidoreductase, a transferase, a hydrolase, a lyase, an isomerase, a ligase, enzyme regulator, signal transducer, cell motility related protein, membrane fusion related protein, cell communication related protein, cell differentiation related protein, cell adhesion protein, cell death protein, protein transporter, nuclear transport protein, ion transport protein, channel transporter protein, carrier protein, a permease, secretory protein, electron transport protein, chaperone protein, nucleic acid binding protein, transcription regulator protein, extracellular organization and biogenesis protein, or translation regulator protein.

6. A method of inducing degradation of a protein of interest in a cell, the method comprising: reacting intracellularly or on the surface of the cell the expressed protein of interest with a compound comprising the compound of claim 1, wherein the compound of claim 1, upon reaction with the protein of interest, forms a covalent bond with the protein of interest thus yielding a hydrophobically labeled protein, which undergoes degradation.

* * * * *